US012290591B2

(12) United States Patent
Fadel et al.

(10) Patent No.: US 12,290,591 B2
(45) Date of Patent: May 6, 2025

(54) FRAGRANCE COMPOSITIONS

(71) Applicant: Firmenich SA, Satigny (CH)

(72) Inventors: Addi Fadel, Plainsboro, NJ (US);
Valery Normand, Plainsboro, NJ (US);
Artem Kirshon, Plainsboro, NJ (US);
Nicholas O'Leary, Plainsboro, NJ
(US); Arnaud Struillou, Satigny (CH)

(73) Assignee: FIRMENICH SA, Satigny (CH)

( * ) Notice: Subject to any disclaimer, the term of this patent is extended or adjusted under 35 U.S.C. 154(b) by 586 days.

(21) Appl. No.: 17/426,168

(22) PCT Filed: May 15, 2020

(86) PCT No.: PCT/EP2020/063612
§ 371 (c)(1),
(2) Date: Jul. 28, 2021

(87) PCT Pub. No.: WO2020/234154
PCT Pub. Date: Nov. 26, 2020

(65) Prior Publication Data
US 2022/0096355 A1 Mar. 31, 2022

Related U.S. Application Data

(60) Provisional application No. 62/849,558, filed on May 17, 2019.

(30) Foreign Application Priority Data

Oct. 2, 2019 (EP) .................................... 19201721

(51) Int. Cl.
| | |
|---|---|
| *A61K 8/86* | (2006.01) |
| *A61K 8/34* | (2006.01) |
| *A61Q 5/00* | (2006.01) |
| *A61Q 13/00* | (2006.01) |
| *A61Q 19/00* | (2006.01) |

(52) U.S. Cl.
CPC .................. *A61K 8/86* (2013.01); *A61K 8/34* (2013.01); *A61K 8/342* (2013.01); *A61Q 5/00* (2013.01); *A61Q 13/00* (2013.01); *A61Q 19/00* (2013.01)

(58) Field of Classification Search
CPC . A61K 8/342; A61K 8/86; A61K 8/34; A61Q 5/00; A61Q 19/00; A61Q 13/00
USPC ........................................................ 512/2, 1
See application file for complete search history.

(56) References Cited

U.S. PATENT DOCUMENTS

| 2015/0164764 A1 | 6/2015 | Bonnet et al. |
| 2016/0362629 A1 | 12/2016 | Holland et al. |

FOREIGN PATENT DOCUMENTS

| CN | 107810259 A | 3/2018 | |
| WO | WO-2016200759 A1 * | 12/2016 | ............... A61K 8/34 |
| WO | 2019/156708 A1 | 8/2019 | |

OTHER PUBLICATIONS

Kibbe A H (Ed): "Handbook of pharmaceutical excipients, Carbomer, Glycerin, Isopropyl Myristate, Isopropyl Palmitate, Methylcellulose, Propylene Glycol", Jan. 1, 2000, Handbook of Pharmaceutical Excipients, American Pharmaceutical Assoc. [U.A.], Washington, DC; US, pp. 79-82, 220.
International Search Report and Written Opinion for corresponding International Application No. PCT/EP2020/063612 dated Jun. 18, 2020 (15 pages).

* cited by examiner

*Primary Examiner* — Jessica Whiteley

(57) ABSTRACT

The various aspects presented herein relate to the field of perfumery. In particular, the present disclosure provides compositions having an increased and/or improved long-lastingness and/or fragrance profile. In addition, the present disclosure provides methods of using such compositions to increase and/or improve the long-lastingness and/or fragrance profile of a fragrance composition.

16 Claims, 16 Drawing Sheets

FRAGRANCE COMPOSITIONS

The present application is the United States national stage application of PCT Application No. PCT/EP2020/063612, filed May 15, 2020, which claims benefit of priority of U.S. Application No. 62/849,558, filed May 17, 2019, and European Patent Application No. 19201721.8, filed Oct. 7, 2019, and which are hereby incorporated by reference as though set forth herein in their entirety.

FIELD OF THE INVENTION

Background

In the perfumery industry there is a constant need to find new technologies for prolonging the perception of perfumes over time. Such a need is particularly marked when dealing with perfumes rich in highly volatile perfuming ingredients which evaporate quickly, such that the fragrance intensity and/or fragrance profile, as perceived by the user and others, decreases and/or changes with time. The perceived extent of this decrease and/or change is further enhanced by the rapid evaporation of ethanol, present in high amounts in fragrances and "eau de toilette" (colognes), as well as in body splashes. Maintaining intensity and/or profile over time is one important consideration for a commercial fragrance composition. Indeed, consumers look for fragrance compositions that last all day long. For example, it is commonly accepted that a fragrance composition has to maintain a good intensity and/or fragrance profile for at least 8 hours to satisfy this consumer need, the main challenge being to maintain the intensity of the highly volatile perfuming ingredients.

Perfumers select perfuming ingredients to blend into a fragrance composition with the goal of achieving a specific fragrance profile of strength and character. In so doing, perfumers are required to bear in mind differences in the individual character and volatility of the perfuming ingredients that are the components of the full fragrance composition. Conventional fragrance compositions have fragrance profile characterized by a greater amount of low volatile perfuming ingredients and lower amounts of the more volatile perfuming ingredients. The low volatile perfuming ingredients are known as "base notes", while the more volatile perfuming ingredients can be further divided into high volatile perfuming ingredients, identified as "top or head notes", and medium volatile perfuming ingredients, identified as "middle or heart notes".

The differences in the volatilities of the perfuming ingredients that are used to formulate fragrance compositions may result in some limitations. For example, a common complaint by consumers is that middle notes tend to fade too quickly after application of the fragrance composition. Additionally, the character of the middle notes may be undesirably altered by the presence of large amounts of the base notes during the period known as the "dry-down" phase.

Thus, it is desirable to have a fragrance composition which retains a significant portion of its initial fragrance character over time, hence, the floral, fruity or spicy characters of the 'heart notes' are perceived for many hours It is also desirable that the fragrance strength of the fragrance composition remains noticeable to the consumer over longer periods of time. It is also desirable to be able to create new to the world fragrance profiles wherein one, or several, well-recognized heart note characters, are maintained over time.

Therefore, there remains a need for a composition that is perceived by the consumer over a long duration following application. There is also a need for a composition which exhibits enhanced intensity of the fragrance profile over time.

SUMMARY

One aspect presented herein, provides a composition, wherein the composition comprises:
- a. ethanol, in an amount from 30 to 75 wt % relative to the total weight of the composition;
- b. a fragrance component present in an amount from 0.04 to 40 wt %, relative to the total weight of the composition,
  wherein the fragrance component comprises:
  - i. a high volatility component an amount from 0.08 to 55 wt % of the fragrance component, comprising
    - a. a first at least one perfume raw material having a first vapor pressure greater than 0.08 Torr at 22° C.; and optionally
    - b. a second at least one perfume raw material having a first vapor pressure greater than 0.08 Torr at 22° C.;
  - ii. a medium volatility component in an amount from 0.08 to 85 wt % of the fragrance component, comprising:
    - a. a first at least one perfume raw material having a first vapor pressure range of 0.0008 to 0.08 Torr at 22° C.; and optionally
    - b. a second at least one perfume raw material having a first vapor pressure range of 0.0008 to 0.08 Torr at 22° C.; and
- c. at least one modulator in an amount from 0.1 to 50 wt %, relative to the total weight of the composition;

wherein the first vapor pressure of the at least one first perfume raw material of the high volatility component is determined in the absence of the at least one modulator;

wherein the first vapor pressure of the at least one second perfume raw material of the high volatility component is determined in the absence of the at least one modulator;

wherein the at least one modulator changes the first vapor pressure of the at least one second perfume raw material of the high volatility component to a second vapor pressure;

wherein the second vapor pressure of the at least one second perfume raw material of the high volatility component is in the range of 0.0008 to 0.08 Torr at 22° C.;

wherein the first vapor pressure range of the at least one first perfume raw material of the medium volatility component is determined in the absence of the at least one modulator;

wherein the first vapor pressure range of the at least one second perfume raw material of the medium volatility component is determined in the absence of the at least one modulator;

wherein the at least one modulator changes the first vapor pressure range of the at least one second perfume raw material of the medium volatility component to a second vapor pressure; and wherein the second vapor pressure of the at least one second perfume raw material of the medium volatility component is less than 0.0008 Torr at 22° C.

In one aspect, the fragrance component present in an amount from 0.04 to 20 wt %, relative to the total weight of the composition.

In one aspect, the composition further comprises water, in an amount of less than or equal to 15 wt % relative to the total weight of the composition.

In one aspect, the composition further comprises water, in an amount 5 to 15 wt % relative to the total weight of the composition.

In one aspect, the composition further comprises water, in an amount 0 to 5 wt % relative to the total weight of the composition.

In one aspect, the at least one modulator comprises a compound having:
  i. a vapor pressure of less than 0.0008 Torr at 22° C.;
  ii. at least two Hansen solubility parameters selected from a first group consisting of: an atomic dispersion force ($\delta_d$) from 12 to 20, a dipole moment ($\delta_p$) from 1 to 7, and a hydrogen bonding ($\delta_h$) from 2.5 to 11, when in solution with a compound having a vapor pressure greater than 0.08 Torr at 22° C.; and
  iii. at least two Hansen solubility parameters selected from a second group consisting of: an atomic dispersion force ($\delta_d$) from 14 to 20, a dipole moment ($\delta_p$) from 1 to 8, and a hydrogen bonding ($\delta_h$) from 4 to 11, when in solution with a compound having a vapor pressure range of 0.0008 to 0.08 Torr at 22° C.

In one aspect, the first group comprises at least two Hansen solubility parameters selected from the group consisting of: an atomic dispersion force ($\delta_d$) of 15.84±3.56, a dipole moment ($\delta_p$) of 4.15±2.65, and a hydrogen bonding ($\delta_h$) of 6.72±4.11, when in solution with a compound having a vapor pressure greater than 0.08 Torr at 22° C.

In one aspect, the second group comprises at least two Hansen solubility parameters selected from the group consisting of: an atomic dispersion force ($\delta_d$) of 16.86±2.72, a dipole moment ($\delta_p$) of 4.61±3.10, and a hydrogen bonding ($\delta_h$) of 7.66±3.29, when in solution with a compound having a vapor pressure range of 0.0008 to 0.08 Torr at 22° C.

In one aspect, the at least one modulator is selected from the compounds listed in Table 9.

In one aspect, the at least one modulator has an odor value from 1 to 10,000.

In one aspect, the at least one modulator has a C12.5 from 0.1 and 10 µg/l.

In one aspect, the composition further comprises at least one hydrophilic solvent. In one aspect, the at least one hydrophilic solvent is selected from the group consisting of: propylene glycol, dipropylene glycol, ethylene glycol, triethyl citrate, disiopropyl glycol monomethyl ether, diethylene glycol monoethyl ether; triacetin, methylmethoxybutanol, benzyl alcohol, propylene glycol n-butyl ether; a glycol ether, an ester of diethylene glycol, and a cellosolve derivative. In one aspect, the glycol ether is a glycol ether sold under the tradename DOWANOL. In one aspect, the ether of diethylene glycol is sold under the tradename CARBITOL.

In one aspect, the glycol ether sold under the tradename DOWANOL is selected from the group consisting of: DOWANOL™ DPMA Glycol Ether; DOWANOL™ PM Glycol Ether; DOWANOL EPH ELP; DOWANOL™ EPh; DOWANOL™ PnB Glycol Ether; DOWANOL™ TPnB; DOWANOL™ DPnB Glycol Ether; DOWANOL™ TPM Glycol Ether; DOWANOL™ PPh Glycol Ether; DOWANOL™ PnP Glycol Ether; DOWANOL™ DPH 255 Glycol Ether; DOWANOL™ PGDA Glycol Ether; DOWANOL™ DPM Glycol Ether; DOWANOL™ TPnB-H Gly Ether; DOWANOL™ Solvents for Home & Personal Care; DOWANOL™ DPnP Glycol Ether; DOWANOL™ PMA Glycol Ether; DOWANOL™ DiPPh Glycol Ether.

In one aspect, the cellosolve derivative is selected from the group consisting of: propyl cellosolve, butyl cellosolve, hexyl cellosolve, and cellosolve.

In one aspect, the high volatility component consists of only the first at least one perfume raw material having a first vapor pressure greater than 0.08 Torr at 22° C.

In one aspect, the medium volatility component consists of only the first at least one perfume raw material having a first vapor pressure range of 0.0008 to 0.08 Torr at 22° C.

In one aspect, the high volatility component comprises the second at least one perfume raw material having a first vapor pressure greater than 0.08 Torr at 22° C. in an amount from 0.1 to 40 wt % of the fragrance component.

In one aspect, the medium volatility component comprises the second at least one perfume raw material having a first vapor pressure range of 0.0008 to 0.08 Torr at 22° C. in an amount from 20 to 45 wt % of the fragrance component.

In one aspect, the fragrance component further comprises at least one perfume raw material having a first vapor pressure less than 0.0008 Torr at 22° C. in an amount from 10 to 55 wt % of the fragrance component.

In one aspect, the fragrance component further comprises at least one perfume raw material having a first vapor pressure less than 0.0008 Torr at 22° C. in an amount from 30 to 55 wt % of the fragrance component.

In one aspect, the fragrance component further comprises at least one perfume raw material having a first vapor pressure less than 0.0008 Torr at 22° C. in an amount from 10 to 30 wt % of the fragrance component.

One aspect presented herein, provides a perfuming consumer product comprising the composition according to an aspect presented herein.

One aspect presented herein provides a perfuming composition comprising the composition according to an aspect presented herein.

One aspect presented herein, provides a perfuming consumer product comprising the perfuming composition according to an aspect presented herein.

In one aspect, the perfuming consumer product is selected from the group consisting of a perfume, eau de toilette, home care product and a personal care product.

One aspect presented herein provides a method for modifying or enhancing the odor properties of a body surface, such as hair or skin, comprising contacting or treating the body surface with a composition according to the aspects presented herein.

One aspect presented herein provides a method for modifying or enhancing the odor properties of a substrate, such as fabric, furnishings, dishes, hard surfaces and related materials, comprising contacting or treating the body surface with a composition according to the aspects presented herein.

BRIEF DESCRIPTION OF THE FIGURES

While the specification concludes with claims particularly pointing out and distinctly claiming the invention, it is believed that the invention will be better understood from the following description of the accompanying figures wherein:

DETAILED DESCRIPTION

Figure 1:
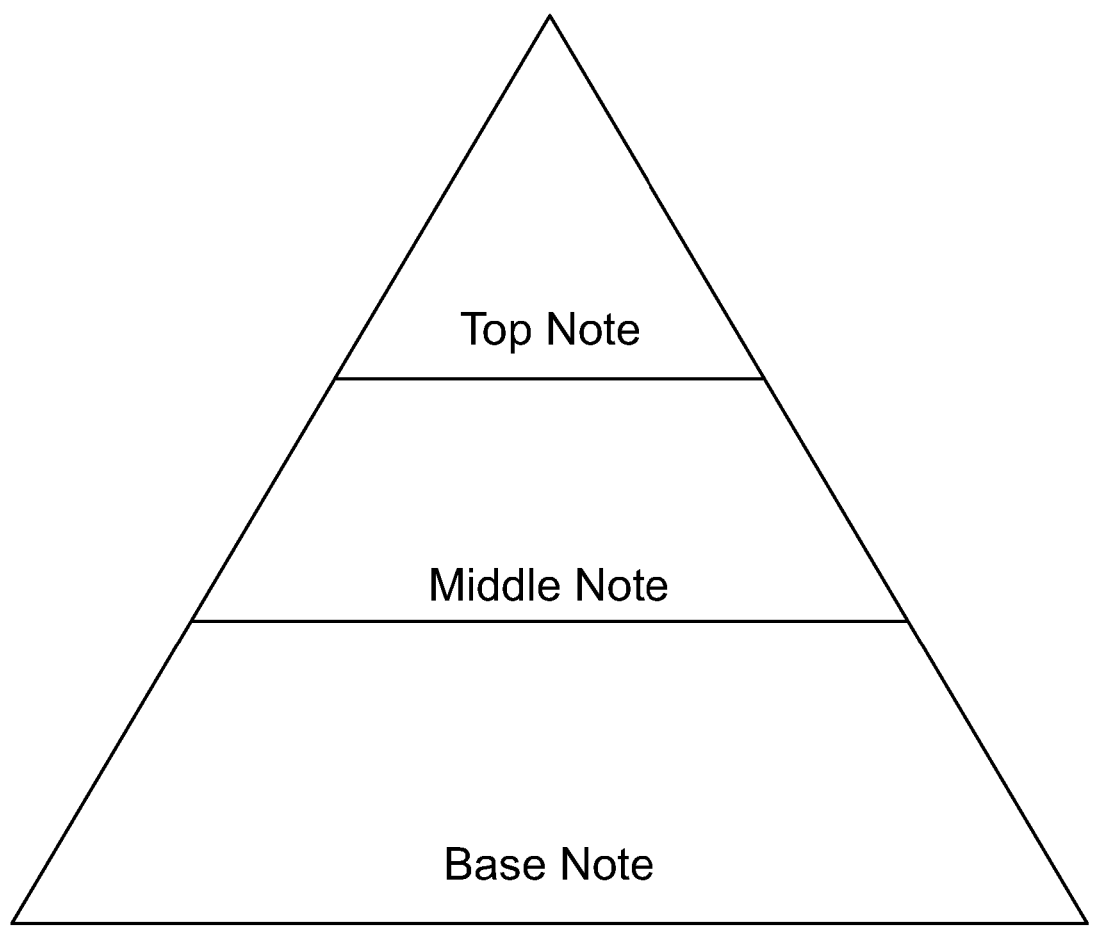
FIG. 1 provides a graphical representation of a conventional perfume structure.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Compositions According to Some Aspects Presented Herein:

The words "perfume" and "fragrance" are used here interchangeably to designate the component in the fragrance composition that is formed of perfuming ingredients, i.e. ingredients capable of imparting or modifying the odor of skin or hair.

By a "perfuming ingredient" it is meant here a compound of current use in perfumery, which is used essentially for its ability to smell pleasantly and to be capable of imparting hedonic effect, or a pleasant odor to the products into which it is incorporated, or to the surfaces, such as skin or hair, to which it is applied, on its own or in admixture with other such ingredients. In other words, a perfuming ingredient has the ability to impart or modify, in a positive or pleasant way, the odor of a composition or surface. When the latter has a malodor, the perfuming ingredient may also be capable of covering such malodor so as to render the overall perceived odor pleasant.

A "perfuming ingredient" may encompass any suitable perfume raw material for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also know for use as "perfuming ingredient(s)". The individual perfume raw materials which comprise a known natural oil can be found by reference to Journals commonly used by those skilled in the art such as "Perfume and Flavourist" or "Journal of Essential Oil Research", or listed in reference texts such as the book by S. Arctander, Perfume and Flavor Chemicals, 1969, Montclair, New Jersey, USA and more recently re-published by Allured Publishing Corporation Illinois (1994). Additionally, some perfume raw materials are supplied by the fragrance houses as mixtures in the form of proprietary specialty accords. Non-limiting examples of the perfuming ingredients useful herein include pro-fragrances such as acetal pro-fragrances, ketal pro-fragrances, ester pro-fragrances, hydrolyzable inorganic-organic pro-fragrances, and mixtures thereof. The perfuming ingredient may be released from the pro-fragrances in a number of ways. For example, by way of a non-limiting illustration, the fragrance may be released as a result of simple hydrolysis, or by a shift in an equilibrium reaction, or by a pH-change, or by enzymatic release.

As used herein, the term "fragrance profile" means the description of how the fragrance perceived by the human nose evolves over time from when it is first applied. It is a result of the combination of the top, middle and base notes, if present, of a fragrance. A fragrance profile is composed of 2 characteristics: 'intensity' and 'character'. The 'intensity' relates to the perceived strength whilst 'character' refers to the odor impression or quality of the perfume, i.e., fruity, floral, woody, etc.

By "modulator" or "fixative" it is understood here an agent having the capacity to affect the manner in which the odor, in particular its evaporation rate and intensity, of the compositions incorporating the modulator or fixative can be perceived by an observer or user thereof, over time, as compared to the same perception in the absence of the modulator or fixative.

As used herein, the terms "include", "includes" and "including" are meant to be non-limiting.

Referring to FIG. 1, conventional fragrance compositions have fragrance profile characterized by a greater amount of low volatile perfuming ingredients and lower amounts of the more volatile perfuming ingredients. The low volatile perfuming ingredients are known as "base notes", while the more volatile perfuming ingredients can be further divided into high volatile perfuming ingredients, identified as "top or head notes", and medium volatile perfuming ingredients, identified as "middle or heart notes".

Without intending to be limited to any particular theory, top notes tend to smell citrusy, green, light, fresh, and comprise typically from about 0.1 wt % to 40 wt %, relative to the total weight of the fragrance composition. Top notes tend to evaporate quickly due to their high volatility and are characterized by vapor pressure greater than 0.08 Torr at 22° C. (Calculated using Advanced Chemistry Development (ACD/Labs) Software VI 1.02 (© 1994-2013 ACD/Labs)). Typically, perfumers use top notes to deliver the initial impression of the composition but do not rely on them to contribute much to its overall fragrance profile over time after application.

Middle or heart notes make up from about 0.1 wt % to about 40 wt %, relative to the total weight of the fragrance composition. Generally, middle/heart notes become dominant to the untrained nose from several minutes after application and can last up to a few hours afterwards. Middle/heart notes are associated with floral aromas (e.g., jasmin, rose), fruity, aromatic, marine or spicy aromas and have an intermediate volatility in the vapor pressure range of 0.0008 to 0.08 Torr at 22° C.

Base or bottom notes can exist at greater than 30 wt % relative to the total weight of the perfume formulation. Alternatively, base notes can exist from about 45 wt % to about 80 wt % relative to the total weight of the perfume formulation. Base notes are characterized as animalic, woody, sweet, amber or musky, not being very volatile and having a vapor pressure less than 0.0008 Torr at 22° C. Typically, base notes are not perceived as dominant until several hours after the application of the fragrance composition, or during "dry-down". Base notes may be relied upon to improve the strength of the overall fragrance profile over time and replace the heart notes when these are declining. The consequence of using base notes at high levels is that they impart particular odor characters, such as for example, musky, woody, ambery, warm and sweet, which overpower and dominate the fragrance character over time. Some of these base notes have become such common materials (e.g., hedione, galaxolide, etc.) that many fragrance dry-downs appear repetitive, boring, non-memorable and un-interesting to consumers. However, if base notes are reduced or excluded then the fragrance strength weakens over time and does not last for a sufficient duration.

As used herein, the term "vapor pressure" means the partial pressure in air at a defined temperature for a given chemical species. It defines a chemical species' desire to be in the gas phase rather than the liquid or solid state. The higher the vapor pressure, the greater the proportion of the material that will, at equilibrium, be found in a closed headspace. It is also related to the rate of evaporation of a perfuming ingredient which is defined in an open environment where material is leaving the system. In one aspect, the vapor pressure is determined according to the reference program Advanced Chemistry Development (ACD/Labs) Software Version 11.02, (© 1994-2013). Examples of methods suitable to determine vapor pressure are disclosed in International Patent Application Publication No. WO 2015/089246 A1.

As used herein, the term "impact" means the efficacy or intensity of a perfume raw material during the first moments of product performance. For example, a top note may be noticed immediately when sniffing at the perfume bottle or some seconds after applying the product to the skin.

As used herein, the term "diffusion" is a measure of the distance over which the fragrance or perfume raw material is noticeable soon after application; high diffusion, for example, is desirable in a bath foam or a dishwashing detergent.

As used herein, the term "tenacity" means the long-term effectiveness of the perfume raw material in the perfumed product, such as upon the skin after use of a perfume or a toilet soap.

As used herein, the term "volume" means the effectiveness of the perfume raw material over distance, sometime after application.

In one aspect, the present invention provides for a composition comprising a fragrance component present in an amount of from about 0.04 wt % to 40 wt %, alternatively 1 wt % to about 40 wt %, alternatively less than about 25 wt %, alternatively less than about 20 wt %, alternatively less than about 15 wt %, alternatively less than about 10 wt % or alternatively less than about 8 wt %, relative to the total weight of the composition. Alternatively, the fragrance component is present in an amount of from about 0.04 wt %, 0.3 wt %, 1 wt %, 8 wt % or 10 wt %, to about 15 wt %, 20 wt %, 25 wt %, 30 wt %, or 40 wt % relative to the total weight of the composition.

As used herein, the term "composition" includes a fine fragrance composition intended for application to a body surface, such as for example, skin or hair, i.e., to impart a pleasant odor thereto, or cover a malodour thereof. They are generally in the form of perfume concentrates, perfumes, eau de parfums, eau de toilettes, aftershaves, colognes, body splashes, or body sprays. The fine fragrance compositions may be ethanol based compositions. The term "composition" may also include a cosmetic composition, which comprises a fragrance material for the purposes of delivering a pleasant smell to drive consumer acceptance of the cosmetic composition. The term "composition" may also include cleaning compositions, such as fabric care composition or home care compositions, including air care compositions, for use on clothing or other substrates such as hard surfaces (e.g., dishes, floors, countertops). Additional non-limiting examples of "composition" may also include facial or body powder, foundation, body/facial oil, mousse, creams (e.g., cold creams), waxes, sunscreens and blocks, bath and shower gels, lip balms, self-tanning compositions, masks and patches. Further non-limiting illustrative examples are described below.

As used herein, the term "consumer" means both the user of the composition and the observer nearby or around the user.

One aspect presented herein, provides a composition, wherein the composition comprises:
  a. ethanol, in an amount from 30 to 75 wt % relative to the total weight of the composition;
  b. a fragrance component present in an amount from 0.04 to 40 wt %, relative to the total weight of the composition,
    wherein the fragrance component comprises:
      i. a high volatility component an amount from 0.08 to 55 wt % of the fragrance component, comprising
        a. a first at least one perfume raw material having a first vapor pressure greater than 0.08 Torr at 22° C.; and optionally b. a second at least one perfume raw material having a first vapor pressure greater than 0.08 Torr at 22° C.;

ii. a medium volatility component in an amount from 0.08 to 85 wt % of the fragrance component, comprising:

a. a first at least one perfume raw material having a first vapor pressure range of 0.0008 to 0.08 Torr at 22° C.; and optionally b. a second at least one perfume raw material having a first vapor pressure range of 0.0008 to 0.08 Torr at 22° C.; and c. at least one modulator in an amount from 0.1 to 50 wt %, relative to the total weight of the composition;

wherein the first vapor pressure of the at least one first perfume raw material of the high volatility component is determined in the absence of the at least one modulator;

wherein the first vapor pressure of the at least one second perfume raw material of the high volatility component is determined in the absence of the at least one modulator;

wherein the at least one modulator changes the first vapor pressure of the at least one second perfume raw material of the high volatility component to a second vapor pressure;

wherein the second vapor pressure of the at least one second perfume raw material of the high volatility component is in the range of 0.0008 to 0.08 Torr at 22° C.;

wherein the first vapor pressure range of the at least one first perfume raw material of the medium volatility component is determined in the absence of the at least one modulator;

wherein the first vapor pressure range of the at least one second perfume raw material of the medium volatility component is determined in the absence of the at least one modulator;

wherein the at least one modulator changes the first vapor pressure range of the at least one second perfume raw material of the medium volatility component to a second vapor pressure; and wherein the second vapor pressure of the at least one second perfume raw material of the medium volatility component is less than 0.0008 Torr at 22° C.

In some aspects, the fragrance component present in an amount from 0.04 to 20 wt %, relative to the total weight of the composition.

In some aspects, the composition further comprises water, in an amount of less than or equal to 15 wt % relative to the total weight of the composition.

In some aspects, the composition further comprises water, in an amount 5 to 15 wt % relative to the total weight of the composition.

In some aspects, the composition further comprises water, in an amount 0 to 5 wt % relative to the total weight of the composition.

In another aspect, water may be present in any of the compositions presented, and more specifically, it shall not exceed about 15 wt %, alternatively about 14 wt % or less, alternatively about 13 wt % or less, alternatively about 12 wt % or less, alternatively about 11 wt % or less, alternatively about 10 wt % or less, alternatively about 9 wt % or less, alternatively about 8 wt % or less, alternatively about 7 wt % or less, alternatively about 6 wt % or less, alternatively about 5 wt % or less, alternatively about 4 wt % or less, alternatively about 3 wt % or less, alternatively about 2 wt % or less, alternatively about 1 wt % or less, relative to the total weight of the composition. Alternatively, water may be present in an amount of from about 10 wt or 20 wt to about 40 wt %, relative to the total weight of the composition. When the composition is a cosmetic composition the level of water should not be so high that the product becomes cloudy thus negatively impacting the product aesthetics. It is understood that the amount of water present in the composition may be from the water present in the ethanol used in the composition, as the case may be.

Compositions according to the aspects presented herein contain a fragrance component and at least one modulator. The fragrance component comprises:

i. a high volatility component, comprising at least one perfume raw material having a vapor pressure greater than 0.08 Torr at 22° C.; and ii. a medium volatility component, comprising at least one perfume raw material having a vapor pressure range of 0.0008 to 0.08 Torr at 22° C.

The fragrance component may also further comprise a low volatility component, comprising perfume raw materials having vapor pressure less than 0.0008 Torr at 22° C.

In some aspects, the effect of the at least one modulator on the fragrance profile, particularly the portion of the fragrance profile which is derived from volatile fragrance materials (i.e., top and middle notes), can be improved. By "improved" it is meant that the fragrance character of the composition, particular the components contributed by the volatile fragrance materials, can be perceived by the consumer at later time points such as, for example, 2 hours, 4 hours, 6 hours, 8 hours, 10 hours, and possibly all the way up to 24 hrs. after application as compared to controls, i.e., conventional compositions, or compositions wherein the fragrance component comprises: a high volatility component, comprising perfume raw materials having a vapor pressure greater than 0.08 Torr at 22° C.; and a medium volatility component, comprising perfume raw materials having a vapor pressure range of 0.0008 to 0.08 Torr at 22° C., lacking a modulator.

Alternatively, by "improved" it can mean that the perception of the components contributed by the volatile fragrance materials, by the consumer, is markedly increased or enhanced as compared to the controls. "Increased" or "enhanced" perception of the fragrance profile means that the consumer perceives the fragrance profile of a composition as not changing from its initial impression or the changes are minimal from when the composition was first applied to when it dissipates.

Alternatively, by "improved" it can mean that the perception of the components contributed by the volatile fragrance materials can be perceived by the consumer during dry-down.

Typically, it has been difficult to remove the water from perfume compositions, such as, for example, an eau de toilette, without negatively impacting the fragrance profile perceived by a user. Without intending to be limited to any particular theory, for any given perfume raw material in a perfume composition, the perfume raw material forms an equilibrium between a liquid phase and a vapor phase. The presence of water drives the equilibrium of the perfume raw material toward the vapor phase, and thus increases the concentration of the perfume raw material in the head-space. Removing the water, decreases the concentration of the perfume raw materials in the head-space, and therefore decreases the perception of the perfume raw material.

The concentration of the perfume raw material in the head-space may be greater for a highly volatile perfume raw material, compared to a less-volatile perfuming material. Additionally, the perception of the perfuming raw material may be greater for a perfuming raw material having a lower odor detection threshold, compared to a perfuming raw material having a higher odor detection threshold. However, the performance of the perfuming composition may be negatively impacted by the use of highly volatile and/or low odor detection threshold perfume raw materials to counteract the removal of water.

In some embodiments, the present application provides at least one modulator that allows the removal of water from perfume compositions without negatively impacting the performance of the perfuming compositions.

Selecting Perfume Raw Materials to Formulate the Fragrance Component of the Compositions According to the Aspects Presented Herein: In one aspect, the at least one modulator is selected according to its Hansen solubility parameters. Hansen solubility parameters may be used to predict if one material will dissolve in another and form a solution. A molecule is assigned three Hansen solubility parameters:

$\delta_d$: The energy from dispersion forces between molecules;
$\delta_p$: The energy from dipolar intermolecular force between molecules; and
$\delta_h$: The energy from hydrogen bonds between molecules.

Figure 2:
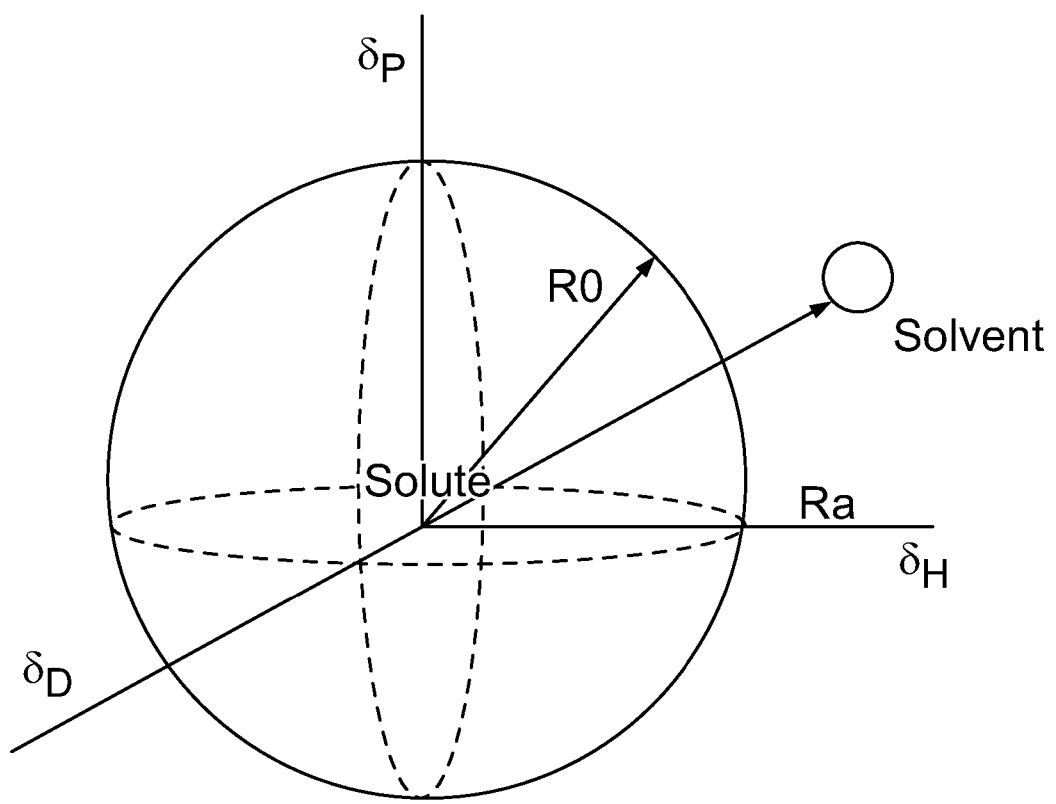
FIG. 2 shows a representation of the Hansen Space defined in three directions by the three Hansen solubility parameters, wherein $R_0$ is the radius of the sphere of solubility characteristic of the solute. $R_a$ represents the distance between the solute solubility parameter (center of the sphere of solubility) and the solvent solubility parameter.

Referring to FIG. 2, the Hansen solubility parameters can be treated as co-ordinates for a point in three dimensions also known as the Hansen space. Without intending to be limited to any particular theory, the nearer two molecules are in the Hansen space, the more likely they are to dissolve into each other.

For a fragrance mixture, the simplest way to calculate the Hansen solubility parameter (HSP) of the mixture is to assume an ideal mixing of the compounds:

$$HSP_{mix} = \Sigma_i \emptyset_i HSP_i, \quad \text{(Equation 1)}.$$

where $\emptyset_i$ are the volume fractions of the compounds.

The Hansen solubility parameter (HSP) can be calculated. The ratio RED (Relative Energy Difference) is defined as:

$$RED = \frac{R_a}{R_0}. \quad \text{(Equation 2)}$$

In some aspects, the ratio RED may be used to ascertain the affinity of the at least one modulator with a particular perfume raw material. In one aspect, the ratio RED of the at least one modulator is less than or equal to 1. Without intending to be limited to any particular theory, when the ratio RED is less than or equal to one, the particular perfume raw material is more likely to dissolve in the at least one modulator.

In one aspect, in addition to the at least one modulator having a ratio RED of less than or equal to 1, the at least one modulator has a low volatility, wherein the low volatility is sufficient to ensure the at least one modulator is present during the entire dry-down period of the perfuming composition. In one aspect, the at least one modulator has a vapor pressure of less than 0.0008 Torr at 22° C.

In one aspect, in addition to the at least one modulator having a ratio RED of less than or equal to 1, the at least one modulator has a minimal olfactive contribution. In one aspect, the olfactive contribution of the at least one modulator is defined by the odor detection threshold. In one aspect, the at least one modulator has a high odor detection threshold. As used herein, the term "odor detection threshold" refers to the lowest concentration of a perfume raw ingredient or modulator that is perceivable by the human sense of smell, expressed in μg/l.

In one aspect, the olfactive contribution of the at least one modulator is defined by the odor value. As used herein, the term "odor value", or "OV" refers to the quotient of the volatility (Vol) of an odorant in the saturated headspace and its threshold (ODT) concentration. The odor value is therefore defined as a dimensionless number given by:

$$OV = \frac{Vol}{ODT}. \quad \text{(Equation 3)}$$

In one aspect, the olfactive contribution of the at least one modulator is defined by the olfactive impact. As used herein, the term "olfactive impact", or "OI" refers to the quotient of the volatility (Vol) of an odorant in the saturated headspace and its threshold (ODT) concentration. The olfactive impact is therefore defined as a dimensionless number given by:

$$OI = \frac{Vol}{C_I} \quad \text{(Equation 4)}$$

in which the denominator corresponds to the concentration in headspace predicted to give an intensity of $I_i=2.5$ for all materials, referred to herein as "$C_I$", expressed as μg/l. In one aspect, $C_I$ is calculated as follows:

$$C_{Ii} = 10^{\left\{\theta - \left(\frac{1}{CP_i}\right) ln\left[\frac{I_{max}}{I_i} - 1\right]\right\}}. \quad \text{(Equation 5)}$$

The experimental points are fitted to a sigmoidal curve using a non-linear regression of the following form:

$$I = \frac{I_{Max}}{1 + \exp(-CP(\log(c_{headspace}) - Teta))}. \quad \text{(Equation 6)}$$

A sigmoidal curve is defined by three parameters: $I_{max}$ (the asymptotic value for the perceived intensity), Teta (the logarithmic value of gaseous concentration corresponding to the inflexion point of the curve) and the Curve Parameter, CP. A fourth parameter, the Slope, is related to the tangent value at the Teta concentration by the following equation:

$$Slope = \frac{CP \cdot I_{max}}{4}. \quad \text{(Equation 7)}$$

Figure 3:
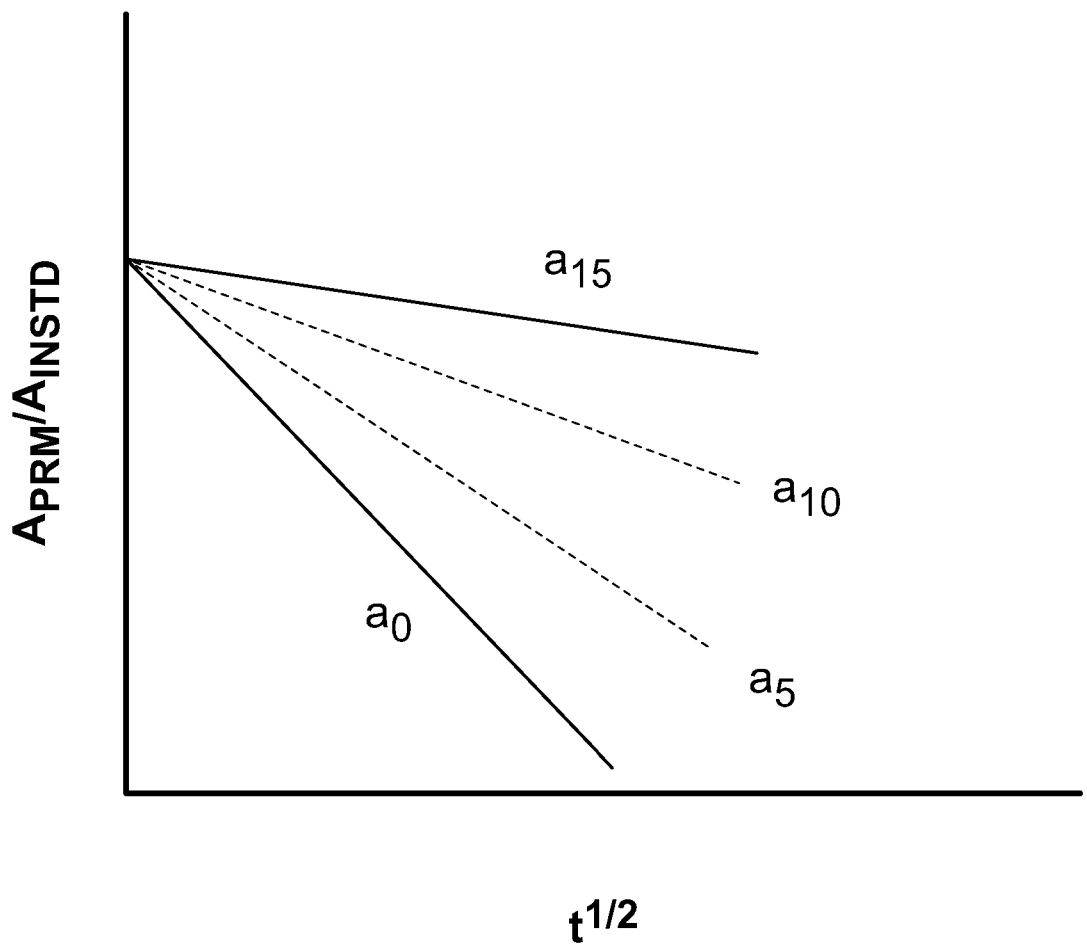
FIG. 3 provides shows the effect of the modulator on the amount of a perfume raw material in solution over time. The solid lines denote the ratio of actual recorded values of the amount of a perfume raw material ($A_{PRM}$) to by the amount of an internal standard ($A_{INSTD}$) in the presence of 15 wt % modulator, relative to the total weight of the composition ($a_{15}$), or without modulator ($a_0$). The dashed lines denote the predicted ratios in a solution containing either 5 wt % modulator, relative to the total weight of the composition ($a_5$), or 10 wt % modulator, relative to the total weight of the composition ($a_{10}$) over time.

Referring to FIG. 3, the amount of any given perfume raw material in solution does not remain constant. Rather, the perfume raw material diffuses into the headspace, and the concentration of the perfume raw material in solution declines with time. Without intending to be limited to any particular theory, a consumer will be able to detect and recognize the presence of the perfume raw material, once the concentration of the perfume raw material is above a threshold concentration (referred to herein as the odor recognition threshold).

In FIG. 3, the decline in concentration of the perfume raw material in solution is recorded as the ratio of actual recorded values of the amount of a perfume raw material ($A_{PRM}$) to by the amount of an internal standard ($A_{INSTD}$). In the absence of the at least one modulator, the rate of decrease of the concentration of the perfume raw material in solution has a first value (shown as the $a_0$ line on the graph, defined herein $d(A_{PRM}/A_{INSTD})/dt^{1/2}$). In some aspects, the presence of the at least one modulator changes the first value to a lower, second value. In the example shown in FIG. 3, the at least one modulator having a concentration of 15 wt %, relative to the total weight of the composition decreases $d(A_{PRM}/A_{INSTD})/dt^{1/2}$ to a second value (shown as the $a_{15}$ line on the graph). Accordingly, the presence of the at least one modulator may delay the time at which a consumer may be able to detect and recognize the presence of the perfume raw material. Alternatively, the presence of the at least one modulator may prolong the duration that the consumer may be able to detect and recognize the presence of the perfume raw material. Alternatively, the presence of the at least one modulator may prevent a consumer from being able to detect and recognize the presence of the perfume raw material.

The extent by which the at least one modulator influences $d(A_{PRM}/A_{INSTD})/dt^{1/2}$ is dependent on a variety of factors, such as, for example, the concentration of the at least one modulator, the composition of the at least one modulator, the volatility of the perfume raw material in the modulator, and the like.

In some aspects, the extent by which the at least one modulator influences $d(A_{PRM}/A_{INSTD})/dt^{1/2}$ at any modulator concentration (x % w/w) is determined by comparing the decrease in the ratio of $A_{PRM}/A_{INSTD}$ in the presence of a known concentration of the at least one modulator (such as, for example 15% w/w) over the square root of time, with the decrease in the ratio of $A_{PRM}/A_{INSTD}$ at second known concentration of the at least one modulator, such as, for example 0% w/w, over the square root of time.

In some aspects, the extent by which the at least one modulator influences $d(A_{PRM}/A_{INSTD})/dt^{1/2}$ at any modulator concentration ($a_x$) is determined by comparing $d(A_{PRM}/A_{INSTD})/dt^{1/2}$ in the presence of a known concentration of the at least one modulator (such as, for example 15% w/w–$a_{15}$), with $d(A_{PRM}/A_{INSTD})/dt^{1/2}$ at second known concentration of the at least one modulator, such as, for example 0% w/w ($a_0$).

In some aspects, $a_{15}$ and $a_0$ are used to calculate $a_x$, using the following equation:

$$a_x = a_{15} + (a_0 - a_{15})(15-x)/(15-0) \quad \text{(Equation 8)}.$$

In some instances $a_{15}$, $a_{10}$, $a_5$, or $a_0$ may be used to predict the amount of the perfume raw material present in solution at a given time.

In another aspect, the square of the ratio of $a_x/a_0$ may be used to calculate the second vapor pressure of the perfume raw material in the presence of the at least one modulator at x wt %.

For example, by way of illustration, using the at least one modulator at a concentration of 15 wt %, relative to the total weight of the composition, the vapor pressure of the perfume raw material in the presence of the at least one modulator (referred to herein as the second vapor pressure of the perfume raw material) may be calculated as follows:

$$(a_{15}/a_0)^{2*} P_{vap} = P^*_{vap}. \quad \text{(Equation 9)}.$$

wherein:
$P_{vap}$ = the first vapor pressure of the perfume raw material
$P^*_{vap}$ = the second vapor pressure of the perfume raw material Accordingly, the present disclosure provides a method to predict how the at least one modulator may delay the time at which a consumer may be able to detect and recognize the presence of the perfume raw material. Alternatively, the present disclosure provides a method to predict how the at least one modulator may prolong the duration that the consumer may be able to detect and recognize the presence of the perfume raw material. Alternatively, the present disclosure provides a method to predict how the at least one modulator may prevent a consumer from being able to detect and recognize the presence of the perfume raw material. Without intending to be limited to any particular theory, the second vapor pressure of the perfume raw material may be a factor which may predict how a modulator may alter the consumer's perception of the perfume raw material in the manner described above.

Accordingly, the present disclosure provides a method to calculate the second vapor pressure of a given perfume raw material in the presence of the at least one modulator at a given concentration.

Accordingly, the present disclosure provides a method to ascertain, for any modulator and/or any concentration of modulator, the second vapor pressure for a perfume raw material. Moreover, based on the second vapor pressure, the present disclosure provides a method to classify, based on the particular modulator, and the concentration of the modulator, a palette of perfume raw ingredients according to whether, in the presence of the at least one modulator, the particular perfume raw material either:

i. remains available for selection for use in the high volatility component, wherein the second vapor pressure of the perfume raw material is greater than 0.08 Torr at 22° C. (examples of suitable perfume raw materials are shown in Table 1);

ii. no longer remains available for selection for use in the high volatility component, but becomes available for selection for use in the medium volatility component, wherein the second vapor pressure of the perfume raw material has a range of 0.0008 to 0.08 Torr at 22° C. (examples of suitable perfume raw materials are shown in Table 2);

iii. remains available for selection for use in the medium volatility component, wherein the second vapor pressure of the perfume raw has a range of 0.0008 to 0.08 Torr at 22° C. (examples of suitable perfume raw materials are shown in Table 3;

iv. no longer remains available for selection for use in the medium volatility component, but becomes available for selection for use in the low volatility component, wherein the second vapor pressure of the perfume raw material is less than 0.0008 Torr at 22° C. (examples of suitable perfume raw materials are shown in Table 4); or v. remains available for selection for use in the low volatility component, wherein the second vapor pressure of the perfume raw is less than 0.0008 Torr at 22° C. (examples of suitable perfume raw materials are shown in Table 5);

In some aspects, a perfume raw material may no longer remain available for selection for use in the medium volatility component because the perfume raw material may become suppressed (i.e. not perceived by the consumer) in the presence of the modulator. Examples of suitable perfume raw materials are shown in Table 6.

In some aspects, a perfume raw material remains available for selection for use in the low volatility component the perfume raw material may become suppressed (i.e. not perceived by the consumer) in the presence of the modulator. Examples of suitable perfume raw materials are shown in Table 7.

Additional examples of classified suitable perfume raw materials maybe found in Examples 1and 2, and the tables listed therein. Referring to Examples 1 and 2, in some aspects, the particular modulator may affect the classification of the particular perfume raw material.

In some aspects, the method to calculate the second vapor pressure of a given perfume raw material in the presence of a particular the at least one modulator at a given concentration comprises the steps of:

a. determining $A_{PRM}/A_{INSTD}$ for the perfume raw material in solution, in the absence of the at least one modulator ($A_0$) over time;

b. determining $A_{PRM}/A_{INSTD}$ the perfume raw material in solution, in the presence of the at least one modulator at known concentration of modulator ($A_x$) over time;

c. determining the vapor pressure of the perfume raw material in solution, in the absence of the at least one modulator ($P_{vap}$); and d. calculating, based on $A_0$, $A_x$, $a_0$ and $a_x$; and e. calculating, based on $a_0$, $a_x$, and $P_{vap}$, the second vapor pressure for the perfume raw material in solution, in the presence of the modulator at known concentration of the at least one modulator ($P^*_{vap}$).

In some aspects, the calculated second vapor pressure allows a perfumer to formulate a fragrance profile with an accord, such as, for example, a floral, or a fruity, or an aromatic, or a spicy, or an oriental accord characteristic of the middle notes, which can last for very long periods, especially throughout the life of the composition after its application, without giving way to the stronger odors of the base notes. Moreover, in some aspects, the calculated second vapor pressure allows a perfumer to utilize modulators in a manner that does not affect the consumer's initial perception of a fragrance profile: For example, a perfumer may select, based on a perfume raw materials calculated second vapor pressure, a top note that does not decrease in volatility in the presence of a modulator at a particular concentration.

In some aspects, the calculated second vapor pressure allows a perfumer to modify a fragrance profile and/or intensity of an existing composition formulated as a first consumer product to have the same fragrance profile and/or intensity when the existing composition is formulated as a second consumer product. For example, by way of illustration, a composition may be incorporated into a fine fragrance and the methods presented herein may allow a perfumer to reproduce the same fragrance profile and/or intensity of the fine fragrance in a soap, cream, household cleaner, and the like.

Figure 4:
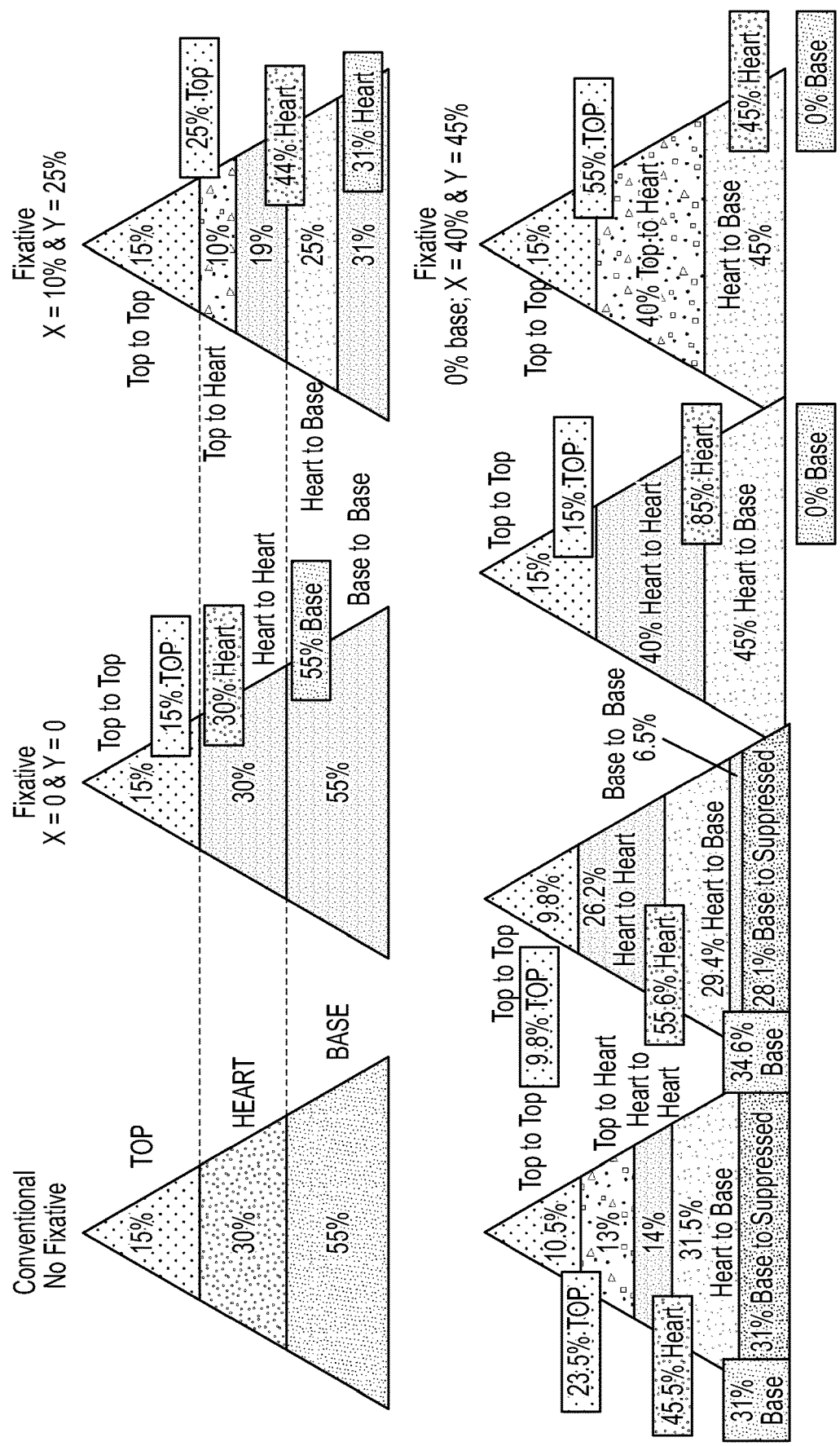
FIG. 4 provides a graphical representation of perfume structures according to several aspects presented herein.
Figure 5:
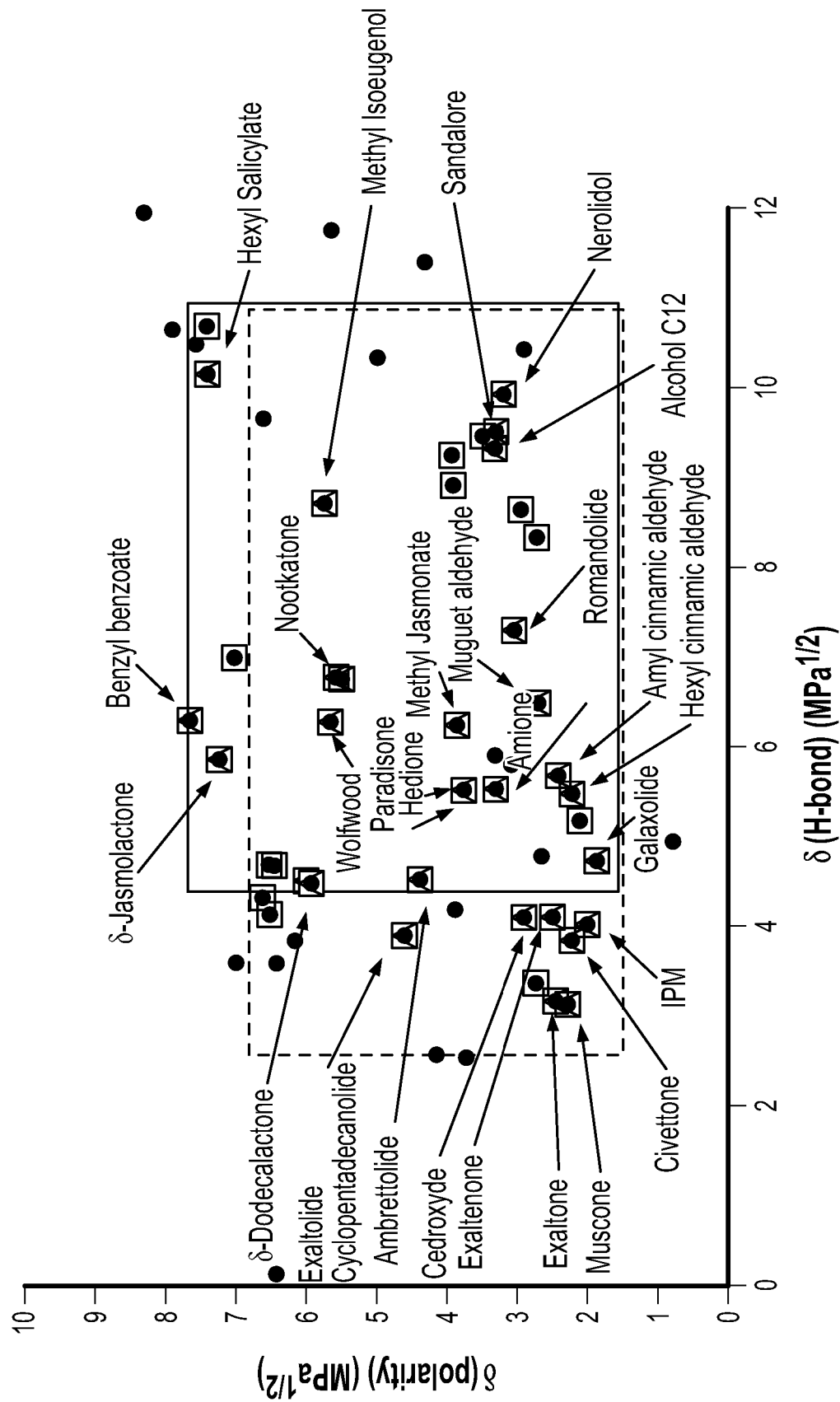
FIG. 5 shows compounds suitable for use as the at least one modulator according to some aspects described herein.

Formulation of the Fragrance Component: Referring to FIG. 4, the present disclosure provides a method to construct various compositions utilizing perfume raw ingredients from a palette of raw ingredients that have as been classified according to whether particular perfume raw material either:

i. remains available for selection for use in the high volatility component, wherein the second vapor pressure of the perfume raw material is greater than 0.08 Torr at 22° C. (examples of suitable perfume raw materials are shown in Table 1);

ii. no longer remains available for selection for use in the high volatility component, but becomes available for selection for use in the medium volatility component, wherein the second vapor pressure of the perfume raw material has a range of 0.0008 to 0.08 Torr at 22° C. (examples of suitable perfume raw materials are shown in Table 2);

iii. remains available for selection for use in the medium volatility component, wherein the second vapor pressure of the perfume raw has a range of 0.0008 to 0.08 Torr at 22° C. (examples of suitable perfume raw materials are shown in Table 3;

iv. no longer remains available for selection for use in the medium volatility component, but becomes available for selection for use in the low volatility component, wherein the second vapor pressure of the perfume raw material is less than 0.0008 Torr at 22° C. (examples of suitable perfume raw materials are shown in Table 4); or v. remains available for selection for use in the low volatility component, wherein the second vapor pressure of the perfume raw is less than 0.0008 Torr at 22° C. (examples of suitable perfume raw materials are shown in Table 5);

In some aspects, a perfume raw material may no longer remain available for selection for use in the medium volatility component because the perfume raw material may become suppressed (i.e. not perceived by the consumer) in the presence of the modulator. Examples of suitable perfume raw materials are shown in Table 6.

In some aspects, a perfume raw material remains available for selection for use in the low volatility component the perfume raw material may become suppressed (i.e. not perceived by the consumer) in the presence of the modulator. Examples of suitable perfume raw materials are shown in Example 1 and Table 7.

Additional examples of classified suitable perfume raw materials maybe found in Examples 1and 2, and the tables listed therein. Referring to Examples 1 and 2, in some aspects, the particular modulator may affect the classification of the particular perfume raw material.

Such a solution as presented herein provides enhanced longevity of the fragrance profile, particularly amongst those compositions formulated from volatile fragrance materials having medium to high vapor pressure ranges, without having to rely on the presence or significant amounts of the low volatile fragrance materials, which has a tendency to overpower and alter the overall character of a fragrance. This provides the perfumer options to formulate accords having new fragrance profiles.

TABLE 1

Examples of perfume raw materials that remain available for selection for use in the high volatility component, wherein the second vapor pressure of the perfume raw material is greater than greater than 0.08 Torr at 22° C.

| COMMON NAME | IUPAC NAME |
|---|---|
| ETHYL BUTYRATE | Butanoic acid, ethyl ester |
| BUTYL ACETATE | Acetic acid, butyl ester |
| AMYL ACETATE | 3-Methylbutyl acetate |
| N 302 | (2E)-2-Hexenal |
| ACETATE DE PRENYLE | 3-Methyl-2-buten-1-yl acetate |
| PINENE MELANGE | (1R,5R)-6,6-Dimethyl-2-methylenebicyclo[3.1.1]heptane |
| ETHYL 2-METHYLPENTANOATE (APPLINATE) | Ethyl (2R)-2-methylpentanoate |
| CAPROATE D'ETHYLE | Ethyl hexanoate |
| EUCALYPTOL | 1,3,3-Trimethyl-2-oxabicyclo[2.2.2]octane |

TABLE 1-continued

Examples of perfume raw materials that remain available for selection for use in the high volatility component, wherein the second vapor pressure of the perfume raw material is greater than greater than 0.08 Torr at 22° C.

| COMMON NAME | IUPAC NAME |
|---|---|
| IFFOCIMENE | (3E)-3,7-Dimethyl-1,3,6-octatriene |
| LIMONENE 1 X DIST FAB | (4R)-4-Isopropenyl-1-methylcyclohexene |
| HEXYL ACETATE | Hexyl acetate |
| PIPOL ACETATE | (3Z)-3-Hexen-1-yl acetate |
| BUTYRATE D'AMYLE | 3-Methylbutyl butyrate |
| PIPOL DIST | (3Z)-3-Hexen-1-ol |
| ALDEHYDE BENZOIQUE | Benzaldehyde |
| ACETOACETATE D'ETHYLE | Ethyl 3-oxobutanoate |
| LIFFAROME | (3Z)-3-Hexen-1-yl methyl carbonate |
| ALLYL CAPROATE | Allyl hexanoate |
| PHENYLACETALDEHYDE-DIMETHYLACETAL (VERT DE LILAS) | (2,2-Dimethoxyethyl)benzene |
| ROSE OXIDE | (2R,4R)-4-Methyl-2-(2-methyl-1-propen-1-yl)tetrahydro-2H-pyran |
| BENZOATE DE METHYLE | Methyl benzoate |
| GALBANOLENE SUPER | (3E,5Z)-1,3,5-Undecatriene |
| METHYL PAMPLEMOUSSE | 6,6-Dimethoxy-2,5,5-trimethyl-2-hexene |
| BENZYL ACETATE EXTRA | Benzyl acetate |
| HCM | Methyl 2-octynoate |

TABLE 2

Examples of perfume raw materials that no longer remain available for selection for use in the high volatility component, but become available for selection for use in the medium volatility component, wherein the second vapor pressure of the perfume raw material has a range of 0.0008 to 0.08 Torr at 22° C.

| COMMON NAME | IUPAC NAME |
|---|---|
| ALDEHYDE MNA | (2R)-2-Methylundecanal |
| MELONAL | (2R)-2,6-Dimethyl-5-heptenal |
| ZESTOVER | (1RS,2RS)-2,4-dimethyl-3-cyclohexene-1-carbaldehyde (A) (1RS,2SR)-2,4-dimethyl-3-cyclohexene-1-carbaldehyde (B) |
| ALDEHYDE C 9 | Nonanal |
| TRANS DECENAL | (4E)-4-Decenal |
| DIMETOL | 2,6-Dimethyl-2-heptanol |
| PELARGODIENAL | (2E,6Z)-2,6-Nonadienal |
| MENTHONE PURIFIEE | 2-Isopropyl-5-methylcyclohexanone |
| CAMPHRE | (1R,4R)-1,7,7-Trimethylbicyclo[2.2.1]heptan-2-one |
| Fructone | Ethyl (2-methyl-1,3-dioxolan-2-yl)acetat |
| CITRONELLAL | (3R)-3,7-Dimethyl-6-octenal |
| PK EXTRA | p-Cresol |
| ESTRAGOLE | 1-Allyl-4-methoxybenzene |
| ALDEHYDE C 10 | Decanal |
| Styrallyl acetate | (1R)-1-Phenylethyl acetate |
| VIOLETTYNE 10 MIP | (3E)-1,3-Undecadien-5-yne |
| PIPOL ISOBUTYRATE | (3Z)-3-Hexen-1-yl 2-methylpropanoate |
| FIRASCONE | methyl (1RS,2SR)-2,6,6-trimethyl-3-cyclohexene-1-carboxylate (A) methyl (1RS,2RS)-2,6,6-trimethyl-3-cyclohexene-1-carboxylate (B) |
| BENZOATE D'ETHYLE | ethyl benzoate |
| DIHYDROMYRCENOL PURE | (6R)-2,6-Dimethyl-7-octen-2-ol |
| ALLYL HEPTANOATE | Allyl heptanoate |
| Benzyl alcohol | Phenylmethanol |
| ROMASCONE | Methyl (1R)-2,2-dimethyl-6-methylenecyclohexanecarboxylate |
| BUTYRATE DE PIPOL | (3Z)-3-Hexen-1-yl butyrate |
| SAFRANAL | 2,6,6-Trimethyl-1,3-cyclohexadiene-1-carbaldehyde |
| DELPHONE | (2R)-2-Pentylcyclopentanone |

TABLE 2-continued

Examples of perfume raw materials that no longer remain available for selection for use in the high volatility component, but become available for selection for use in the medium volatility component, wherein the second vapor pressure of the perfume raw material has a range of 0.0008 to 0.08 Torr at 22° C.

| COMMON NAME | IUPAC NAME |
|---|---|
| PHENYLACETATE DE METHYLE | Methyl phenylacetate |
| OXANE | (2R,4S)-2-Methyl-4-propyl-1,3-oxathiane |
| LINALYL ACETATE AR | (3R)-3,7-Dimethyl-1,6-octadien-3-yl acetate |
| ACETATE DE LINALYLE BJ | (3R)-3,7-Dimethyl-1,6-octadien-3-yl acetate |
| TETRALINOL PUR | (3R)-3,7-Dimethyl-3-octanol |
| PROPIONATE DE BENZYLE | Benzyl propionate |
| Verdox | (1R,2R)-2-(2-Methyl-2-propanyl)cyclohexyl acetate |
| DORISYL | trans-4-(2-Methyl-2-propanyl)cyclohexyl acetate |
| CARBINOL MUGUET | 2-Methyl-4-phenyl-2-butanol |
| ISOBORNYL ACETATE | (1R,2R)-1,7,7-TRIMETHYL-BICYCLO[2.2.1]HEPT-2-YL ACETATE |
| ETHYL PHENYL ACETATE | Ethyl phenylacetate |
| ALDEHYDE C 11 LIQUE | Undecanal |

TABLE 3

Examples of perfume raw materials remain available for selection for use in the medium volatility component, wherein the second vapor pressure of the perfume raw has a range of 0.0008 to 0.08 Torr at 22° C.

| COMMON NAME | IUPAC NAME |
|---|---|
| NONENOL | (6Z)-6-Nonen-1-ol |
| PHENYL ETHYL ALCOHOL | 2-Phenylethanol |
| CITRAL TOTAL | (2E)-3,7-Dimethyl-2,6-octadienal |
| SALICYLATE DE METHYLE | methyl 2-hydroxybenzoate |
| ANETHOLE | 1-Methoxy-4-[(1E)-1-propen-1-yl]benzene |
| CARVONE GAUCHE | (5R)-5-Isopropenyl-2-methyl-2-cyclohexen-1-one |
| MOC | 2-Nonynoic acid, methyl ester |
| 2-PHENYL ETHYL ACETATE | 2-Phenylethyl acetate |
| BENZYLACETONE PUR | 4-Phenyl-2-butanone |
| BASE XXI | (2E,6Z)-2,6-Nonadien-1-ol |
| 2-PHENYLETHYL FORMATE | 2-Phenylethyl formate |
| STEMONE | (+−)-(3E)-5-methyl-3-heptanone oxime (A) (+−)-(3Z)-5-methyl-3-heptanone oxime (B) |
| OCTALACTONE G | 5-Butyldihydro-2(3H)-furanone |
| ALLYL AMYL GLYCOLATE | Allyl (3-methylbutoxy)acetate |
| Terpenyl acetate | 2-(4-Methyl-3-cyclohexen-1-yl)-2-propanyl acetate |
| ACETATE DE TERPENYLE EXTRA | 2-[(1R)-4-Methyl-3-cyclohexen-1-yl]-2-propanyl acetate |
| KOAVONE | (+−)-3,5,6,6-tetramethyl-4-methylidene-2-heptanone (A) (+−)-(4E)-3,4,5,6,6-pentamethyl-4-hepten-2-one (B) (+−)-(3Z)-3,4,5,6,6-pentamethyl-3-hepten-2-one (C) (+−)-(3E)-3,4,5,6,6-pentamethyl-3-hepten-2-one (D) |
| ALDEHYDE C 11 LENIQUE | 10-Undecenal |
| DIMETHYLOCTANOL | (3R)-3,7-Dimethyl-1-octanol |

TABLE 3-continued

Examples of perfume raw materials remain available for selection for use in the medium volatility component, wherein the second vapor pressure of the perfume raw has a range of 0.0008 to 0.08 Torr at 22° C.

| COMMON NAME | IUPAC NAME |
|---|---|
| ALDEHYDE C 12 | Lauraldehyde |
| MENTHOL NAT | (1R,2S,5R)-2-Isopropyl-5-methylcyclohexanol |
| TIGLATE DE PIPOL | (3Z)-3-Hexen-1-yl (2E)-2-methyl-2-butenoate |
| INDOLE | 1H-Indole |
| Terpineol ord | (+−)-ALPHA-TERPINEOL |
| Alpha terpineol | (+−)-ALPHA-TERPINEOL |
| ALCOOL PHENYLPROPYLIQUE | 3-Phenyl-1-propanol |
| DAMASCENATE D'ETHYLE | ETHYL 2,6,6-TRIMETHYL-1,3-CYCLOHEXADIENE-1-CARBOXYLATE |
| ALDEHYDE CINNAMIQUE | (2E)-3-Phenylacrylaldehyde |
| VELOUTONE | 2,2,5-Trimethyl-5-pentylcyclopentanone |
| Neryl acetate | (2Z)-3,7-dimethyl-2,6-octadien-1-yl acetate |
| ACETATE DE GERANYLE SYNTH FC | Geranyl acetate |
| Geranyl acetate | Geranyl acetate |
| Indocolore | 1-Phenylvinyl acetate |
| ALDEHYDE ANISIQUE SPECIAL REDIST | 4-Methoxybenzaldehyde |
| CITRONELLYL NITRILE | (3R)-3,7-Dimethyl-6-octenenitrile |
| ISOSPIRENE TOTAL | 2,6,9,10-Tetramethyl-1-oxaspiro[4.5]deca-3,6-diene |
| CORANOL | 4-Cyclohexyl-2-methyl-2-butanol |
| FLORHYDRAL | (3R)-3-(3-Isopropylphenyl)butanal |
| SCLAREOLATE | Propyl (2S)-2-[(2-methyl-2-butanyl)oxy]propanoate |
| PAMPLEWOOD | 3-Methoxy-7,7-dimethyl-10-methylenebicyclo[4.3.1]decane |
| METHYLANTHRANILATE DE METHYLE | Methyl 2-(methylamino)benzoate |
| CITRONELLOL | (3R)-3,7-Dimethyl-6-octen-1-ol |
| ANTHRANILATE DE METHYLE DIST | Methyl 2-aminobenzoate |
| ACETATE DE CARBINOL BDM | 2-Methyl-1-phenyl-2-propanyl acetate |
| Citronellyl acetate | (3R)-3,7-Dimethyl-6-octen-1-yl acetate |
| ACETATE DE VERDYLE | Tricyclo[5.2.1.02,6]dec-3-en-8-yl acetate |
| Cedramber | 8-Methoxycedrane |
| HEXENYL HEXENOATE (WILLIAMS ESTER) | (3Z)-3-Hexen-1-yl (3Z)-3-hexenoate |
| METHYLISOEUGENOL | 1,2-Dimethoxy-4-[(1E)-1-propen-1-yl]benzene |
| HELIOTROPINE ORD | 1,3-Benzodioxole-5-carbaldehyde |
| Delta damascone | (2E)-1-[(1S,2S)-2,6,6-Trimethyl-1-cyclohexen-1-yl]-2-buten-1-one |
| FOLIAVER | (2R)-3-(4-Methoxyphenyl)-2-methylpropanal |
| ISOBUTYRATE DE PHENYLETHYLE | 2-Phenylethyl 2-methylpropanoate |
| CAPROATE D'HEXYLE | Hexyl hexanoate |
| ACETATE DE CINNAMYLE | (2E)-3-Phenyl-2-propen-1-yl acetate |
| Bourgeonal | 3-[4-(2-Methyl-2-propanyl)phenyl]propanal |
| Cyclohexylpropionate d'allyle | 2-Propen-1-yl cyclohexanepropionate |
| Cyclosal | (2R)-3-(4-Isopropylphenyl)-2-methylpropanal |
| Gamma nonalactone | 5-Pentyldihydro-2(3H)-furanone |
| DAMAROSE ALPHA | (2E)-1-[(1R)-2,6,6-Trimethyl-2-cyclohexen-1-yl]-2-buten-1-one |
| DECALACTONE | 5-Hexyldihydro-2(3H)-furanone |
| NEOBUTENONE ALPHA | 1-(5,5-dimethyl-1-cyclohexen-1-yl)-4-penten-1-one |
| SULFOX 1 DIPG | (2R,5R)-5-Methyl-2-(2-sulfanyl-2-propanyl)cyclohexanone |
| ACROPAL | 3-(4-Methyl-3-penten-1-yl)-3-cyclohexene-1-carbaldehyde |
| MPGE | Ethyl 3-methyl-3-phenyl-2-oxiranecarboxylate |
| ETHYL LINALLOL | (3R,6E)-3,7-Dimethyl-1,6-nonadien-3-ol |
| PROPIONATE DE VERDYLE | TRICYCLO[5.2.1.0(2,6)]DEC-3-EN-8-YL PROPANOATE (A) TRICYCLO[5.2.1.0(2,6)]DEC-4-EN-8-YL PROPANOATE (B) |
| NUSSOL EXTRA | 2-Hydroxy-3-methyl-2-cyclopenten-1-one |
| SCENTENAL | 8(9)-METHOXY-TRICYCLO[5.2.1.0(2,6)]DECANE-3(4)-CARBALDEHYDE |
| PRECYCLEMONE B | 1-Methyl-4-(4-methyl-3-penten-1-yl)-3-cyclohexene-1-carbaldehyde |
| JASMINLACTONE | (6R)-6-[(2Z)-2-Penten-1-yl]tetrahydro-2H-pyran-2-one |
| CYCLOGALBANATE | Allyl cyclohexyloxyacetate |
| ISORALDEINE 70 P | (1E)-1-[(1R)-2,6,6-Trimethyl-2-cyclohexen-1-yl]-1-penten-3-one |
| LILYFLORE | (2,5-Dimethyl-2,3-dihydro-1H-inden-2-yl)methanol |
| Javanol | (1'S,3'R)-{1-METHYL-2-[(1',2',2'-TRIMETHYLBICYCLO[3.1.0]HEX-3'-YL)METHYL]CYCLOPROPYL]METHANOL |
| Ethylvanilline | 3-Ethoxy-4-hydroxybenzaldehyde |

TABLE 4

Examples of perfume raw materials that no longer remain available for selection for use in the medium volatility component, but become available for selection for use in the low volatility component, wherein the second vapor pressure of the perfume raw material is less than 0.0008 Torr at 22° C.

| COMMON NAME | IUPAC NAME |
|---|---|
| NONENOL | (6Z)-6-Nonen-1-ol |
| PHENYL ETHYL ALCOHOL | 2-Phenylethanol |
| CITRAL TOTAL | (2E)-3,7-Dimethyl-2,6-octadienal |
| SALICYLATE DE METHYLE | methyl 2-hydroxybenzoate |
| ANETHOLE | 1-Methoxy-4-[(1E)-1-propen-1-yl]benzene |
| CARVONE GAUCHE | (5R)-5-Isopropenyl-2-methyl-2-cyclohexen-1-one |
| MOC | 2-Nonynoic acid, methyl ester |
| 2-PHENYL ETHYL ACETATE | 2-Phenylethyl acetate |
| BENZYLACETONE PUR BASE XXI | 4-Phenyl-2-butanone (2E,6Z)-2,6-Nonadien-1-ol |
| 2-PHENYLETHYL FORMATE | 2-Phenylethyl formate |
| STEMONE | (+−)-(3E)-5-methyl-3-heptanone oxime (A) (+−)-(3Z)-5-methyl-3-heptanone oxime (B) |
| OCTALACTONE G | 5-Butyldihydro-2(3H)-furanone |
| ALLYL AMYL GLYCOLATE | Allyl (3-methylbutoxy)acetate |
| Terpenyl acetate | 2-(4-Methyl-3-cyclohexen-1-yl)-2-propanyl acetate |
| ACETATE DE TERPENYLE EXTRA | 2-[(1R)-4-Methyl-3-cyclohexen-1-yl]-2-propanyl acetate |
| KOAVONE | (+−)-3,5,6,6-tetramethyl-4-methylidene-2-heptanone (A) |

TABLE 4-continued

Examples of perfume raw materials that no longer remain available for selection for use in the medium volatility component, but become available for selection for use in the low volatility component, wherein the second vapor pressure of the perfume raw material is less than 0.0008 Torr at 22° C.

| COMMON NAME | IUPAC NAME |
|---|---|
|  | (+−)-(4E)-3,4,5,6,6-pentamethyl-4-hepten-2-one (B) |
|  | (+−)-(3Z)-3,4,5,6,6-pentamethyl-3-hepten-2-one (C) |
|  | (+−)-(3E)-3,4,5,6,6-pentamethyl-3-hepten-2-one (D) |
| ALDEHYDE C 11 LENIQUE | 10-Undecenal |
| DIMETHYLOCTANOL | (3R)-3,7-Dimethyl-1-octanol |
| ALDEHYDE C 12 | Lauraldehyde |
| MENTHOL NAT | (1R,2S,5R)-2-Isopropyl-5-methylcyclohexanol |
| TIGLATE DE PIPOL | (3Z)-3-Hexen-1-yl (2E)-2-methyl-2-butenoate |
| INDOLE | 1H-Indole |
| Terpineol ord | (+−)-ALPHA-TERPINEOL |
| Alpha terpineol | (+−)-ALPHA-TERPINEOL |
| ALCOOL PHENYLPROPYLIQUE | 3-Phenyl-1-propanol |
| DAMASCENATE D'ETHYLE | ETHYL 2,6,6-TRIMETHYL-1,3-CYCLOHEXADIENE-1-CARBOXYLATE |
| ALDEHYDE CINNAMIQUE | (2E)-3-Phenylacrylaldehyde |
| VELOUTONE | 2,2,5-Trimethyl-5-pentylcyclopentanone |
| Neryl acetate | (2Z)-3,7-dimethyl-2,6-octadien-1-yl acetate |
| ACETATE DE GERANYLE SYNTH FC | Geranyl acetate |
| Geranyl acetate | Geranyl acetate |
| Indocolore | 1-Phenylvinyl acetate |
| ALDEHYDE ANISIQUE SPECIAL REDIST | 4-Methoxybenzaldehyde |
| CITRONELLYL NITRILE | (3R)-3,7-Dimethyl-6-octenenitrile |
| ISOSPIRENE TOTAL | 2,6,9,10-Tetramethyl-1-oxaspiro[4.5]deca-3,6-diene |
| CORANOL | 4-Cyclohexyl-2-methyl-2-butanol |
| FLORHYDRAL | (3R)-3-(3-Isopropylphenyl)butanal |
| SCLAREOLATE | Propyl (2S)-2-[(2-methyl-2-butanyl)oxy]propanoate |
| PAMPLEWOOD | 3-Methoxy-7,7-dimethyl-10-methylenebicyclo[4.3.1]decane |
| METHYLANTHRANILATE DE METHYLE | Methyl 2-(methylamino)benzoate |
| CITRONELLOL | (3R)-3,7-Dimethyl-6-octen-1-ol |
| ANTHRANILATE DE METHYLE DIST | Methyl 2-aminobenzoate |
| ACETATE DE CARBINOL BDM | 2-Methyl-1-phenyl-2-propanyl acetate |
| Citronellyl acetate | (3R)-3,7-Dimethyl-6-octen-1-yl acetate |
| ACETATE DE VERDYLE | Tricyclo[5.2.1.02,6]dec-3-en-8-yl acetate |
| Cedramber | 8-Methoxycedrane |
| HEXENYL HEXENOATE (WILLIAMS ESTER) | (3Z)-3-Hexen-1-yl (3Z)-3-hexenoate |
| METHYLISOEUGENOL | 1,2-Dimethoxy-4-[(1E)-1-propen-1-yl]benzene |
| HELIOTROPINE ORD | 1,3-Benzodioxole-5-carbaldehyde |
| Delta damascone | (2E)-1-[(1S,2S)-2,6,6-Trimethyl-3-cyclohexen-1-yl]-2-buten-1-one |
| FOLIAVER | (2R)-3-(4-Methoxyphenyl)-2-methylpropanal |
| ISOBUTYRATE DE PHENYLETHYLE | 2-Phenylethyl 2-methylpropanoate |
| CAPROATE D'HEXYLE | Hexyl hexanoate |

TABLE 5

Examples of perfume raw materials that remain available for selection for use in the low volatility component, wherein the second vapor pressure of the perfume raw is less than 0.0008 Torr at 22° C.

| COMMON NAME | IUPAC NAME |
|---|---|
| PARADISONE | Methyl [(1R,2S)-3-oxo-2-pentylcyclopentyl]acetate |
| Hedione | Methyl [(1S,2S)-3-oxo-2-pentylcyclopentyl]acetate |
| MUSC DTI | 1-[1,1-Dimethyl-6-(2-methyl-2-propanyl)-2,3-dihydro-1H-inden-4-yl]ethanon |
| Aldehyde hexylcinnamique | (2E)-2-Benzylideneoctanal |
| SANDALORE | 3-Methyl-5-(2,2,3-trimethyl-3-cyclopenten-1-yl)-2-pentanol |
| Iso E (or Derambrene) | 1-(2,3,8,8-Tetramethyl-1,2,3,5,6,7,8,8a-octahydro-2-naphthalenyl)ethanone |
| DERAMBRENE | 1-(2,3,8,8-Tetramethyl-1,2,3,5,6,7,8,8a-octahydro-2-naphthalenyl)ethanone |
| AMIONE | (1E)-1-(2,6,6-Trimethyl-2-cyclohexen-1-yl)-1,6-heptadien-3-one |
| Norlimbanol | 1-(2,2,6-Trimethylcyclohexyl)-3-hexanol |
| AMBRINOL | 2,5,5-Trimethyl-1,2,3,4,4a,5,6,7-octahydro-2-naphthalenol |
| Galaxolide 70 BB | (4R,7S)-4,6,6,7,8,8-Hexamethyl-1,3,4,6,7,8-hexahydrocyclopenta[g]isochromene |
| CORPS PRALINE | 3-Hydroxy-2-methyl-4H-pyran-4-one |
| DARTANOL | (2E)-2-Ethyl-4-[(1R)-2,2,3-trimethyl-3-cyclopenten-1-yl]-2-buten-1-ol |
| TRANSLUZONE | 7-(2-Methyl-2-propanyl)-2H-1,5-benzodioxepin-3(4H)-one |
| EBANOL | (E)-3-METHYL-5-(2,2,3-TRIMETHYL-3-CYCLOPENTEN-1-YL)-4-PENTEN-2-OL |
| Mousse cristal | METHYL 2,4-DIHYDROXY-3,6-DIMETHYLBENZOATE |
| LIMBANOL | (+−)-1-(2,2,3,6-TETRAMETHYL-CYCLOHEXYL)-3-HEXANOL |
| Habanolide | (12E)-Oxacyclohexadec-12-en-2-one |
| Ethyl praline | 2-Ethyl-3-hydroxy-4H-pyran-4-one |
| FIRSANTOL | 2-Methyl-4-(2,2,3-trimethyl-3-cyclopenten-1-yl)-4-penten-1-ol |
| Pipol salicylate | (3Z)-3-Hexen-1-yl salicylate |
| Muscone | (3R)-3-Methylcyclopentadecanone |
| BENZYL SALICYLATE | Benzyl salicylate |
| Ambrettolide | (10E)-Oxacycloheptadec-10-en-2-one |
| Romandolide | 2-{(1RS)-1-[(1SR)-3,3-dimethylcyclohexyl]ethoxy}-2-oxoethyl propionate (A) |
|  | 2-{(1RS)-1-[(1RS)-3,3-dimethylcyclohexyl]ethoxy}-2-oxoethyl propionate (B) |
|  | 2-oxo-2-{[(1RS,2RS)-2,6,6-trimethylcycloheptyl]oxy}ethyl propionate (C) |
|  | 2-oxo-2-{[(1RS,2SR)-2,6,6-trimethylcycloheptyl]oxy}ethyl propionate (D) |
| EXALTONE | Cyclopentadecanone |
| VERTOFIX COEUR | 1-(Cedr-8-en-9-yl)ethanone |
| EXALTOLIDE | Oxacyclohexadecan-2-one |
| Lyral | (1R)-4-(4-Hydroxy-4-methylpentyl)-3-cyclohexene-1-carbaldehyde |
| Muscenone dextro | (3R,5E)-3-Methyl-5-cyclopentadecen-1-one |

TABLE 6

Examples of perfume raw materials that no longer remain available for selection for use in the medium volatility component because the perfume raw material becomes suppressed (i.e. not perceived by the consumer) in the presence of the modulator.

| COMMON NAME | IUPAC NAME |
| --- | --- |
| Nerol | (Z)-3,7-DIMETHYL-2,6-OCTADIEN-1-OL |
| GERANIOL | (E)-3,7-DIMETHYL-2,6-OCTADIEN-1-OL |
| ACETATE DE NOPYLE | 2-(6,6-DIMETHYL-BICYCLO[3.1.1]HEPT-2-EN-2-YL)ETHYL ACETATE |
| FLOROL | (+−)-TETRAHYDRO-2-ISOBUTYL-4-METHYL-4(2H)-PYRANOL |
| INDOMETHYLENE | 4,4A,5,9B-TETRAHYDRO-INDENO[1,2-D]-1,3-DIOXIN |
| Isoeugenol | 2-methoxy-4-[(1E)-1-propen-1-yl]phenol |
| RESEDA BODY | 2-BENZYL-4,4,6-TRIMETHYL-1,3-DIOXANE |
| METHYLIONONE GAMMA COEUR | (+−)-(E)-3-METHYL-4-(2,6,6-TRIMETHYL-2-CYCLOHEXEN-1-YL)-3-BUTEN-2-ONE |
| IRALIA | (+−)-(3E)-3-methyl-4-(2,6,6-trimethyl-2-cyclohexen-1-yl)-3-buten-2-one (A) (+−)-(1E)-1-(2,6,6-trimethyl-2-cyclohexen-1-yl)-1-penten-3-one (B) |
| HELIOPROPANAL | (+−)-3-(1,3-BENZODIOXOL-5-YL)-2-METHYLPROPANAL |
| FARENAL | (+−)-2,6,10-TRIMETH YL-9-UNDECENAL |
| CORPS RHUBARBE | (+−)-1,3-DIMETHYL-3-PHENYLBUTYL ACETATE |
| METHYL JASMONATE | methyl {(1RS,2RS)-3-oxo-2-[(2Z)-2-penten-1-yl]cyclopentyl}acetate |

TABLE 7

Examples of perfume raw materials that no longer remain available for selection for use in the low volatility component because the perfume raw material becomes suppressed (i.e. not perceived by the consumer) in the presence of the modulator.

| COMMON NAME | IUPAC NAME |
| --- | --- |
| CEDRENOL | (+−)-3,6,8,8-tetramethyloctahydro-1H-3a,7-methanoazulen-6-ol |
| Hexyl salicylate | HEXYL 2-HYDROXYBENZOATE |
| Galaxolide 70 DIPG | (+−)-4,6,6,7,8,8-hexamethyl-1,3,4,6,7,8-hexahydrocyclopenta[g]isochromene |
| Galaxolide 70 MIP Extra | (+−)-4,6,6,7,8,8-hexamethyl-1,3,4,6,7,8-hexahydrocyclopenta[g]isochromene |
| Bacdanol | (+−)-2-ETHYL-4-(2,2,3-TRIMETHYL-3-CYCLOPENTEN-1-YL)-2-BUTEN-1-OL |
| Dioxycarbinol | 2-BENZYL-1,3-DIOXOLANE-4-METHANOL (A) 2-BENZYL-1,3-DIOXAN-5-OL (B) |
| Polysantol | (−)-(2R,4E)-3,3-dimethyl-5-[(1R)-2,2,3-trimethyl-3-cyclopenten-1-yl]-4-penten-2-ol (A) (−)-(2S,4E)-3,3-dimethyl-5-[(1R)-2,2,3-trimethyl-3-cyclopenten-1-yl]-4-penten-2-ol (B) |
| NIRVANOL | (+)-(2S,4E)-3,3-dimethyl-5-[(1 S)-2,2,3-trimethyl-3-cyclopenten-1-yl]-4-penten-2-ol (A) (+)-(2R,4E)-3,3-dimethyl-5-[(1S)-2,2,3-trimethyl-3-cyclopenten-1-yl]-4-penten-2-ol (B) |
| MYRRHONE | (+−)-(E)-4-(2,2,C-3,T-6-TETRAMETHYL-R-1-CYCLOHEXYL)-3-BUTEN-2-ONE (A) (+−)-(E)-4-(2,2,T-3,T-6-TETRAMETHYL-R-1-CYCLOHEXYL)-3-BUTEN-2-ONE (B) |
| ASTROTONE | 1,4-dioxacycloheptadecane-5,17-dione |

In one aspect, perfume raw materials suitable to include in a composition according to an embodiment presented herein are selected from the perfume raw materials set forth in Table 8.

TABLE 8

Examples of perfume raw materials that may be utilized with at least one modulator having a vapor pressure of less than 0.0008 Torr at 22° C. and Hansen solubility parameters according to several aspects presented herein

| COMMON NAME | IUPAC NAME |
| --- | --- |
| CINNAMYL PROPIONATE | (E)-3-PHENYL-2-PROPENYL PROPANOATE |
| ALCOHOL C 12 | 1-dodecanol |
| TRIDECYLENIC ALDEHYDE | (2E)-2-tridecenal |
| CETALOX LAEVO | Dodecahydro-3a,6,6,9a-tetramethylnaphtho(2,1-b)furan |
| SANDALORE | (+−)-3-methyl-5-(2,2,3-trimethyl-3-cyclopenten-1-yl)-2-pentanol |
| GAMMA UNDECALACTONE | 5-heptyloxolan-2-one |
| TRICYCLONE | (1R-(1alpha,3alpha,4aalpha))-2,3,4,4a,5,6-hexahydro-2,2-dimethyl-1,3-methanonaphthalen-7(1H)-one |
| EXALTONE | cyclopentadecanone |
| UNDECALACTONE DELTA | (+−)-5-heptyldihydro-2(3H)-furanone 6-hexyltetrahydro-2H-pyran-2-one |
| NEROLIDOL | 3,7,11-TRIMETHYL-1,6,10-DODECATRIEN-3-OL |
| HELVETOLIDE ® | (+)-(1S,1'R)-2-[1-(3',3'-DIMETHYL-1'-CYCLOHEXYL)ETHOXY]-2-METHYLPROPYL PROPANOATE |
| MUGUET ALDEHYDE ARR | (+−)-(3,7-DIMETHYL-6-OCTENYLOXY)ACETALDEHYDE |
| CEDROXYDE ® | (+−)-(4Z,8E)-1,4,8-trimethyl-13-oxabicyclo[10.1.0]trideca-4,8-diene (+−)-(4Z,8E)-1,5,8-trimethyl-13-oxabicyclo[10.1.0]trideca-4,8-diene |
| PIPOL SALICYLATE | (3Z)-3-hexen-1-yl salicylate |
| BACDANOL | (+−)-2-ETHYL-4-(2,2,3-TRIMETHYL-3-CYCLOPENTEN-1-YL)-2-BUTEN-1-OL |
| JASMOLACTONE DELTA | (+−)-(Z)-8-DECEN-5-OLIDE (+−)-(E)-8-DECEN-5-OLIDE |
| DARTANOL ® | (−)-(2E)-2-ethyl-4-[(1R)-2,2,3-trimethyl-3-cyclopenten-1-yl]-2-buten-1-ol |
| ROMANDOLIDE ® | 2-{(1RS)-1-[(1SR)-3,3-dimethylcyclohexyl]ethoxy}-2-oxoethyl propionate 2-oxo-2-{[(1RS,2SR)-2,6,6-trimethylcycloheptyl]oxy}ethyl propionate 2-{(1RS)-1-[(1RS)-3,3-dimethylcyclohexyl]ethoxy}-2-oxoethyl propionate 2-oxo-2-{[(1RS,2RS)-2,6,6-trimethylcycloheptyl]oxy}ethyl propionate |
| NOOTKATONE PURE | (+)-(4R,4aS,6R)-4,4a-dimethyl-6-(1-propen-2-yl)-4,4a,5,6,7,8-hexahydro-2(3H)-naphthalenone |
| NORLIMBANOL ® DEXTRO | (+)-(3R)-1-[(1R,6S)-2,2,6-trimethylcyclohexyl]-3-hexanol (+)-(3S)-1-[(1R,6S)-2,2,6-trimethylcyclohexyl]-3-hexanol 1-[(1S ,6S)-2,2,6-trimethylcyclohexyl]-3-hexanol |
| AMIONE | (1E)-1-(2,6,6-trimethyl-1-cyclohexen-1-yl)-1,6-heptadien-3-one (+−)-(1E)-1-(2,6,6-trimethyl-2-cyclohexen-1-yl)-1,6-heptadien-3-one |
| HEDIONE ® | methyl 2-((1RS,2RS)-3-oxo-2-pentylcyclopentyl)acetate |
| HEXYL SALICYLATE | HEXYL 2-HYDROXYBENZOATE |
| EXALTOLIDE ® | oxacyclohexadecan-2-one |
| CETALOX ® | (3aRS,5aSR,9aSR,9bRS)-3a,6,6,9a-tetramethyldodecahydronaphtho[2,1-b]furan |
| AMBROX ® | (−)-(3aR,5aS,9aS,9bR)-3a,6,6,9a-tetramethyldodecahydronaphtho[2,1-b]furan |
| MUSCONE | (+−)-3-methylcyclopentadecanone |

TABLE 8-continued

Examples of perfume raw materials that may be utilized with at least one modulator having a vapor pressure of less than 0.0008 Torr at 22° C. and Hansen solubility parameters according to several aspects presented herein

| COMMON NAME | IUPAC NAME |
| --- | --- |
| EXALTENONE | (Z)-4-CYCLOPENTADECEN-1-ONE |
| AMBRETTOLIDE | (10E)-oxacycloheptadec-10-en-2-one |
| DODECALACTONE CP | (+−)-5-octyldihydro-2(3H)-furanone |
| PARADISONE ® | methyl 2-[(1R,2S)-3-oxo-2-pentylcyclopentyl]acetate |
| METHYL JASMONATE | methyl {(1RS,2RS)-3-oxo-2-[(2Z)-2-penten-1-yl]cyclopentyl}acetate |
| GALAXOLIDE | 4,6,6,7,8,8-hexamethyl-1,3,4,7-tetrahydrocyclopenta[g]isochromene |
| CYCLOPENTADECANOLIDE | Oxacyclohexadecan-2-one |
| NORLIMBANOL ® | 1-[(1RS,6SR)-2,2,6-trimethylcyclohexyl]-3-hexanol |
| DODECALACTONE DELTA | (+−)-6-heptyltetrahydro-2H-pyran-2-one |
| AMBROX ® SUPER | (−)-(3aR,5aS,9aS,9bR)-3a,6,6,9a-tetramethyldodecahydronaphtho[2,1-b]furan |
| BENZYL BENZOATE | BENZYL BENZOATE |
| MUSC X | 1-TERT-BUTYL-3,5-DIMETHYL-2,4,6-TRINITROBENZENE |
| AMYLCINNAMIC ALDEHYDE R | (2E)-2-benzylideneheptanal |
| HEXYLCINNAMIC ALDEHYDE | (2E)-2-benzylideneoctanal |
| LIMBANOL ® | (+−)-1-(2,2,3,6-TETRAMETHYL-CYCLOHEXYL)-3-HEXANOL |
| CIVETTONE | (9Z)-9-cycloheptadecen-1-one |
| MUSK KETONE | 1-(4-tert-butyl-2,6-dimethyl-3,5-dinitrophenyl)ethanone |
| VULCANOLIDE ® | (6RS,7RS)-3,5,5,6,7,8,8-heptamethyl-5,6,7,8-tetrahydro-2-naphthalenecarbaldehyde |
| IPM | propan-2-yl tetradecanoate |

In some aspects, the composition constructed using the method described herein comprises:
  a. ethanol, in an amount from 30 to 75 wt % relative to the total weight of the composition;
  b. a fragrance component present in an amount from 0.04 to 40 wt %, relative to the total weight of the composition,
    wherein the fragrance component comprises:
      i. a high volatility component an amount from 0.08 to 55 wt % of the fragrance component, comprising
        a. a first at least one perfume raw material having a first vapor pressure greater than 0.08 Torr at 22° C.; and optionally
        b. a second at least one perfume raw material having a first vapor pressure greater than 0.08 Torr at 22° C.;
      ii. a medium volatility component in an amount from 0.08 to 85 wt % of the fragrance component, comprising:
        a. a first at least one perfume raw material having a first vapor pressure range of 0.0008 to 0.08 Torr at 22° C.; and optionally
        b. a second at least one perfume raw material having a first vapor pressure range of 0.0008 to 0.08 Torr at 22° C.; and
  c. at least one modulator in an amount from 0.1 to 50 wt %, relative to the total weight of the composition;

wherein the first vapor pressure of the at least one first perfume raw material of the high volatility component is determined in the absence of the at least one modulator;
wherein the first vapor pressure of the at least one second perfume raw material of the high volatility component is determined in the absence of the at least one modulator;
wherein the at least one modulator changes the first vapor pressure of the at least one second perfume raw material of the high volatility component to a second vapor pressure;
wherein the second vapor pressure of the at least one second perfume raw material of the high volatility component is in the range of 0.0008 to 0.08 Torr at 22° C.;
wherein the first vapor pressure range of the at least one first perfume raw material of the medium volatility component is determined in the absence of the at least one modulator;
wherein the first vapor pressure range of the at least one second perfume raw material of the medium volatility component is determined in the absence of the at least one modulator;
wherein the at least one modulator changes the first vapor pressure range of the at least one second perfume raw material of the medium volatility component to a second vapor pressure; and
wherein the second vapor pressure of the at least one second perfume raw material of the medium volatility component is less than 0.0008 Torr at 22° C.

In some aspects, the fragrance component present in an amount from 0.04 to 20 wt %, relative to the total weight of the composition.

In some aspects, the composition further comprises water, in an amount of less than or equal to 15 wt % relative to the total weight of the composition.

In some aspects, the composition further comprises water, in an amount 5 to 15 wt % relative to the total weight of the composition.

In some aspects, the composition further comprises water, in an amount 0 to 5 wt % relative to the total weight of the composition.

In certain aspects, the compositions of the present invention comprise at least 5, at least 10, at least 15 or at least 20 perfume raw materials. If there is more than one perfume raw material, then the ranges provided hereinabove cover the total weight of all of the perfume raw materials.

In some aspects, the high volatility component consists of only the first at least one perfume raw material having a first vapor pressure greater than 0.08 Torr at 22° C. In these aspects, the first at least one perfume raw material having a first vapor pressure greater than 0.08 Torr at 22° C. is present in an amount ranging from 0.08 to 55 wt % of the fragrance component. Alternatively, the first at least one perfume raw material having a first vapor pressure greater than 0.08 Torr at 22° C. is present in an amount ranging from 0.1 to 55 wt % of the fragrance component. Alternatively, the first at least one perfume raw material having a first vapor pressure greater than 0.08 Torr at 22° C. is present in an amount ranging from 0.15 to 55 wt % of the fragrance component. Alternatively, the first at least one perfume raw material having a first vapor pressure greater than 0.08 Torr at 22° C. is present in an amount ranging from 0.2 to 55 wt % of the fragrance component. Alternatively, the first at least one perfume raw material having a first vapor pressure greater than 0.08 Torr at 22° C. is present in an amount ranging from 0.25 to 55 wt % of the fragrance component. Alternatively, the first at least one perfume raw material having a first vapor pressure greater than 0.08 Torr at 22° C. is present in an amount ranging from 0.3 to 55 wt % of the fragrance component. Alternatively, the first at least one perfume raw material having a first vapor pressure greater than 0.08 Torr at 22° C. is present in an amount ranging from 0.35 to 55 wt % of the fragrance component. Alternatively, the first at least one perfume raw material having a first vapor pressure greater than 0.08 Torr at 22° C. is present in an amount ranging from 0.4 to 55 wt % of the fragrance component. Alternatively, the first at least one perfume raw material having a first vapor pressure greater than 0.08 Torr at 22° C. is present in an amount ranging from 0.45 to 55 wt % of the fragrance component. Alternatively, the first at least one perfume raw material having a first vapor pressure greater than 0.08 Torr at 22° C. is present in an amount ranging from 0.5 to 55 wt % of the fragrance component. Alternatively, the first at least one perfume raw material having a first vapor pressure greater than 0.08 Torr at 22° C. is present in an amount ranging from 0.55 to 55 wt % of the fragrance component. Alternatively, the first at least one perfume raw material having a first vapor pressure greater than 0.08 Torr at 22° C. is present in an amount ranging from 0.6 to 55 wt % of the fragrance component. Alternatively, the first at least one perfume raw material having a first vapor pressure greater than 0.08 Torr at 22° C. is present in an amount ranging from 0.65 to 55 wt % of the fragrance component. Alternatively, the first at least one perfume raw material having a first vapor pressure greater than 0.08 Torr at 22° C. is present in an amount ranging from 0.7 to 55 wt % of the fragrance component. Alternatively, the first at least one perfume raw material having a first vapor pressure greater than 0.08 Torr at 22° C. is present in an amount ranging from 0.75 to 55 wt % of the fragrance component. Alternatively, the first at least one perfume raw material having a first vapor pressure greater than 0.08 Torr at 22° C. is present in an amount ranging from 0.8 to 55 wt % of the fragrance component. Alternatively, the first at least one perfume raw material having a first vapor pressure greater than 0.08 Torr at 22° C. is present in an amount ranging from 0.85 to 55 wt % of the fragrance component. Alternatively, the first at least one perfume raw material having a first vapor pressure greater than 0.08 Torr at 22° C. is present in an amount ranging from 0.9 to 55 wt % of the fragrance component. Alternatively, the first at least one perfume raw material having a first vapor pressure greater than 0.08 Torr at 22° C. is present in an amount ranging from 0.95 to 55 wt % of the fragrance component. Alternatively, the first at least one perfume raw material having a first vapor pressure greater than 0.08 Torr at 22° C. is present in an amount ranging from 1 to 55 wt % of the fragrance component. Alternatively, the first at least one perfume raw material having a first vapor pressure greater than 0.08 Torr at 22° C. is present in an amount ranging from 1.15 to 55 wt % of the fragrance component. Alternatively, the first at least one perfume raw material having a first vapor pressure greater than 0.08 Torr at 22° C. is present in an amount ranging from 1.2 to 55 wt % of the fragrance component. Alternatively, the first at least one perfume raw material having a first vapor pressure greater than 0.08 Torr at 22° C. is present in an amount ranging from 1.25 to 55 wt % of the fragrance component. Alternatively, the first at least one perfume raw material having a first vapor pressure greater than 0.08 Torr at 22° C. is present in an amount ranging from 1.3 to 55 wt % of the fragrance component. Alternatively, the first at least one perfume raw material having a first vapor pressure greater than 0.08 Torr at 22° C. is present in an amount ranging from 1.35 to 55 wt % of the fragrance component. Alternatively, the first at least one perfume raw material having a first vapor pressure greater than 0.08 Torr at 22° C. is present in an amount ranging from 1.4 to 55 wt % of the fragrance component. Alternatively, the first at least one perfume raw material having a first vapor pressure greater than 0.08 Torr at 22° C. is present in an amount ranging from 1.45 to 55 wt % of the fragrance component. Alternatively, the first at least one perfume raw material having a first vapor pressure greater than 0.08 Torr at 22° C. is present in an amount ranging from 1.5 to 55 wt % of the fragrance component. Alternatively, the first at least one perfume raw material having a first vapor pressure greater than 0.08 Torr at 22° C. is present in an amount ranging from 1.55 to 55 wt % of the fragrance component. Alternatively, the first at least one perfume raw material having a first vapor pressure greater than 0.08 Torr at 22° C. is present in an amount ranging from 1.6 to 55 wt % of the fragrance component. Alternatively, the first at least one perfume raw material having a first vapor pressure greater than 0.08 Torr at 22° C. is present in an amount ranging from 1.65 to 55 wt % of the fragrance component. Alternatively, the first at least one perfume raw material having a first vapor pressure greater than 0.08 Torr at 22° C. is present in an amount ranging from 1.7 to 55 wt % of the fragrance component. Alternatively, the first at least one perfume raw material having a first vapor pressure greater than 0.08 Torr at 22° C. is present in an amount ranging from 1.75 to 55 wt % of the fragrance component. Alternatively, the first at least one perfume raw material having a first vapor pressure greater than 0.08 Torr at 22° C. is present in an amount ranging from 1.8 to 55 wt % of the fragrance component. Alternatively, the first at least one perfume raw material having a first vapor pressure greater than 0.08 Torr at 22° C. is present in an amount ranging from 1.85 to 55 wt % of the fragrance component. Alternatively, the first at least one perfume raw material having a first vapor pressure greater than 0.08 Torr at 22° C. is present in an amount ranging from 1.9 to 55 wt % of the fragrance component. Alternatively, the first at least one perfume raw material having a first vapor pressure greater than 0.08 Torr at 22° C. is present in an amount ranging from 1.95 to 55 wt % of the fragrance component. Alternatively, the first at least one perfume raw material having a first vapor pressure greater than 0.08 Torr at 22° C. is present in an amount ranging from 2 to 55 wt % of the fragrance component. Alternatively, the first at least one perfume raw material having a first vapor pressure greater than 0.08 Torr at 22° C. is present in an amount ranging from 2.15 to 55 wt % of the fragrance component. Alternatively, the first at least one perfume raw material having a first vapor pressure greater than 0.08 Torr at 22° C. is present in an amount ranging from 2.2 to 55 wt % of the fragrance component. Alternatively, the first at least one perfume raw material having a first vapor pressure greater than 0.08 Torr at 22° C. is present in an amount ranging from 2.25 to 55 wt % of the fragrance component. Alternatively, the first at least one perfume raw material having a first vapor pressure greater than 0.08 Torr at 22° C. is present in an amount ranging from 2.3 to 55 wt % of the fragrance component. Alternatively, the first at least one perfume raw material having a first vapor pressure greater than 0.08 Torr at 22° C. is present in an amount ranging from 2.35 to 55 wt % of the fragrance component. Alternatively, the first at least one perfume raw material having a first vapor pressure greater than 0.08 Torr at 22° C. is present in an amount ranging from 2.4 to 55 wt % of the fragrance component. Alternatively, the first at least one perfume raw material having a first vapor pressure greater than 0.08 Torr at 22° C. is present in an amount ranging from 2.45 to 55 wt % of the fragrance component. Alternatively, the first at least one perfume raw material having a first vapor pressure greater than 0.08 Torr at 22° C. is present in an amount ranging from 2.5 to 55 wt % of the fragrance component. Alternatively, the first at least one perfume raw material having a first vapor pressure greater than 0.08 Torr at 22° C. is present in an amount ranging from 2.55 to 55 wt % of the fragrance component. Alternatively, the first at least one perfume raw material having a first vapor pressure greater than 0.08 Torr at 22° C. is present in an amount ranging from 2.6 to 55 wt % of the fragrance component. Alternatively, the first at least one perfume raw material having a first vapor pressure greater than 0.08 Torr at 22° C. is present in an amount ranging from 2.65 to 55 wt % of the fragrance component. Alternatively, the first at least one perfume raw material having a first vapor pressure greater than 0.08 Torr at 22° C. is present in an amount ranging from 2.7 to 55 wt % of the fragrance component. Alternatively, the first at least one perfume raw material having a first vapor pressure greater than 0.08 Torr at 22° C. is present in an amount ranging from 2.75 to 55 wt % of the fragrance component. Alternatively, the first at least one perfume raw material having a first vapor pressure greater than 0.08 Torr at 22° C. is present in an amount ranging from 2.8 to 55 wt % of the fragrance component. Alternatively, the first at least one perfume raw material having a first vapor pressure greater than 0.08 Torr at 22° C. is present in an amount ranging from 2.85 to 55 wt % of the fragrance component. Alternatively, the first at least one perfume raw material having a first vapor pressure greater than 0.08 Torr at 22° C. is present in an amount ranging from 2.9 to 55 wt % of the fragrance component. Alternatively, the first at least one perfume raw material having a first vapor pressure greater than 0.08 Torr at 22° C. is present in an amount ranging from 2.95 to 55 wt % of the fragrance component. Alternatively, the first at least one perfume raw material having a first vapor pressure greater than 0.08 Torr at 22° C. is present in an amount ranging from 3 to 55 wt % of the fragrance component. Alternatively, the first at least one perfume raw material having a first vapor pressure greater than 0.08 Torr at 22° C. is present in an amount ranging from 3.15 to 55 wt % of the fragrance component. Alternatively, the first at least one perfume raw material having a first vapor pressure greater than 0.08 Torr at 22° C. is present in an amount ranging from 3.2 to 55 wt % of the fragrance component. Alternatively, the first at least one perfume raw material having a first vapor pressure greater than 0.08 Torr at 22° C. is present in an amount ranging from 3.25 to 55 wt % of the fragrance component. Alternatively, the first at least one perfume raw material having a first vapor pressure greater than 0.08 Torr at 22° C. is present in an amount ranging from 3.3 to 55 wt % of the fragrance component. Alternatively, the first at least one perfume raw material having a first vapor pressure greater than 0.08 Torr at 22° C. is present in an amount ranging from 3.35 to 55 wt % of the fragrance component. Alternatively, the first at least one perfume raw material having a first vapor pressure greater than 0.08 Torr at 22° C. is present in an amount ranging from 3.4 to 55 wt % of the fragrance component. Alternatively, the first at least one perfume raw material having a first vapor pressure greater than 0.08 Torr at 22° C. is present in an amount ranging from 3.45 to 55 wt % of the fragrance component. Alternatively, the first at least one perfume raw material having a first vapor pressure greater than 0.08 Torr at 22° C. is present in an amount ranging from 3.5 to 55 wt % of the fragrance component. Alternatively, the first at least one perfume raw material having a first vapor pressure greater than 0.08 Torr at 22° C. is present in an amount ranging from 3.55 to 55 wt % of the fragrance component. Alternatively, the first at least one perfume raw material having a first vapor pressure greater than 0.08 Torr at 22° C. is present in an amount ranging from 3.6 to 55 wt % of the fragrance component. Alternatively, the first at least one perfume raw material having a first vapor pressure greater than 0.08 Torr at 22° C. is present in an amount ranging from 3.65 to 55 wt % of the fragrance component. Alternatively, the first at least one perfume raw material having a first vapor pressure greater than 0.08 Torr at 22° C. is present in an amount ranging from 3.7 to 55 wt % of the fragrance component. Alternatively, the first at least one perfume raw material having a first vapor pressure greater than 0.08 Torr at 22° C. is present in an amount ranging from 3.75 to 55 wt % of the fragrance component. Alternatively, the first at least one perfume raw material having a first vapor pressure greater than 0.08 Torr at 22° C. is present in an amount ranging from 3.8 to 55 wt % of the fragrance component. Alternatively, the first at least one perfume raw material having a first vapor pressure greater than 0.08 Torr at 22° C. is present in an amount ranging from 3.85 to 55 wt % of the fragrance component. Alternatively, the first at least one perfume raw material having a first vapor pressure greater than 0.08 Torr at 22° C. is present in an amount ranging from 3.9 to 55 wt % of the fragrance component. Alternatively, the first at least one perfume raw material having a first vapor pressure greater than 0.08 Torr at 22° C. is present in an amount ranging from 3.95 to 55 wt % of the fragrance component. Alternatively, the first at least one perfume raw material having a first vapor pressure greater than 0.08 Torr at 22° C. is present in an amount ranging from 4 to 55 wt % of the fragrance component. Alternatively, the first at least one perfume raw material having a first vapor pressure greater than 0.08 Torr at 22° C. is present in an amount ranging from 4.15 to 55 wt % of the fragrance component. Alternatively, the first at least one perfume raw material having a first vapor pressure greater than 0.08 Torr at 22° C. is present in an amount ranging from 4.2 to 55 wt % of the fragrance component. Alternatively, the first at least one perfume raw material having a first vapor pressure greater than 0.08 Torr at 22° C. is present in an amount ranging from 4.25 to 55 wt % of the fragrance component. Alternatively, the first at least one perfume raw material having a first vapor pressure greater than 0.08 Torr at 22° C. is present in an amount ranging from 4.3 to 55 wt % of the fragrance component. Alternatively, the first at least one perfume raw material having a first vapor pressure greater than 0.08 Torr at 22° C. is present in an amount ranging from 4.35 to 55 wt % of the fragrance component. Alternatively, the first at least one perfume raw material having a first vapor pressure greater than 0.08 Torr at 22° C. is present in an amount ranging from 4.4 to 55 wt % of the fragrance component. Alternatively, the first at least one perfume raw material having a first vapor pressure greater than 0.08 Torr at 22° C. is present in an amount ranging from 4.45 to 55 wt % of the fragrance component. Alternatively, the first at least one perfume raw material having a first vapor pressure greater than 0.08 Torr at 22° C. is present in an amount ranging from 4.5 to 55 wt % of the fragrance component. Alternatively, the first at least one perfume raw material having a first vapor pressure greater than 0.08 Torr at 22° C. is present in an amount ranging from 4.55 to 55 wt % of the fragrance component. Alternatively, the first at least one perfume raw material having a first vapor pressure greater than 0.08 Torr at 22° C.

is present in an amount ranging from 4.6 to 55 wt % of the fragrance component. Alternatively, the first at least one perfume raw material having a first vapor pressure greater than 0.08 Torr at 22° C. is present in an amount ranging from 4.65 to 55 wt % of the fragrance component. Alternatively, the first at least one perfume raw material having a first vapor pressure greater than 0.08 Torr at 22° C. is present in an amount ranging from 4.7 to 55 wt % of the fragrance component. Alternatively, the first at least one perfume raw material having a first vapor pressure greater than 0.08 Torr at 22° C. is present in an amount ranging from 4.75 to 55 wt % of the fragrance component. Alternatively, the first at least one perfume raw material having a first vapor pressure greater than 0.08 Torr at 22° C. is present in an amount ranging from 4.8 to 55 wt % of the fragrance component. Alternatively, the first at least one perfume raw material having a first vapor pressure greater than 0.08 Torr at 22° C. is present in an amount ranging from 4.85 to 55 wt % of the fragrance component. Alternatively, the first at least one perfume raw material having a first vapor pressure greater than 0.08 Torr at 22° C. is present in an amount ranging from 4.9 to 55 wt % of the fragrance component. Alternatively, the first at least one perfume raw material having a first vapor pressure greater than 0.08 Torr at 22° C. is present in an amount ranging from 4.95 to 55 wt % of the fragrance component. Alternatively, the first at least one perfume raw material having a first vapor pressure greater than 0.08 Torr at 22° C. is present in an amount ranging from 5 to 55 wt % of the fragrance component. Alternatively, the first at least one perfume raw material having a first vapor pressure greater than 0.08 Torr at 22° C. is present in an amount ranging from 5.15 to 55 wt % of the fragrance component. Alternatively, the first at least one perfume raw material having a first vapor pressure greater than 0.08 Torr at 22° C. is present in an amount ranging from 5.2 to 55 wt % of the fragrance component. Alternatively, the first at least one perfume raw material having a first vapor pressure greater than 0.08 Torr at 22° C. is present in an amount ranging from 5.25 to 55 wt % of the fragrance component. Alternatively, the first at least one perfume raw material having a first vapor pressure greater than 0.08 Torr at 22° C. is present in an amount ranging from 5.3 to 55 wt % of the fragrance component. Alternatively, the first at least one perfume raw material having a first vapor pressure greater than 0.08 Torr at 22° C. is present in an amount ranging from 5.35 to 55 wt % of the fragrance component. Alternatively, the first at least one perfume raw material having a first vapor pressure greater than 0.08 Torr at 22° C. is present in an amount ranging from 5.4 to 55 wt % of the fragrance component. Alternatively, the first at least one perfume raw material having a first vapor pressure greater than 0.08 Torr at 22° C. is present in an amount ranging from 5.45 to 55 wt % of the fragrance component. Alternatively, the first at least one perfume raw material having a first vapor pressure greater than 0.08 Torr at 22° C. is present in an amount ranging from 5.5 to 55 wt % of the fragrance component. Alternatively, the first at least one perfume raw material having a first vapor pressure greater than 0.08 Torr at 22° C. is present in an amount ranging from 5.55 to 55 wt % of the fragrance component. Alternatively, the first at least one perfume raw material having a first vapor pressure greater than 0.08 Torr at 22° C. is present in an amount ranging from 5.6 to 55 wt % of the fragrance component. Alternatively, the first at least one perfume raw material having a first vapor pressure greater than 0.08 Torr at 22° C. is present in an amount ranging from 5.65 to 55 wt % of the fragrance component. Alternatively, the first at least one perfume raw material having a first vapor pressure greater than 0.08 Torr at 22° C. is present in an amount ranging from 5.7 to 55 wt % of the fragrance component. Alternatively, the first at least one perfume raw material having a first vapor pressure greater than 0.08 Torr at 22° C. is present in an amount ranging from 5.75 to 55 wt % of the fragrance component. Alternatively, the first at least one perfume raw material having a first vapor pressure greater than 0.08 Torr at 22° C. is present in an amount ranging from 5.8 to 55 wt % of the fragrance component. Alternatively, the first at least one perfume raw material having a first vapor pressure greater than 0.08 Torr at 22° C. is present in an amount ranging from 5.85 to 55 wt % of the fragrance component. Alternatively, the first at least one perfume raw material having a first vapor pressure greater than 0.08 Torr at 22° C. is present in an amount ranging from 5.9 to 55 wt % of the fragrance component. Alternatively, the first at least one perfume raw material having a first vapor pressure greater than 0.08 Torr at 22° C. is present in an amount ranging from 5.95 to 55 wt % of the fragrance component. Alternatively, the first at least one perfume raw material having a first vapor pressure greater than 0.08 Torr at 22° C. is present in an amount ranging from 6 to 55 wt % of the fragrance component. Alternatively, the first at least one perfume raw material having a first vapor pressure greater than 0.08 Torr at 22° C. is present in an amount ranging from 6.15 to 55 wt % of the fragrance component. Alternatively, the first at least one perfume raw material having a first vapor pressure greater than 0.08 Torr at 22° C. is present in an amount ranging from 6.2 to 55 wt % of the fragrance component. Alternatively, the first at least one perfume raw material having a first vapor pressure greater than 0.08 Torr at 22° C. is present in an amount ranging from 6.25 to 55 wt % of the fragrance component. Alternatively, the first at least one perfume raw material having a first vapor pressure greater than 0.08 Torr at 22° C. is present in an amount ranging from 6.3 to 55 wt % of the fragrance component. Alternatively, the first at least one perfume raw material having a first vapor pressure greater than 0.08 Torr at 22° C. is present in an amount ranging from 6.35 to 55 wt % of the fragrance component. Alternatively, the first at least one perfume raw material having a first vapor pressure greater than 0.08 Torr at 22° C. is present in an amount ranging from 6.4 to 55 wt % of the fragrance component. Alternatively, the first at least one perfume raw material having a first vapor pressure greater than 0.08 Torr at 22° C. is present in an amount ranging from 6.45 to 55 wt % of the fragrance component. Alternatively, the first at least one perfume raw material having a first vapor pressure greater than 0.08 Torr at 22° C. is present in an amount ranging from 6.5 to 55 wt % of the fragrance component. Alternatively, the first at least one perfume raw material having a first vapor pressure greater than 0.08 Torr at 22° C. is present in an amount ranging from 6.55 to 55 wt % of the fragrance component. Alternatively, the first at least one perfume raw material having a first vapor pressure greater than 0.08 Torr at 22° C. is present in an amount ranging from 6.6 to 55 wt % of the fragrance component. Alternatively, the first at least one perfume raw material having a first vapor pressure greater than 0.08 Torr at 22° C. is present in an amount ranging from 6.65 to 55 wt % of the fragrance component. Alternatively, the first at least one perfume raw material having a first vapor pressure greater than 0.08 Torr at 22° C. is present in an amount ranging from 6.7 to 55 wt % of the fragrance component. Alternatively, the first at least one perfume raw material having a first vapor pressure greater than 0.08 Torr at 22° C. is present in an amount ranging from 6.75 to 55 wt % of the fragrance component.

Alternatively, the first at least one perfume raw material having a first vapor pressure greater than 0.08 Torr at 22° C. is present in an amount ranging from 6.8 to 55 wt % of the fragrance component. Alternatively, the first at least one perfume raw material having a first vapor pressure greater than 0.08 Torr at 22° C. is present in an amount ranging from 6.85 to 55 wt % of the fragrance component. Alternatively, the first at least one perfume raw material having a first vapor pressure greater than 0.08 Torr at 22° C. is present in an amount ranging from 6.9 to 55 wt % of the fragrance component. Alternatively, the first at least one perfume raw material having a first vapor pressure greater than 0.08 Torr at 22° C. is present in an amount ranging from 6.95 to 55 wt % of the fragrance component. Alternatively, the first at least one perfume raw material having a first vapor pressure greater than 0.08 Torr at 22° C. is present in an amount ranging from 7 to 55 wt % of the fragrance component. Alternatively, the first at least one perfume raw material having a first vapor pressure greater than 0.08 Torr at 22° C. is present in an amount ranging from 7.15 to 55 wt % of the fragrance component. Alternatively, the first at least one perfume raw material having a first vapor pressure greater than 0.08 Torr at 22° C. is present in an amount ranging from 7.2 to 55 wt % of the fragrance component. Alternatively, the first at least one perfume raw material having a first vapor pressure greater than 0.08 Torr at 22° C. is present in an amount ranging from 7.25 to 55 wt % of the fragrance component. Alternatively, the first at least one perfume raw material having a first vapor pressure greater than 0.08 Torr at 22° C. is present in an amount ranging from 7.3 to 55 wt % of the fragrance component. Alternatively, the first at least one perfume raw material having a first vapor pressure greater than 0.08 Torr at 22° C. is present in an amount ranging from 7.35 to 55 wt % of the fragrance component. Alternatively, the first at least one perfume raw material having a first vapor pressure greater than 0.08 Torr at 22° C. is present in an amount ranging from 7.4 to 55 wt % of the fragrance component. Alternatively, the first at least one perfume raw material having a first vapor pressure greater than 0.08 Torr at 22° C. is present in an amount ranging from 7.45 to 55 wt % of the fragrance component. Alternatively, the first at least one perfume raw material having a first vapor pressure greater than 0.08 Torr at 22° C. is present in an amount ranging from 7.5 to 55 wt % of the fragrance component. Alternatively, the first at least one perfume raw material having a first vapor pressure greater than 0.08 Torr at 22° C. is present in an amount ranging from 7.55 to 55 wt % of the fragrance component. Alternatively, the first at least one perfume raw material having a first vapor pressure greater than 0.08 Torr at 22° C. is present in an amount ranging from 7.6 to 55 wt % of the fragrance component. Alternatively, the first at least one perfume raw material having a first vapor pressure greater than 0.08 Torr at 22° C. is present in an amount ranging from 7.65 to 55 wt % of the fragrance component. Alternatively, the first at least one perfume raw material having a first vapor pressure greater than 0.08 Torr at 22° C. is present in an amount ranging from 7.7 to 55 wt % of the fragrance component. Alternatively, the first at least one perfume raw material having a first vapor pressure greater than 0.08 Torr at 22° C. is present in an amount ranging from 7.75 to 55 wt % of the fragrance component. Alternatively, the first at least one perfume raw material having a first vapor pressure greater than 0.08 Torr at 22° C. is present in an amount ranging from 7.8 to 55 wt % of the fragrance component. Alternatively, the first at least one perfume raw material having a first vapor pressure greater than 0.08 Torr at 22° C. is present in an amount ranging from 7.85 to 55 wt % of the fragrance component. Alternatively, the first at least one perfume raw material having a first vapor pressure greater than 0.08 Torr at 22° C. is present in an amount ranging from 7.9 to 55 wt % of the fragrance component. Alternatively, the first at least one perfume raw material having a first vapor pressure greater than 0.08 Torr at 22° C. is present in an amount ranging from 7.95 to 55 wt % of the fragrance component. Alternatively, the first at least one perfume raw material having a first vapor pressure greater than 0.08 Torr at 22° C. is present in an amount ranging from 8 to 55 wt % of the fragrance component. Alternatively, the first at least one perfume raw material having a first vapor pressure greater than 0.08 Torr at 22° C. is present in an amount ranging from 8.15 to 55 wt % of the fragrance component. Alternatively, the first at least one perfume raw material having a first vapor pressure greater than 0.08 Torr at 22° C. is present in an amount ranging from 8.2 to 55 wt % of the fragrance component. Alternatively, the first at least one perfume raw material having a first vapor pressure greater than 0.08 Torr at 22° C. is present in an amount ranging from 8.25 to 55 wt % of the fragrance component. Alternatively, the first at least one perfume raw material having a first vapor pressure greater than 0.08 Torr at 22° C. is present in an amount ranging from 8.3 to 55 wt % of the fragrance component. Alternatively, the first at least one perfume raw material having a first vapor pressure greater than 0.08 Torr at 22° C. is present in an amount ranging from 8.35 to 55 wt % of the fragrance component. Alternatively, the first at least one perfume raw material having a first vapor pressure greater than 0.08 Torr at 22° C. is present in an amount ranging from 8.4 to 55 wt % of the fragrance component. Alternatively, the first at least one perfume raw material having a first vapor pressure greater than 0.08 Torr at 22° C. is present in an amount ranging from 8.45 to 55 wt % of the fragrance component. Alternatively, the first at least one perfume raw material having a first vapor pressure greater than 0.08 Torr at 22° C. is present in an amount ranging from 8.5 to 55 wt % of the fragrance component. Alternatively, the first at least one perfume raw material having a first vapor pressure greater than 0.08 Torr at 22° C. is present in an amount ranging from 8.55 to 55 wt % of the fragrance component. Alternatively, the first at least one perfume raw material having a first vapor pressure greater than 0.08 Torr at 22° C. is present in an amount ranging from 8.6 to 55 wt % of the fragrance component. Alternatively, the first at least one perfume raw material having a first vapor pressure greater than 0.08 Torr at 22° C. is present in an amount ranging from 8.65 to 55 wt % of the fragrance component. Alternatively, the first at least one perfume raw material having a first vapor pressure greater than 0.08 Torr at 22° C. is present in an amount ranging from 8.7 to 55 wt % of the fragrance component. Alternatively, the first at least one perfume raw material having a first vapor pressure greater than 0.08 Torr at 22° C. is present in an amount ranging from 8.75 to 55 wt % of the fragrance component. Alternatively, the first at least one perfume raw material having a first vapor pressure greater than 0.08 Torr at 22° C. is present in an amount ranging from 8.8 to 55 wt % of the fragrance component. Alternatively, the first at least one perfume raw material having a first vapor pressure greater than 0.08 Torr at 22° C. is present in an amount ranging from 8.85 to 55 wt % of the fragrance component. Alternatively, the first at least one perfume raw material having a first vapor pressure greater than 0.08 Torr at 22° C. is present in an amount ranging from 8.9 to 55 wt % of the fragrance component. Alternatively, the first at least one perfume raw material having a first vapor pressure greater than 0.08 Torr at 22° C. is present in an amount ranging from 8.95 to 55 wt % of the fragrance component. Alternatively, the first at least one perfume raw material having a first vapor pressure greater than 0.08 Torr at 22° C. is present in an amount ranging from 9 to 55 wt % of the fragrance component. Alternatively, the first at least one perfume raw material having a first vapor pressure greater than 0.08 Torr at 22° C. is present in an amount ranging from 9.15 to 55 wt % of the fragrance component. Alternatively, the first at least one perfume raw material having a first vapor pressure greater than 0.08 Torr at 22° C. is present in an amount ranging from 9.2 to 55 wt % of the fragrance component. Alternatively, the first at least one perfume raw material having a first vapor pressure greater than 0.08 Torr at 22° C. is present in an amount ranging from 9.25 to 55 wt % of the fragrance component. Alternatively, the first at least one perfume raw material having a first vapor pressure greater than 0.08 Torr at 22° C. is present in an amount ranging from 9.3 to 55 wt % of the fragrance component. Alternatively, the first at least one perfume raw material having a first vapor pressure greater than 0.08 Torr at 22° C. is present in an amount ranging from 9.35 to 55 wt % of the fragrance component. Alternatively, the first at least one perfume raw material having a first vapor pressure greater than 0.08 Torr at 22° C. is present in an amount ranging from 9.4 to 55 wt % of the fragrance component. Alternatively, the first at least one perfume raw material having a first vapor pressure greater than 0.08 Torr at 22° C. is present in an amount ranging from 9.45 to 55 wt % of the fragrance component. Alternatively, the first at least one perfume raw material having a first vapor pressure greater than 0.08 Torr at 22° C. is present in an amount ranging from 9.5 to 55 wt % of the fragrance component. Alternatively, the first at least one perfume raw material having a first vapor pressure greater than 0.08 Torr at 22° C. is present in an amount ranging from 9.55 to 55 wt % of the fragrance component. Alternatively, the first at least one perfume raw material having a first vapor pressure greater than 0.08 Torr at 22° C. is present in an amount ranging from 9.6 to 55 wt % of the fragrance component. Alternatively, the first at least one perfume raw material having a first vapor pressure greater than 0.08 Torr at 22° C. is present in an amount ranging from 9.65 to 55 wt % of the fragrance component. Alternatively, the first at least one perfume raw material having a first vapor pressure greater than 0.08 Torr at 22° C. is present in an amount ranging from 9.7 to 55 wt % of the fragrance component. Alternatively, the first at least one perfume raw material having a first vapor pressure greater than 0.08 Torr at 22° C. is present in an amount ranging from 9.75 to 55 wt % of the fragrance component. Alternatively, the first at least one perfume raw material having a first vapor pressure greater than 0.08 Torr at 22° C. is present in an amount ranging from 9.8 to 55 wt % of the fragrance component. Alternatively, the first at least one perfume raw material having a first vapor pressure greater than 0.08 Torr at 22° C. is present in an amount ranging from 9.85 to 55 wt % of the fragrance component. Alternatively, the first at least one perfume raw material having a first vapor pressure greater than 0.08 Torr at 22° C. is present in an amount ranging from 9.9 to 55 wt % of the fragrance component. Alternatively, the first at least one perfume raw material having a first vapor pressure greater than 0.08 Torr at 22° C. is present in an amount ranging from 9.95 to 55 wt % of the fragrance component. Alternatively, the first at least one perfume raw material having a first vapor pressure greater than 0.08 Torr at 22° C. is present in an amount ranging from 10 to 55 wt % of the fragrance component. Alternatively, the first at least one perfume raw material having a first vapor pressure greater than 0.08 Torr at 22° C. is present in an amount ranging from 15 to 55 wt % of the fragrance component. Alternatively, the first at least one perfume raw material having a first vapor pressure greater than 0.08 Torr at 22° C. is present in an amount ranging from 20 to 55 wt % of the fragrance component. Alternatively, the first at least one perfume raw material having a first vapor pressure greater than 0.08 Torr at 22° C. is present in an amount ranging from 25 to 55 wt % of the fragrance component. Alternatively, the first at least one perfume raw material having a first vapor pressure greater than 0.08 Torr at 22° C. is present in an amount ranging from 30 to 55 wt % of the fragrance component. Alternatively, the first at least one perfume raw material having a first vapor pressure greater than 0.08 Torr at 22° C. is present in an amount ranging from 35 to 55 wt % of the fragrance component. Alternatively, the first at least one perfume raw material having a first vapor pressure greater than 0.08 Torr at 22° C. is present in an amount ranging from 40 to 55 wt % of the fragrance component. Alternatively, the first at least one perfume raw material having a first vapor pressure greater than 0.08 Torr at 22° C. is present in an amount ranging from 45 to 55 wt % of the fragrance component. Alternatively, the first at least one perfume raw material having a first vapor pressure greater than 0.08 Torr at 22° C. is present in an amount ranging from 50 to 55 wt % of the fragrance component.

Alternatively, the first at least one perfume raw material having a first vapor pressure greater than 0.08 Torr at 22° C. is present in an amount ranging from 0.08 to 50 wt % of the fragrance component. Alternatively, the first at least one perfume raw material having a first vapor pressure greater than 0.08 Torr at 22° C. is present in an amount ranging from 0.08 to 45 wt % of the fragrance component. Alternatively, the first at least one perfume raw material having a first vapor pressure greater than 0.08 Torr at 22° C. is present in an amount ranging from 0.08 to 40 wt % of the fragrance component. Alternatively, the first at least one perfume raw material having a first vapor pressure greater than 0.08 Torr at 22° C. is present in an amount ranging from 0.08 to 35 wt % of the fragrance component. Alternatively, the first at least one perfume raw material having a first vapor pressure greater than 0.08 Torr at 22° C. is present in an amount ranging from 0.08 to 30 wt % of the fragrance component. Alternatively, the first at least one perfume raw material having a first vapor pressure greater than 0.08 Torr at 22° C. is present in an amount ranging from 0.08 to 25 wt % of the fragrance component. Alternatively, the first at least one perfume raw material having a first vapor pressure greater than 0.08 Torr at 22° C. is present in an amount ranging from 0.08 to 20 wt % of the fragrance component. Alternatively, the first at least one perfume raw material having a first vapor pressure greater than 0.08 Torr at 22° C. is present in an amount ranging from 0.08 to 15 wt % of the fragrance component. Alternatively, the first at least one perfume raw material having a first vapor pressure greater than 0.08 Torr at 22° C. is present in an amount ranging from 0.08 to 10 wt % of the fragrance component. Alternatively, the first at least one perfume raw material having a first vapor pressure greater than 0.08 Torr at 22° C. is present in an amount ranging from 0.08 to 9.9 wt % of the fragrance component. Alternatively, the first at least one perfume raw material having a first vapor pressure greater than 0.08 Torr at 22° C. is present in an amount ranging from 0.08 to 9.8 wt % of the fragrance component. Alternatively, the first at least one perfume raw material having a first vapor pressure greater than 0.08 Torr at 22° C. is present in an amount ranging from 0.08 to 9.7 wt % of the fragrance component. Alternatively, the first at least one perfume raw material having a first vapor pressure greater than 0.08 Torr at 22° C. is present in an amount ranging from 0.08 to 9.6 wt % of the fragrance component. Alternatively, the first at least one perfume raw material having a first vapor pressure greater than 0.08 Torr at 22° C. is present in an amount ranging from 0.08 to 9.5 wt % of the fragrance component. Alternatively, the first at least one perfume raw material having a first vapor pressure greater than 0.08 Torr at 22° C. is present in an amount ranging from 0.08 to 9.4 wt % of the fragrance component. Alternatively, the first at least one perfume raw material having a first vapor pressure greater than 0.08 Torr at 22° C. is present in an amount ranging from 0.08 to 9.3 wt % of the fragrance component. Alternatively, the first at least one perfume raw material having a first vapor pressure greater than 0.08 Torr at 22° C. is present in an amount ranging from 0.08 to 9.2 wt % of the fragrance component. Alternatively, the first at least one perfume raw material having a first vapor pressure greater than 0.08 Torr at 22° C. is present in an amount ranging from 0.08 to 9.1 wt % of the fragrance component. Alternatively, the first at least one perfume raw material having a first vapor pressure greater than 0.08 Torr at 22° C. is present in an amount ranging from 0.08 to 9 wt % of the fragrance component. Alternatively, the first at least one perfume raw material having a first vapor pressure greater than 0.08 Torr at 22° C. is present in an amount ranging from 0.08 to 8.9 wt % of the fragrance component. Alternatively, the first at least one perfume raw material having a first vapor pressure greater than 0.08 Torr at 22° C. is present in an amount ranging from 0.08 to 8.8 wt % of the fragrance component. Alternatively, the first at least one perfume raw material having a first vapor pressure greater than 0.08 Torr at 22° C. is present in an amount ranging from 0.08 to 8.7 wt % of the fragrance component. Alternatively, the first at least one perfume raw material having a first vapor pressure greater than 0.08 Torr at 22° C. is present in an amount ranging from 0.08 to 8.6 wt % of the fragrance component. Alternatively, the first at least one perfume raw material having a first vapor pressure greater than 0.08 Torr at 22° C. is present in an amount ranging from 0.08 to 8.5 wt % of the fragrance component. Alternatively, the first at least one perfume raw material having a first vapor pressure greater than 0.08 Torr at 22° C. is present in an amount ranging from 0.08 to 8.4 wt % of the fragrance component. Alternatively, the first at least one perfume raw material having a first vapor pressure greater than 0.08 Torr at 22° C. is present in an amount ranging from 0.08 to 8.3 wt % of the fragrance component. Alternatively, the first at least one perfume raw material having a first vapor pressure greater than 0.08 Torr at 22° C. is present in an amount ranging from 0.08 to 8.2 wt % of the fragrance component. Alternatively, the first at least one perfume raw material having a first vapor pressure greater than 0.08 Torr at 22° C. is present in an amount ranging from 0.08 to 8.1 wt % of the fragrance component. Alternatively, the first at least one perfume raw material having a first vapor pressure greater than 0.08 Torr at 22° C. is present in an amount ranging from 0.08 to 8 wt % of the fragrance component. Alternatively, the first at least one perfume raw material having a first vapor pressure greater than 0.08 Torr at 22° C. is present in an amount ranging from 0.08 to 7.9 wt % of the fragrance component. Alternatively, the first at least one perfume raw material having a first vapor pressure greater than 0.08 Torr at 22° C. is present in an amount ranging from 0.08 to 7.8 wt % of the fragrance component. Alternatively, the first at least one perfume raw material having a first vapor pressure greater than 0.08 Torr at 22° C. is present in an amount ranging from 0.08 to 7.7 wt % of the fragrance component. Alternatively, the first at least one perfume raw material having a first vapor pressure greater than 0.08 Torr at 22° C. is present in an amount ranging from 0.08 to 7.6 wt % of the fragrance component. Alternatively, the first at least one perfume raw material having a first vapor pressure greater than 0.08 Torr at 22° C. is present in an amount ranging from 0.08 to 7.5 wt % of the fragrance component. Alternatively, the first at least one perfume raw material having a first vapor pressure greater than 0.08 Torr at 22° C. is present in an amount ranging from 0.08 to 7.4 wt % of the fragrance component. Alternatively, the first at least one perfume raw material having a first vapor pressure greater than 0.08 Torr at 22° C. is present in an amount ranging from 0.08 to 7.3 wt % of the fragrance component. Alternatively, the first at least one perfume raw material having a first vapor pressure greater than 0.08 Torr at 22° C. is present in an amount ranging from 0.08 to 7.2 wt % of the fragrance component. Alternatively, the first at least one perfume raw material having a first vapor pressure greater than 0.08 Torr at 22° C. is present in an amount ranging from 0.08 to 7.1 wt % of the fragrance component. Alternatively, the first at least one perfume raw material having a first vapor pressure greater than 0.08 Torr at 22° C. is present in an amount ranging from 0.08 to 7 wt % of the fragrance component. Alternatively, the first at least one perfume raw material having a first vapor pressure greater than 0.08 Torr at 22° C. is present in an amount ranging from 0.08 to 6.9 wt % of the fragrance component. Alternatively, the first at least one perfume raw material having a first vapor pressure greater than 0.08 Torr at 22° C. is present in an amount ranging from 0.08 to 6.8 wt % of the fragrance component. Alternatively, the first at least one perfume raw material having a first vapor pressure greater than 0.08 Torr at 22° C. is present in an amount ranging from 0.08 to 6.7 wt % of the fragrance component. Alternatively, the first at least one perfume raw material having a first vapor pressure greater than 0.08 Torr at 22° C. is present in an amount ranging from 0.08 to 6.6 wt % of the fragrance component. Alternatively, the first at least one perfume raw material having a first vapor pressure greater than 0.08 Torr at 22° C. is present in an amount ranging from 0.08 to 6.5 wt % of the fragrance component. Alternatively, the first at least one perfume raw material having a first vapor pressure greater than 0.08 Torr at 22° C. is present in an amount ranging from 0.08 to 6.4 wt % of the fragrance component. Alternatively, the first at least one perfume raw material having a first vapor pressure greater than 0.08 Torr at 22° C. is present in an amount ranging from 0.08 to 6.3 wt % of the fragrance component. Alternatively, the first at least one perfume raw material having a first vapor pressure greater than 0.08 Torr at 22° C. is present in an amount ranging from 0.08 to 6.2 wt % of the fragrance component. Alternatively, the first at least one perfume raw material having a first vapor pressure greater than 0.08 Torr at 22° C. is present in an amount ranging from 0.08 to 6.1 wt % of the fragrance component. Alternatively, the first at least one perfume raw material having a first vapor pressure greater than 0.08 Torr at 22° C. is present in an amount ranging from 0.08 to 6 wt % of the fragrance component. Alternatively, the first at least one perfume raw material having a first vapor pressure greater than 0.08 Torr at 22° C. is present in an amount ranging from 0.08 to 5.9 wt % of the fragrance component. Alternatively, the first at least one perfume raw material having a first vapor pressure greater than 0.08 Torr at 22° C. is present in an amount ranging from 0.08 to 5.8 wt % of the fragrance component. Alternatively, the first at least one perfume raw material having a first vapor pressure greater than 0.08 Torr at 22° C. is present in an amount ranging from 0.08 to 5.7 wt % of the fragrance component. Alternatively, the first at least one perfume raw material having a first vapor pressure greater than 0.08 Torr at 22° C. is present in an amount ranging from 0.08 to 5.6 wt % of the fragrance component. Alternatively, the first at least one perfume raw material having a first vapor pressure greater than 0.08 Torr at 22° C. is present in an amount ranging from 0.08 to 5.5 wt % of the fragrance component. Alternatively, the first at least one perfume raw material having a first vapor pressure greater than 0.08 Torr at 22° C. is present in an amount ranging from 0.08 to 5.4 wt % of the fragrance component. Alternatively, the first at least one perfume raw material having a first vapor pressure greater than 0.08 Torr at 22° C. is present in an amount ranging from 0.08 to 5.3 wt % of the fragrance component. Alternatively, the first at least one perfume raw material having a first vapor pressure greater than 0.08 Torr at 22° C. is present in an amount ranging from 0.08 to 5.2 wt % of the fragrance component. Alternatively, the first at least one perfume raw material having a first vapor pressure greater than 0.08 Torr at 22° C. is present in an amount ranging from 0.08 to 5.1 wt % of the fragrance component. Alternatively, the first at least one perfume raw material having a first vapor pressure greater than 0.08 Torr at 22° C. is present in an amount ranging from 0.08 to 5 wt % of the fragrance component. Alternatively, the first at least one perfume raw material having a first vapor pressure greater than 0.08 Torr at 22° C. is present in an amount ranging from 0.08 to 4.9 wt % of the fragrance component. Alternatively, the first at least one perfume raw material having a first vapor pressure greater than 0.08 Torr at 22° C. is present in an amount ranging from 0.08 to 4.8 wt % of the fragrance component. Alternatively, the first at least one perfume raw material having a first vapor pressure greater than 0.08 Torr at 22° C. is present in an amount ranging from 0.08 to 4.7 wt % of the fragrance component. Alternatively, the first at least one perfume raw material having a first vapor pressure greater than 0.08 Torr at 22° C. is present in an amount ranging from 0.08 to 4.6 wt % of the fragrance component. Alternatively, the first at least one perfume raw material having a first vapor pressure greater than 0.08 Torr at 22° C. is present in an amount ranging from 0.08 to 4.5 wt % of the fragrance component. Alternatively, the first at least one perfume raw material having a first vapor pressure greater than 0.08 Torr at 22° C. is present in an amount ranging from 0.08 to 4.4 wt % of the fragrance component. Alternatively, the first at least one perfume raw material having a first vapor pressure greater than 0.08 Torr at 22° C. is present in an amount ranging from 0.08 to 4.3 wt % of the fragrance component. Alternatively, the first at least one perfume raw material having a first vapor pressure greater than 0.08 Torr at 22° C. is present in an amount ranging from 0.08 to 4.2 wt % of the fragrance component. Alternatively, the first at least one perfume raw material having a first vapor pressure greater than 0.08 Torr at 22° C. is present in an amount ranging from 0.08 to 4.1 wt % of the fragrance component. Alternatively, the first at least one perfume raw material having a first vapor pressure greater than 0.08 Torr at 22° C. is present in an amount ranging from 0.08 to 4 wt % of the fragrance component. Alternatively, the first at least one perfume raw material having a first vapor pressure greater than 0.08 Torr at 22° C. is present in an amount ranging from 0.08 to 3.9 wt % of the fragrance component. Alternatively, the first at least one perfume raw material having a first vapor pressure greater than 0.08 Torr at 22° C. is present in an amount ranging from 0.08 to 3.8 wt % of the fragrance component. Alternatively, the first at least one perfume raw material having a first vapor pressure greater than 0.08 Torr at 22° C. is present in an amount ranging from 0.08 to 3.7 wt % of the fragrance component. Alternatively, the first at least one perfume raw material having a first vapor pressure greater than 0.08 Torr at 22° C. is present in an amount ranging from 0.08 to 3.6 wt % of the fragrance component. Alternatively, the first at least one perfume raw material having a first vapor pressure greater than 0.08 Torr at 22° C. is present in an amount ranging from 0.08 to 3.5 wt % of the fragrance component. Alternatively, the first at least one perfume raw material having a first vapor pressure greater than 0.08 Torr at 22° C. is present in an amount ranging from 0.08 to 3.4 wt % of the fragrance component. Alternatively, the first at least one perfume raw material having a first vapor pressure greater than 0.08 Torr at 22° C. is present in an amount ranging from 0.08 to 3.3 wt % of the fragrance component. Alternatively, the first at least one perfume raw material having a first vapor pressure greater than 0.08 Torr at 22° C. is present in an amount ranging from 0.08 to 3.2 wt % of the fragrance component. Alternatively, the first at least one perfume raw material having a first vapor pressure greater than 0.08 Torr at 22° C. is present in an amount ranging from 0.08 to 3.1 wt % of the fragrance component. Alternatively, the first at least one perfume raw material having a first vapor pressure greater than 0.08 Torr at 22° C. is present in an amount ranging from 0.08 to 3 wt % of the fragrance component. Alternatively, the first at least one perfume raw material having a first vapor pressure greater than 0.08 Torr at 22° C. is present in an amount ranging from 0.08 to 2.9 wt % of the fragrance component. Alternatively, the first at least one perfume raw material having a first vapor pressure greater than 0.08 Torr at 22° C. is present in an amount ranging from 0.08 to 2.8 wt % of the fragrance component. Alternatively, the first at least one perfume raw material having a first vapor pressure greater than 0.08 Torr at 22° C. is present in an amount ranging from 0.08 to 2.7 wt % of the fragrance component. Alternatively, the first at least one perfume raw material having a first vapor pressure greater than 0.08 Torr at 22° C. is present in an amount ranging from 0.08 to 2.6 wt % of the fragrance component. Alternatively, the first at least one perfume raw material having a first vapor pressure greater than 0.08 Torr at 22° C. is present in an amount ranging from 0.08 to 2.5 wt % of the fragrance component. Alternatively, the first at least one perfume raw material having a first vapor pressure greater than 0.08 Torr at 22° C. is present in an amount ranging from 0.08 to 2.4 wt % of the fragrance component. Alternatively, the first at least one perfume raw material having a first vapor pressure greater than 0.08 Torr at 22° C. is present in an amount ranging from 0.08 to 2.3 wt % of the fragrance component. Alternatively, the first at least one perfume raw material having a first vapor pressure greater than 0.08 Torr at 22° C. is present in an amount ranging from 0.08 to 2.2 wt % of the fragrance component. Alternatively, the first at least one perfume raw material having a first vapor pressure greater than 0.08 Torr at 22° C. is present in an amount ranging from 0.08 to 2.1 wt % of the fragrance component. Alternatively, the first at least one perfume raw material having a first vapor pressure greater than 0.08 Torr at 22° C. is present in an amount ranging from 0.08 to 2 wt % of the fragrance component. Alternatively, the first at least one perfume raw material having a first vapor pressure greater than 0.08 Torr at 22° C. is present in an amount ranging from 0.08 to 1.9 wt % of the fragrance component. Alternatively, the first at least one perfume raw material having a first vapor pressure greater than 0.08 Torr at 22° C.

is present in an amount ranging from 0.08 to 1.8 wt % of the fragrance component. Alternatively, the first at least one perfume raw material having a first vapor pressure greater than 0.08 Torr at 22° C. is present in an amount ranging from 0.08 to 1.7 wt % of the fragrance component. Alternatively, the first at least one perfume raw material having a first vapor pressure greater than 0.08 Torr at 22° C. is present in an amount ranging from 0.08 to 1.6 wt % of the fragrance component. Alternatively, the first at least one perfume raw material having a first vapor pressure greater than 0.08 Torr at 22° C. is present in an amount ranging from 0.08 to 1.5 wt % of the fragrance component. Alternatively, the first at least one perfume raw material having a first vapor pressure greater than 0.08 Torr at 22° C. is present in an amount ranging from 0.08 to 1.4 wt % of the fragrance component. Alternatively, the first at least one perfume raw material having a first vapor pressure greater than 0.08 Torr at 22° C. is present in an amount ranging from 0.08 to 1.3 wt % of the fragrance component. Alternatively, the first at least one perfume raw material having a first vapor pressure greater than 0.08 Torr at 22° C. is present in an amount ranging from 0.08 to 1.2 wt % of the fragrance component. Alternatively, the first at least one perfume raw material having a first vapor pressure greater than 0.08 Torr at 22° C. is present in an amount ranging from 0.08 to 1.1 wt % of the fragrance component. Alternatively, the first at least one perfume raw material having a first vapor pressure greater than 0.08 Torr at 22° C. is present in an amount ranging from 0.08 to 1 wt % of the fragrance component. Alternatively, the first at least one perfume raw material having a first vapor pressure greater than 0.08 Torr at 22° C. is present in an amount ranging from 0.08 to 0.9 wt % of the fragrance component. Alternatively, the first at least one perfume raw material having a first vapor pressure greater than 0.08 Torr at 22° C. is present in an amount ranging from 0.08 to 0.8 wt % of the fragrance component. Alternatively, the first at least one perfume raw material having a first vapor pressure greater than 0.08 Torr at 22° C. is present in an amount ranging from 0.08 to 0.7 wt % of the fragrance component. Alternatively, the first at least one perfume raw material having a first vapor pressure greater than 0.08 Torr at 22° C. is present in an amount ranging from 0.08 to 0.6 wt % of the fragrance component. Alternatively, the first at least one perfume raw material having a first vapor pressure greater than 0.08 Torr at 22° C. is present in an amount ranging from 0.08 to 0.5 wt % of the fragrance component. Alternatively, the first at least one perfume raw material having a first vapor pressure greater than 0.08 Torr at 22° C. is present in an amount ranging from 0.08 to 0.4 wt % of the fragrance component. Alternatively, the first at least one perfume raw material having a first vapor pressure greater than 0.08 Torr at 22° C. is present in an amount ranging from 0.08 to 0.3 wt % of the fragrance component. Alternatively, the first at least one perfume raw material having a first vapor pressure greater than 0.08 Torr at 22° C. is present in an amount ranging from 0.08 to 0.2 wt % of the fragrance component. Alternatively, the first at least one perfume raw material having a first vapor pressure greater than 0.08 Torr at 22° C. is present in an amount ranging from 0.08 to 0.1 wt % of the fragrance component. Alternatively, the first at least one perfume raw material having a first vapor pressure greater than 0.08 Torr at 22° C. is present in an amount ranging from 0.08 to 0.09 wt % of the fragrance component.

In some aspects, the first at least one perfume raw material having a first vapor pressure greater than 0.08 Torr at 22° C. is present at 0.008, 0.009, 0.01, 0.015, 0.02, 0.025, 0.03, 0.035, 0.04, 0.045, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 4.15, 4.2, 4.25, 4.3, 4.35, 4.4, 4.45, 4.5, 4.55, 4.6, 4.65, 4.7, 4.75, 4.8, 4.85, 4.9, 4.95, 5, 5.15, 5.2, 5.25, 5.3, 5.35, 5.4, 5.45, 5.5, 5.55, 5.6, 5.65, 5.7, 5.75, 5.8, 5.85, 5.9, 5.95, 6, 6.15, 6.2, 6.25, 6.3, 6.35, 6.4, 6.45, 6.5, 6.55, 6.6, 6.65, 6.7, 6.75, 6.8, 6.85, 6.9, 6.95, 7, 7.15, 7.2, 7.25, 7.3, 7.35, 7.4, 7.45, 7.5, 7.55, 7.6, 7.65, 7.7, 7.75, 7.8, 7.85, 7.9, 7.95, 8, 8.15, 8.2, 8.25, 8.3, 8.35, 8.4, 8.45, 8.5, 8.55, 8.6, 8.65, 8.7, 8.75, 8.8, 8.85, 8.9, 8.95, 9, 9.15, 9.2, 9.25, 9.3, 9.35, 9.4, 9.45, 9.5, 9.55, 9.6, 9.65, 9.7, 9.75, 9.8, 9.85, 9.9, 9.95, 10, 15, 20, 25, 30, 35, 40, 45, 50, or 55 wt % of the fragrance component.

In one aspect, the medium volatility component consists of only the first at least one perfume raw material having a first vapor pressure range of 0.0008 to 0.08 Torr at 22° C. In these aspects, first at least one perfume raw material having a first vapor pressure range of 0.0008 to 0.08 Torr at 22° C. is present in an amount ranging from 0.08 to 85 wt % of the fragrance component. Alternatively, first at least one perfume raw material having a first vapor pressure range of 0.0008 to 0.08 Torr at 22° C. is present in an amount ranging from 0.1 to 85 wt % of the fragrance component. Alternatively, first at least one perfume raw material having a first vapor pressure range of 0.0008 to 0.08 Torr at 22° C. is present in an amount ranging from 0.15 to 85 wt % of the fragrance component. Alternatively, first at least one perfume raw material having a first vapor pressure range of 0.0008 to 0.08 Torr at 22° C. is present in an amount ranging from 0.2 to 85 wt % of the fragrance component. Alternatively, first at least one perfume raw material having a first vapor pressure range of 0.0008 to 0.08 Torr at 22° C. is present in an amount ranging from 0.25 to 85 wt % of the fragrance component. Alternatively, first at least one perfume raw material having a first vapor pressure range of 0.0008 to 0.08 Torr at 22° C. is present in an amount ranging from 0.3 to 85 wt % of the fragrance component. Alternatively, first at least one perfume raw material having a first vapor pressure range of 0.0008 to 0.08 Torr at 22° C. is present in an amount ranging from 0.35 to 85 wt % of the fragrance component. Alternatively, first at least one perfume raw material having a first vapor pressure range of 0.0008 to 0.08 Torr at 22° C. is present in an amount ranging from 0.4 to 85 wt % of the fragrance component. Alternatively, first at least one perfume raw material having a first vapor pressure range of 0.0008 to 0.08 Torr at 22° C. is present in an amount ranging from 0.45 to 85 wt % of the fragrance component. Alternatively, first at least one perfume raw material having a first vapor pressure range of 0.0008 to 0.08 Torr at 22° C. is present in an amount ranging from 0.5 to 85 wt % of the fragrance component. Alternatively, first at least one perfume raw material having a first vapor pressure range of 0.0008 to 0.08 Torr at 22° C. is present in an amount ranging from 0.55 to 85 wt % of the fragrance component. Alternatively, first at least one perfume raw material having a first vapor pressure range of 0.0008 to 0.08 Torr at 22° C. is present in an amount ranging from 0.6 to 85 wt % of the fragrance component. Alternatively, first at least one perfume raw material having a first vapor pressure range of 0.0008 to 0.08 Torr at 22° C. is present in an amount ranging from 0.65 to 85 wt % of the fragrance component. Alternatively, first at least one perfume raw material having a first vapor pressure range of 0.0008 to 0.08 Torr at 22° C. is present in an amount ranging from 0.7 to 85 wt % of the fragrance component. Alternatively, first at least one perfume raw material having a first vapor pressure range of 0.0008 to 0.08 Torr at 22° C. is present in an amount ranging from 0.75 to 85 wt % of the fragrance component. Alternatively, first at least one perfume raw material having a first vapor pressure range of 0.0008 to 0.08 Torr at 22° C. is present in an amount ranging from 0.8 to 85 wt % of the fragrance component. Alternatively, first at least one perfume raw material having a first vapor pressure range of 0.0008 to 0.08 Torr at 22° C. is present in an amount ranging from 0.85 to 85 wt % of the fragrance component. Alternatively, first at least one perfume raw material having a first vapor pressure range of 0.0008 to 0.08 Torr at 22° C. is present in an amount ranging from 0.9 to 85 wt % of the fragrance component. Alternatively, first at least one perfume raw material having a first vapor pressure range of 0.0008 to 0.08 Torr at 22° C. is present in an amount ranging from 0.95 to 85 wt % of the fragrance component. Alternatively, first at least one perfume raw material having a first vapor pressure range of 0.0008 to 0.08 Torr at 22° C. is present in an amount ranging from 1 to 85 wt % of the fragrance component. Alternatively, first at least one perfume raw material having a first vapor pressure range of 0.0008 to 0.08 Torr at 22° C. is present in an amount ranging from 1.15 to 85 wt % of the fragrance component. Alternatively, first at least one perfume raw material having a first vapor pressure range of 0.0008 to 0.08 Torr at 22° C. is present in an amount ranging from 1.2 to 85 wt % of the fragrance component. Alternatively, first at least one perfume raw material having a first vapor pressure range of 0.0008 to 0.08 Torr at 22° C. is present in an amount ranging from 1.25 to 85 wt % of the fragrance component. Alternatively, first at least one perfume raw material having a first vapor pressure range of 0.0008 to 0.08 Torr at 22° C. is present in an amount ranging from 1.3 to 85 wt % of the fragrance component. Alternatively, first at least one perfume raw material having a first vapor pressure range of 0.0008 to 0.08 Torr at 22° C. is present in an amount ranging from 1.35 to 85 wt % of the fragrance component. Alternatively, first at least one perfume raw material having a first vapor pressure range of 0.0008 to 0.08 Torr at 22° C. is present in an amount ranging from 1.4 to 85 wt % of the fragrance component. Alternatively, first at least one perfume raw material having a first vapor pressure range of 0.0008 to 0.08 Torr at 22° C. is present in an amount ranging from 1.45 to 85 wt % of the fragrance component. Alternatively, first at least one perfume raw material having a first vapor pressure range of 0.0008 to 0.08 Torr at 22° C. is present in an amount ranging from 1.5 to 85 wt % of the fragrance component. Alternatively, first at least one perfume raw material having a first vapor pressure range of 0.0008 to 0.08 Torr at 22° C. is present in an amount ranging from 1.55 to 85 wt % of the fragrance component. Alternatively, first at least one perfume raw material having a first vapor pressure range of 0.0008 to 0.08 Torr at 22° C. is present in an amount ranging from 1.6 to 85 wt % of the fragrance component. Alternatively, first at least one perfume raw material having a first vapor pressure range of 0.0008 to 0.08 Torr at 22° C. is present in an amount ranging from 1.65 to 85 wt % of the fragrance component. Alternatively, first at least one perfume raw material having a first vapor pressure range of 0.0008 to 0.08 Torr at 22° C. is present in an amount ranging from 1.7 to 85 wt % of the fragrance component. Alternatively, first at least one perfume raw material having a first vapor pressure range of 0.0008 to 0.08 Torr at 22° C. is present in an amount ranging from 1.75 to 85 wt % of the fragrance component. Alternatively, first at least one perfume raw material having a first vapor pressure range of 0.0008 to 0.08 Torr at 22° C. is present in an amount ranging from 1.8 to 85 wt % of the fragrance component. Alternatively, first at least one perfume raw material having a first vapor pressure range of 0.0008 to 0.08 Torr at 22° C. is present in an amount ranging from 1.85 to 85 wt % of the fragrance component. Alternatively, first at least one perfume raw material having a first vapor pressure range of 0.0008 to 0.08 Torr at 22° C. is present in an amount ranging from 1.9 to 85 wt % of the fragrance component. Alternatively, first at least one perfume raw material having a first vapor pressure range of 0.0008 to 0.08 Torr at 22° C. is present in an amount ranging from 1.95 to 85 wt % of the fragrance component. Alternatively, first at least one perfume raw material having a first vapor pressure range of 0.0008 to 0.08 Torr at 22° C. is present in an amount ranging from 2 to 85 wt % of the fragrance component. Alternatively, first at least one perfume raw material having a first vapor pressure range of 0.0008 to 0.08 Torr at 22° C. is present in an amount ranging from 2.15 to 85 wt % of the fragrance component. Alternatively, first at least one perfume raw material having a first vapor pressure range of 0.0008 to 0.08 Torr at 22° C. is present in an amount ranging from 2.2 to 85 wt % of the fragrance component. Alternatively, first at least one perfume raw material having a first vapor pressure range of 0.0008 to 0.08 Torr at 22° C. is present in an amount ranging from 2.25 to 85 wt % of the fragrance component. Alternatively, first at least one perfume raw material having a first vapor pressure range of 0.0008 to 0.08 Torr at 22° C. is present in an amount ranging from 2.3 to 85 wt % of the fragrance component. Alternatively, first at least one perfume raw material having a first vapor pressure range of 0.0008 to 0.08 Torr at 22° C. is present in an amount ranging from 2.35 to 85 wt % of the fragrance component. Alternatively, first at least one perfume raw material having a first vapor pressure range of 0.0008 to 0.08 Torr at 22° C. is present in an amount ranging from 2.4 to 85 wt % of the fragrance component. Alternatively, first at least one perfume raw material having a first vapor pressure range of 0.0008 to 0.08 Torr at 22° C. is present in an amount ranging from 2.45 to 85 wt % of the fragrance component. Alternatively, first at least one perfume raw material having a first vapor pressure range of 0.0008 to 0.08 Torr at 22° C. is present in an amount ranging from 2.5 to 85 wt % of the fragrance component. Alternatively, first at least one perfume raw material having a first vapor pressure range of 0.0008 to 0.08 Torr at 22° C. is present in an amount ranging from 2.55 to 85 wt % of the fragrance component. Alternatively, first at least one perfume raw material having a first vapor pressure range of 0.0008 to 0.08 Torr at 22° C. is present in an amount ranging from 2.6 to 85 wt % of the fragrance component. Alternatively, first at least one perfume raw material having a first vapor pressure range of 0.0008 to 0.08 Torr at 22° C. is present in an amount ranging from 2.65 to 85 wt % of the fragrance component. Alternatively, first at least one perfume raw material having a first vapor pressure range of 0.0008 to 0.08 Torr at 22° C. is present in an amount ranging from 2.7 to 85 wt % of the fragrance component. Alternatively, first at least one perfume raw material having a first vapor pressure range of 0.0008 to 0.08 Torr at 22° C. is present in an amount ranging from 2.75 to 85 wt % of the fragrance component. Alternatively, first at least one perfume raw material having a first vapor pressure range of 0.0008 to 0.08 Torr at 22° C. is present in an amount ranging from 2.8 to 85 wt % of the fragrance component. Alternatively, first at least one perfume raw material having a first vapor pressure range of 0.0008 to 0.08 Torr at 22° C. is present in an amount ranging from 2.85 to 85 wt % of the fragrance component. Alternatively, first at least one perfume raw material having a first vapor pressure range of 0.0008 to 0.08 Torr at 22° C. is present in an amount ranging from 2.9 to 85 wt % of the fragrance component. Alternatively, first at least one perfume raw material having a first vapor pressure range of 0.0008 to 0.08 Torr at 22° C. is present in an amount ranging from 2.95 to 85 wt % of the fragrance component. Alternatively, first at least one perfume raw material having a first vapor pressure range of 0.0008 to 0.08 Torr at 22° C. is present in an amount ranging from 3 to 85 wt % of the fragrance component. Alternatively, first at least one perfume raw material having a first vapor pressure range of 0.0008 to 0.08 Torr at 22° C. is present in an amount ranging from 3.15 to 85 wt % of the fragrance component. Alternatively, first at least one perfume raw material having a first vapor pressure range of 0.0008 to 0.08 Torr at 22° C. is present in an amount ranging from 3.2 to 85 wt % of the fragrance component. Alternatively, first at least one perfume raw material having a first vapor pressure range of 0.0008 to 0.08 Torr at 22° C. is present in an amount ranging from 3.25 to 85 wt % of the fragrance component. Alternatively, first at least one perfume raw material having a first vapor pressure range of 0.0008 to 0.08 Torr at 22° C. is present in an amount ranging from 3.3 to 85 wt % of the fragrance component. Alternatively, first at least one perfume raw material having a first vapor pressure range of 0.0008 to 0.08 Torr at 22° C. is present in an amount ranging from 3.35 to 85 wt % of the fragrance component. Alternatively, first at least one perfume raw material having a first vapor pressure range of 0.0008 to 0.08 Torr at 22° C. is present in an amount ranging from 3.4 to 85 wt % of the fragrance component. Alternatively, first at least one perfume raw material having a first vapor pressure range of 0.0008 to 0.08 Torr at 22° C. is present in an amount ranging from 3.45 to 85 wt % of the fragrance component. Alternatively, first at least one perfume raw material having a first vapor pressure range of 0.0008 to 0.08 Torr at 22° C. is present in an amount ranging from 3.5 to 85 wt % of the fragrance component. Alternatively, first at least one perfume raw material having a first vapor pressure range of 0.0008 to 0.08 Torr at 22° C. is present in an amount ranging from 3.55 to 85 wt % of the fragrance component. Alternatively, first at least one perfume raw material having a first vapor pressure range of 0.0008 to 0.08 Torr at 22° C. is present in an amount ranging from 3.6 to 85 wt % of the fragrance component. Alternatively, first at least one perfume raw material having a first vapor pressure range of 0.0008 to 0.08 Torr at 22° C. is present in an amount ranging from 3.65 to 85 wt % of the fragrance component. Alternatively, first at least one perfume raw material having a first vapor pressure range of 0.0008 to 0.08 Torr at 22° C. is present in an amount ranging from 3.7 to 85 wt % of the fragrance component. Alternatively, first at least one perfume raw material having a first vapor pressure range of 0.0008 to 0.08 Torr at 22° C. is present in an amount ranging from 3.75 to 85 wt % of the fragrance component. Alternatively, first at least one perfume raw material having a first vapor pressure range of 0.0008 to 0.08 Torr at 22° C. is present in an amount ranging from 3.8 to 85 wt % of the fragrance component. Alternatively, first at least one perfume raw material having a first vapor pressure range of 0.0008 to 0.08 Torr at 22° C. is present in an amount ranging from 3.85 to 85 wt % of the fragrance component. Alternatively, first at least one perfume raw material having a first vapor pressure range of 0.0008 to 0.08 Torr at 22° C. is present in an amount ranging from 3.9 to 85 wt % of the fragrance component. Alternatively, first at least one perfume raw material having a first vapor pressure range of 0.0008 to 0.08 Torr at 22° C. is present in an amount ranging from 3.95 to 85 wt % of the fragrance component. Alternatively, first at least one perfume raw material having a first vapor pressure range of 0.0008 to 0.08 Torr at 22° C. is present in an amount ranging from 4 to 85 wt % of the fragrance component. Alternatively, first at least one perfume raw material having a first vapor pressure range of 0.0008 to 0.08 Torr at 22° C. is present in an amount ranging from 4.15 to 85 wt % of the fragrance component. Alternatively, first at least one perfume raw material having a first vapor pressure range of 0.0008 to 0.08 Torr at 22° C. is present in an amount ranging from 4.2 to 85 wt % of the fragrance component. Alternatively, first at least one perfume raw material having a first vapor pressure range of 0.0008 to 0.08 Torr at 22° C. is present in an amount ranging from 4.25 to 85 wt % of the fragrance component. Alternatively, first at least one perfume raw material having a first vapor pressure range of 0.0008 to 0.08 Torr at 22° C. is present in an amount ranging from 4.3 to 85 wt % of the fragrance component. Alternatively, first at least one perfume raw material having a first vapor pressure range of 0.0008 to 0.08 Torr at 22° C. is present in an amount ranging from 4.35 to 85 wt % of the fragrance component. Alternatively, first at least one perfume raw material having a first vapor pressure range of 0.0008 to 0.08 Torr at 22° C. is present in an amount ranging from 4.4 to 85 wt % of the fragrance component. Alternatively, first at least one perfume raw material having a first vapor pressure range of 0.0008 to 0.08 Torr at 22° C. is present in an amount ranging from 4.45 to 85 wt % of the fragrance component. Alternatively, first at least one perfume raw material having a first vapor pressure range of 0.0008 to 0.08 Torr at 22° C. is present in an amount ranging from 4.5 to 85 wt % of the fragrance component. Alternatively, first at least one perfume raw material having a first vapor pressure range of 0.0008 to 0.08 Torr at 22° C. is present in an amount ranging from 4.55 to 85 wt % of the fragrance component. Alternatively, first at least one perfume raw material having a first vapor pressure range of 0.0008 to 0.08 Torr at 22° C. is present in an amount ranging from 4.6 to 85 wt % of the fragrance component. Alternatively, first at least one perfume raw material having a first vapor pressure range of 0.0008 to 0.08 Torr at 22° C. is present in an amount ranging from 4.65 to 85 wt % of the fragrance component. Alternatively, first at least one perfume raw material having a first vapor pressure range of 0.0008 to 0.08 Torr at 22° C. is present in an amount ranging from 4.7 to 85 wt % of the fragrance component. Alternatively, first at least one perfume raw material having a first vapor pressure range of 0.0008 to 0.08 Torr at 22° C. is present in an amount ranging from 4.75 to 85 wt % of the fragrance component. Alternatively, first at least one perfume raw material having a first vapor pressure range of 0.0008 to 0.08 Torr at 22° C. is present in an amount ranging from 4.8 to 85 wt % of the fragrance component. Alternatively, first at least one perfume raw material having a first vapor pressure range of 0.0008 to 0.08 Torr at 22° C. is present in an amount ranging from 4.85 to 85 wt % of the fragrance component. Alternatively, first at least one perfume raw material having a first vapor pressure range of 0.0008 to 0.08 Torr at 22° C. is present in an amount ranging from 4.9 to 85 wt % of the fragrance component. Alternatively, first at least one perfume raw material having a first vapor pressure range of 0.0008 to 0.08 Torr at 22° C. is present in an amount ranging from 4.95 to 85 wt % of the fragrance component. Alternatively, first at least one perfume raw material having a first vapor pressure range of 0.0008 to 0.08 Torr at 22° C. is present in an amount ranging from 5 to 85 wt % of the fragrance component. Alternatively, first at least one perfume raw material having a first vapor pressure range of 0.0008 to 0.08 Torr at 22° C. is present in an amount ranging from 5.15 to 85 wt % of the fragrance component. Alternatively, first at least one perfume raw material having a first vapor pressure range of 0.0008 to 0.08 Torr at 22° C. is present in an amount ranging from 5.2 to 85 wt % of the fragrance component. Alternatively, first at least one perfume raw material having a first vapor pressure range of 0.0008 to 0.08 Torr at 22° C. is present in an amount ranging from 5.25 to 85 wt % of the fragrance component. Alternatively, first at least one perfume raw material having a first vapor pressure range of 0.0008 to 0.08 Torr at 22° C. is present in an amount ranging from 5.3 to 85 wt % of the fragrance component. Alternatively, first at least one perfume raw material having a first vapor pressure range of 0.0008 to 0.08 Torr at 22° C. is present in an amount ranging from 5.35 to 85 wt % of the fragrance component. Alternatively, first at least one perfume raw material having a first vapor pressure range of 0.0008 to 0.08 Torr at 22° C. is present in an amount ranging from 5.4 to 85 wt % of the fragrance component. Alternatively, first at least one perfume raw material having a first vapor pressure range of 0.0008 to 0.08 Torr at 22° C. is present in an amount ranging from 5.45 to 85 wt % of the fragrance component. Alternatively, first at least one perfume raw material having a first vapor pressure range of 0.0008 to 0.08 Torr at 22° C. is present in an amount ranging from 5.5 to 85 wt % of the fragrance component. Alternatively, first at least one perfume raw material having a first vapor pressure range of 0.0008 to 0.08 Torr at 22° C. is present in an amount ranging from 5.55 to 85 wt % of the fragrance component. Alternatively, first at least one perfume raw material having a first vapor pressure range of 0.0008 to 0.08 Torr at 22° C. is present in an amount ranging from 5.6 to 85 wt % of the fragrance component. Alternatively, first at least one perfume raw material having a first vapor pressure range of 0.0008 to 0.08 Torr at 22° C. is present in an amount ranging from 5.65 to 85 wt % of the fragrance component. Alternatively, first at least one perfume raw material having a first vapor pressure range of 0.0008 to 0.08 Torr at 22° C. is present in an amount ranging from 5.7 to 85 wt % of the fragrance component. Alternatively, first at least one perfume raw material having a first vapor pressure range of 0.0008 to 0.08 Torr at 22° C. is present in an amount ranging from 5.75 to 85 wt % of the fragrance component. Alternatively, first at least one perfume raw material having a first vapor pressure range of 0.0008 to 0.08 Torr at 22° C. is present in an amount ranging from 5.8 to 85 wt % of the fragrance component. Alternatively, first at least one perfume raw material having a first vapor pressure range of 0.0008 to 0.08 Torr at 22° C. is present in an amount ranging from 5.85 to 85 wt % of the fragrance component. Alternatively, first at least one perfume raw material having a first vapor pressure range of 0.0008 to 0.08 Torr at 22° C. is present in an amount ranging from 5.9 to 85 wt % of the fragrance component. Alternatively, first at least one perfume raw material having a first vapor pressure range of 0.0008 to 0.08 Torr at 22° C. is present in an amount ranging from 5.95 to 85 wt % of the fragrance component. Alternatively, first at least one perfume raw material having a first vapor pressure range of 0.0008 to 0.08 Torr at 22° C. is present in an amount ranging from 6 to 85 wt % of the fragrance component. Alternatively, first at least one perfume raw material having a first vapor pressure range of 0.0008 to 0.08 Torr at 22° C. is present in an amount ranging from 6.15 to 85 wt % of the fragrance component. Alternatively, first at least one perfume raw material having a first vapor pressure range of 0.0008 to 0.08 Torr at 22° C. is present in an amount ranging from 6.2 to 85 wt % of the fragrance component. Alternatively, first at least one perfume raw material having a first vapor pressure range of 0.0008 to 0.08 Torr at 22° C. is present in an amount ranging from 6.25 to 85 wt % of the fragrance component. Alternatively, first at least one perfume raw material having a first vapor pressure range of 0.0008 to 0.08 Torr at 22° C. is present in an amount ranging from 6.3 to 85 wt % of the fragrance component. Alternatively, first at least one perfume raw material having a first vapor pressure range of 0.0008 to 0.08 Torr at 22° C. is present in an amount ranging from 6.35 to 85 wt % of the fragrance component. Alternatively, first at least one perfume raw material having a first vapor pressure range of 0.0008 to 0.08 Torr at 22° C. is present in an amount ranging from 6.4 to 85 wt % of the fragrance component. Alternatively, first at least one perfume raw material having a first vapor pressure range of 0.0008 to 0.08 Torr at 22° C. is present in an amount ranging from 6.45 to 85 wt % of the fragrance component. Alternatively, first at least one perfume raw material having a first vapor pressure range of 0.0008 to 0.08 Torr at 22° C. is present in an amount ranging from 6.5 to 85 wt % of the fragrance component. Alternatively, first at least one perfume raw material having a first vapor pressure range of 0.0008 to 0.08 Torr at 22° C. is present in an amount ranging from 6.55 to 85 wt % of the fragrance component. Alternatively, first at least one perfume raw material having a first vapor pressure range of 0.0008 to 0.08 Torr at 22° C. is present in an amount ranging from 6.6 to 85 wt % of the fragrance component. Alternatively, first at least one perfume raw material having a first vapor pressure range of 0.0008 to 0.08 Torr at 22° C. is present in an amount ranging from 6.65 to 85 wt % of the fragrance component. Alternatively, first at least one perfume raw material having a first vapor pressure range of 0.0008 to 0.08 Torr at 22° C. is present in an amount ranging from 6.7 to 85 wt % of the fragrance component. Alternatively, first at least one perfume raw material having a first vapor pressure range of 0.0008 to 0.08 Torr at 22° C. is present in an amount ranging from 6.75 to 85 wt % of the fragrance component. Alternatively, first at least one perfume raw material having a first vapor pressure range of 0.0008 to 0.08 Torr at 22° C. is present in an amount ranging from 6.8 to 85 wt % of the fragrance component. Alternatively, first at least one perfume raw material having a first vapor pressure range of 0.0008 to 0.08 Torr at 22° C. is present in an amount ranging from 6.85 to 85 wt % of the fragrance component. Alternatively, first at least one perfume raw material having a first vapor pressure range of 0.0008 to 0.08 Torr at 22° C. is present in an amount ranging from 6.9 to 85 wt % of the fragrance component. Alternatively, first at least one perfume raw material having a first vapor pressure range of 0.0008 to 0.08 Torr at 22° C. is present in an amount ranging from 6.95 to 85 wt % of the fragrance component. Alternatively, first at least one perfume raw material having a first vapor pressure range of 0.0008 to 0.08 Torr at 22° C. is present in an amount ranging from 7 to 85 wt % of the fragrance component. Alternatively, first at least one perfume raw material having a first vapor pressure range of 0.0008 to 0.08 Torr at 22° C. is present in an amount ranging from 7.15 to 85 wt % of the fragrance component. Alternatively, first at least one perfume raw material having a first vapor pressure range of 0.0008 to 0.08 Torr at 22° C. is present in an amount ranging from 7.2 to 85 wt % of the fragrance component. Alternatively, first at least one perfume raw material having a first vapor pressure range of 0.0008 to 0.08 Torr at 22° C. is present in an amount ranging from 7.25 to 85 wt % of the fragrance component. Alternatively, first at least one perfume raw material having a first vapor pressure range of 0.0008 to 0.08 Torr at 22° C. is present in an amount ranging from 7.3 to 85 wt % of the fragrance component. Alternatively, first at least one perfume raw material having a first vapor pressure range of 0.0008 to 0.08 Torr at 22° C. is present in an amount ranging from 7.35 to 85 wt % of the fragrance component. Alternatively, first at least one perfume raw material having a first vapor pressure range of 0.0008 to 0.08 Torr at 22° C. is present in an amount ranging from 7.4 to 85 wt % of the fragrance component. Alternatively, first at least one perfume raw material having a first vapor pressure range of 0.0008 to 0.08 Torr at 22° C. is present in an amount ranging from 7.45 to 85 wt % of the fragrance component. Alternatively, first at least one perfume raw material having a first vapor pressure range of 0.0008 to 0.08 Torr at 22° C. is present in an amount ranging from 7.5 to 85 wt % of the fragrance component. Alternatively, first at least one perfume raw material having a first vapor pressure range of 0.0008 to 0.08 Torr at 22° C. is present in an amount ranging from 7.55 to 85 wt % of the fragrance component. Alternatively, first at least one perfume raw material having a first vapor pressure range of 0.0008 to 0.08 Torr at 22° C. is present in an amount ranging from 7.6 to 85 wt % of the fragrance component. Alternatively, first at least one perfume raw material having a first vapor pressure range of 0.0008 to 0.08 Torr at 22° C. is present in an amount ranging from 7.65 to 85 wt % of the fragrance component. Alternatively, first at least one perfume raw material having a first vapor pressure range of 0.0008 to 0.08 Torr at 22° C. is present in an amount ranging from 7.7 to 85 wt % of the fragrance component. Alternatively, first at least one perfume raw material having a first vapor pressure range of 0.0008 to 0.08 Torr at 22° C. is present in an amount ranging from 7.75 to 85 wt % of the fragrance component. Alternatively, first at least one perfume raw material having a first vapor pressure range of 0.0008 to 0.08 Torr at 22° C. is present in an amount ranging from 7.8 to 85 wt % of the fragrance component. Alternatively, first at least one perfume raw material having a first vapor pressure range of 0.0008 to 0.08 Torr at 22° C. is present in an amount ranging from 7.85 to 85 wt % of the fragrance component. Alternatively, first at least one perfume raw material having a first vapor pressure range of 0.0008 to 0.08 Torr at 22° C. is present in an amount ranging from 7.9 to 85 wt % of the fragrance component. Alternatively, first at least one perfume raw material having a first vapor pressure range of 0.0008 to 0.08 Torr at 22° C. is present in an amount ranging from 7.95 to 85 wt % of the fragrance component. Alternatively, first at least one perfume raw material having a first vapor pressure range of 0.0008 to 0.08 Torr at 22° C. is present in an amount ranging from 8 to 85 wt % of the fragrance component. Alternatively, first at least one perfume raw material having a first vapor pressure range of 0.0008 to 0.08 Torr at 22° C. is present in an amount ranging from 8.15 to 85 wt % of the fragrance component. Alternatively, first at least one perfume raw material having a first vapor pressure range of 0.0008 to 0.08 Torr at 22° C. is present in an amount ranging from 8.2 to 85 wt % of the fragrance component. Alternatively, first at least one perfume raw material having a first vapor pressure range of 0.0008 to 0.08 Torr at 22° C. is present in an amount ranging from 8.25 to 85 wt % of the fragrance component. Alternatively, first at least one perfume raw material having a first vapor pressure range of 0.0008 to 0.08 Torr at 22° C. is present in an amount ranging from 8.3 to 85 wt % of the fragrance component. Alternatively, first at least one perfume raw material having a first vapor pressure range of 0.0008 to 0.08 Torr at 22° C. is present in an amount ranging from 8.35 to 85 wt % of the fragrance component. Alternatively, first at least one perfume raw material having a first vapor pressure range of 0.0008 to 0.08 Torr at 22° C. is present in an amount ranging from 8.4 to 85 wt % of the fragrance component. Alternatively, first at least one perfume raw material having a first vapor pressure range of 0.0008 to 0.08 Torr at 22° C. is present in an amount ranging from 8.45 to 85 wt % of the fragrance component. Alternatively, first at least one perfume raw material having a first vapor pressure range of 0.0008 to 0.08 Torr at 22° C. is present in an amount ranging from 8.5 to 85 wt % of the fragrance component. Alternatively, first at least one perfume raw material having a first vapor pressure range of 0.0008 to 0.08 Torr at 22° C. is present in an amount ranging from 8.55 to 85 wt % of the fragrance component. Alternatively, first at least one perfume raw material having a first vapor pressure range of 0.0008 to 0.08 Torr at 22° C. is present in an amount ranging from 8.6 to 85 wt % of the fragrance component. Alternatively, first at least one perfume raw material having a first vapor pressure range of 0.0008 to 0.08 Torr at 22° C. is present in an amount ranging from 8.65 to 85 wt % of the fragrance component. Alternatively, first at least one perfume raw material having a first vapor pressure range of 0.0008 to 0.08 Torr at 22° C. is present in an amount ranging from 8.7 to 85 wt % of the fragrance component. Alternatively, first at least one perfume raw material having a first vapor pressure range of 0.0008 to 0.08 Torr at 22° C. is present in an amount ranging from 8.75 to 85 wt % of the fragrance component. Alternatively, first at least one perfume raw material having a first vapor pressure range of 0.0008 to 0.08 Torr at 22° C. is present in an amount ranging from 8.8 to 85 wt % of the fragrance component. Alternatively, first at least one perfume raw material having a first vapor pressure range of 0.0008 to 0.08 Torr at 22° C. is present in an amount ranging from 8.85 to 85 wt % of the fragrance component. Alternatively, first at least one perfume raw material having a first vapor pressure range of 0.0008 to 0.08 Torr at 22° C. is present in an amount ranging from 8.9 to 85 wt % of the fragrance component. Alternatively, first at least one perfume raw material having a first vapor pressure range of 0.0008 to 0.08 Torr at 22° C. is present in an amount ranging from 8.95 to 85 wt % of the fragrance component. Alternatively, first at least one perfume raw material having a first vapor pressure range of 0.0008 to 0.08 Torr at 22° C. is present in an amount ranging from 9 to 85 wt % of the fragrance component. Alternatively, first at least one perfume raw material having a first vapor pressure range of 0.0008 to 0.08 Torr at 22° C. is present in an amount ranging from 9.15 to 85 wt % of the fragrance component. Alternatively, first at least one perfume raw material having a first vapor pressure range of 0.0008 to 0.08 Torr at 22° C. is present in an amount ranging from 9.2 to 85 wt % of the fragrance component. Alternatively, first at least one perfume raw material having a first vapor pressure range of 0.0008 to 0.08 Torr at 22° C. is present in an amount ranging from 9.25 to 85 wt % of the fragrance component. Alternatively, first at least one perfume raw material having a first vapor pressure range of 0.0008 to 0.08 Torr at 22° C. is present in an amount ranging from 9.3 to 85 wt % of the fragrance component. Alternatively, first at least one perfume raw material having a first vapor pressure range of 0.0008 to 0.08 Torr at 22° C. is present in an amount ranging from 9.35 to 85 wt % of the fragrance component. Alternatively, first at least one perfume raw material having a first vapor pressure range of 0.0008 to 0.08 Torr at 22° C. is present in an amount ranging from 9.4 to 85 wt % of the fragrance component. Alternatively, first at least one perfume raw material having a first vapor pressure range of 0.0008 to 0.08 Torr at 22° C. is present in an amount ranging from 9.45 to 85 wt % of the fragrance component. Alternatively, first at least one perfume raw material having a first vapor pressure range of 0.0008 to 0.08 Torr at 22° C. is present in an amount ranging from 9.5 to 85 wt % of the fragrance component. Alternatively, first at least one perfume raw material having a first vapor pressure range of 0.0008 to 0.08 Torr at 22° C. is present in an amount ranging from 9.55 to 85 wt % of the fragrance component. Alternatively, first at least one perfume raw material having a first vapor pressure range of 0.0008 to 0.08 Torr at 22° C. is present in an amount ranging from 9.6 to 85 wt % of the fragrance component. Alternatively, first at least one perfume raw material having a first vapor pressure range of 0.0008 to 0.08 Torr at 22° C. is present in an amount ranging from 9.65 to 85 wt % of the fragrance component. Alternatively, first at least one perfume raw material having a first vapor pressure range of 0.0008 to 0.08 Torr at 22° C. is present in an amount ranging from 9.7 to 85 wt % of the fragrance component. Alternatively, first at least one perfume raw material having a first vapor pressure range of 0.0008 to 0.08 Torr at 22° C. is present in an amount ranging from 9.75 to 85 wt % of the fragrance component. Alternatively, first at least one perfume raw material having a first vapor pressure range of 0.0008 to 0.08 Torr at 22° C. is present in an amount ranging from 9.8 to 85 wt % of the fragrance component. Alternatively, first at least one perfume raw material having a first vapor pressure range of 0.0008 to 0.08 Torr at 22° C. is present in an amount ranging from 9.85 to 85 wt % of the fragrance component. Alternatively, first at least one perfume raw material having a first vapor pressure range of 0.0008 to 0.08 Torr at 22° C. is present in an amount ranging from 9.9 to 85 wt % of the fragrance component. Alternatively, first at least one perfume raw material having a first vapor pressure range of 0.0008 to 0.08 Torr at 22° C. is present in an amount ranging from 9.95 to 85 wt % of the fragrance component. Alternatively, first at least one perfume raw material having a first vapor pressure range of 0.0008 to 0.08 Torr at 22° C. is present in an amount ranging from 10 to 85 wt % of the fragrance component. Alternatively, first at least one perfume raw material having a first vapor pressure range of 0.0008 to 0.08 Torr at 22° C. is present in an amount ranging from 15 to 85 wt % of the fragrance component. Alternatively, first at least one perfume raw material having a first vapor pressure range of 0.0008 to 0.08 Torr at 22° C. is present in an amount ranging from 20 to 85 wt % of the fragrance component. Alternatively, first at least one perfume raw material having a first vapor pressure range of 0.0008 to 0.08 Torr at 22° C. is present in an amount ranging from 25 to 85 wt % of the fragrance component. Alternatively, first at least one perfume raw material having a first vapor pressure range of 0.0008 to 0.08 Torr at 22° C. is present in an amount ranging from 30 to 85 wt % of the fragrance component. Alternatively, first at least one perfume raw material having a first vapor pressure range of 0.0008 to 0.08 Torr at 22° C. is present in an amount ranging from 35 to 85 wt % of the fragrance component. Alternatively, first at least one perfume raw material having a first vapor pressure range of 0.0008 to 0.08 Torr at 22° C. is present in an amount ranging from 40 to 85 wt % of the fragrance component. Alternatively, first at least one perfume raw material having a first vapor pressure range of 0.0008 to 0.08 Torr at 22° C. is present in an amount ranging from 45 to 85 wt % of the fragrance component. Alternatively, first at least one perfume raw material having a first vapor pressure range of 0.0008 to 0.08 Torr at 22° C. is present in an amount ranging from 50 to 85 wt % of the fragrance component. Alternatively, first at least one perfume raw material having a first vapor pressure range of 0.0008 to 0.08 Torr at 22° C. is present in an amount ranging from 55 to 85 wt % of the fragrance component. Alternatively, first at least one perfume raw material having a first vapor pressure range of 0.0008 to 0.08 Torr at 22° C. is present in an amount ranging from 60 to 85 wt % of the fragrance component. Alternatively, first at least one perfume raw material having a first vapor pressure range of 0.0008 to 0.08 Torr at 22° C. is present in an amount ranging from 65 to 85 wt % of the fragrance component. Alternatively, first at least one perfume raw material having a first vapor pressure range of 0.0008 to 0.08 Torr at 22° C. is present in an amount ranging from 70 to 85 wt % of the fragrance component. Alternatively, first at least one perfume raw material having a first vapor pressure range of 0.0008 to 0.08 Torr at 22° C. is present in an amount ranging from 75 to 85 wt % of the fragrance component. Alternatively, first at least one perfume raw material having a first vapor pressure range of 0.0008 to 0.08 Torr at 22° C. is present in an amount ranging from 80 to 85 wt % of the fragrance component.

Alternatively, first at least one perfume raw material having a first vapor pressure range of 0.0008 to 0.08 Torr at 22° C. is present in an amount ranging from 0.08 to 85 wt % of the fragrance component. Alternatively, first at least one perfume raw material having a first vapor pressure range of 0.0008 to 0.08 Torr at 22° C. is present in an amount ranging from 0.08 to 80 wt % of the fragrance component. Alternatively, first at least one perfume raw material having a first vapor pressure range of 0.0008 to 0.08 Torr at 22° C. is present in an amount ranging from 0.08 to 75 wt % of the fragrance component. Alternatively, first at least one perfume raw material having a first vapor pressure range of 0.0008 to 0.08 Torr at 22° C. is present in an amount ranging from 0.08 to 70 wt % of the fragrance component. Alternatively, first at least one perfume raw material having a first vapor pressure range of 0.0008 to 0.08 Torr at 22° C. is present in an amount ranging from 0.08 to 65 wt % of the fragrance component. Alternatively, first at least one perfume raw material having a first vapor pressure range of 0.0008 to 0.08 Torr at 22° C. is present in an amount ranging from 0.08 to 60 wt % of the fragrance component. Alternatively, first at least one perfume raw material having a first vapor pressure range of 0.0008 to 0.08 Torr at 22° C. is present in an amount ranging from 0.08 to 55 wt % of the fragrance component. Alternatively, first at least one perfume raw material having a first vapor pressure range of 0.0008 to 0.08 Torr at 22° C. is present in an amount ranging from 0.08 to 50 wt % of the fragrance component. Alternatively, first at least one perfume raw material having a first vapor pressure range of 0.0008 to 0.08 Torr at 22° C. is present in an amount ranging from 0.08 to 45 wt % of the fragrance component. Alternatively, first at least one perfume raw material having a first vapor pressure range of 0.0008 to 0.08 Torr at 22° C. is present in an amount ranging from 0.08 to 40 wt % of the fragrance component. Alternatively, first at least one perfume raw material having a first vapor pressure range of 0.0008 to 0.08 Torr at 22° C. is present in an amount ranging from 0.08 to 35 wt % of the fragrance component. Alternatively, first at least one perfume raw material having a first vapor pressure range of 0.0008 to 0.08 Torr at 22° C. is present in an amount ranging from 0.08 to 30 wt % of the fragrance component. Alternatively, first at least one perfume raw material having a first vapor pressure range of 0.0008 to 0.08 Torr at 22° C. is present in an amount ranging from 0.08 to 25 wt % of the fragrance component. Alternatively, first at least one perfume raw material having a first vapor pressure range of 0.0008 to 0.08 Torr at 22° C. is present in an amount ranging from 0.08 to 20 wt % of the fragrance component. Alternatively, first at least one perfume raw material having a first vapor pressure range of 0.0008 to 0.08 Torr at 22° C. is present in an amount ranging from 0.08 to 15 wt % of the fragrance component. Alternatively, first at least one perfume raw material having a first vapor pressure range of 0.0008 to 0.08 Torr at 22° C. is present in an amount ranging from 0.08 to 10 wt % of the fragrance component. Alternatively, first at least one perfume raw material having a first vapor pressure range of 0.0008 to 0.08 Torr at 22° C. is present in an amount ranging from 0.08 to 9.9 wt % of the fragrance component. Alternatively, first at least one perfume raw material having a first vapor pressure range of 0.0008 to 0.08 Torr at 22° C. is present in an amount ranging from 0.08 to 9.8 wt % of the fragrance component. Alternatively, first at least one perfume raw material having a first vapor pressure range of 0.0008 to 0.08 Torr at 22° C. is present in an amount ranging from 0.08 to 9.7 wt % of the fragrance component. Alternatively, first at least one perfume raw material having a first vapor pressure range of 0.0008 to 0.08 Torr at 22° C. is present in an amount ranging from 0.08 to 9.6 wt % of the fragrance component. Alternatively, first at least one perfume raw material having a first vapor pressure range of 0.0008 to 0.08 Torr at 22° C. is present in an amount ranging from 0.08 to 9.5 wt % of the fragrance component. Alternatively, first at least one perfume raw material having a first vapor pressure range of 0.0008 to 0.08 Torr at 22° C. is present in an amount ranging from 0.08 to 9.4 wt % of the fragrance component. Alternatively, first at least one perfume raw material having a first vapor pressure range of 0.0008 to 0.08 Torr at 22° C. is present in an amount ranging from 0.08 to 9.3 wt % of the fragrance component. Alternatively, first at least one perfume raw material having a first vapor pressure range of 0.0008 to 0.08 Torr at 22° C. is present in an amount ranging from 0.08 to 9.2 wt % of the fragrance component. Alternatively, first at least one perfume raw material having a first vapor pressure range of 0.0008 to 0.08 Torr at 22° C. is present in an amount ranging from 0.08 to 9.1 wt % of the fragrance component. Alternatively, first at least one perfume raw material having a first vapor pressure range of 0.0008 to 0.08 Torr at 22° C. is present in an amount ranging from 0.08 to 9 wt % of the fragrance component. Alternatively, first at least one perfume raw material having a first vapor pressure range of 0.0008 to 0.08 Torr at 22° C. is present in an amount ranging from 0.08 to 8.9 wt % of the fragrance component. Alternatively, first at least one perfume raw material having a first vapor pressure range of 0.0008 to 0.08 Torr at 22° C. is present in an amount ranging from 0.08 to 8.8 wt % of the fragrance component. Alternatively, first at least one perfume raw material having a first vapor pressure range of 0.0008 to 0.08 Torr at 22° C. is present in an amount ranging from 0.08 to 8.7 wt % of the fragrance component. Alternatively, first at least one perfume raw material having a first vapor pressure range of 0.0008 to 0.08 Torr at 22° C. is present in an amount ranging from 0.08 to 8.6 wt % of the fragrance component. Alternatively, first at least one perfume raw material having a first vapor pressure range of 0.0008 to 0.08 Torr at 22° C. is present in an amount ranging from 0.08 to 8.5 wt % of the fragrance component. Alternatively, first at least one perfume raw material having a first vapor pressure range of 0.0008 to 0.08 Torr at 22° C. is present in an amount ranging from 0.08 to 8.4 wt % of the fragrance component. Alternatively, first at least one perfume raw material having a first vapor pressure range of 0.0008 to 0.08 Torr at 22° C. is present in an amount ranging from 0.08 to 8.3 wt % of the fragrance component. Alternatively, first at least one perfume raw material having a first vapor pressure range of 0.0008 to 0.08 Torr at 22° C. is present in an amount ranging from 0.08 to 8.2 wt % of the fragrance component. Alternatively, first at least one perfume raw material having a first vapor pressure range of 0.0008 to 0.08 Torr at 22° C. is present in an amount ranging from 0.08 to 8.1 wt % of the fragrance component. Alternatively, first at least one perfume raw material having a first vapor pressure range of 0.0008 to 0.08 Torr at 22° C. is present in an amount ranging from 0.08 to 8 wt % of the fragrance component. Alternatively, first at least one perfume raw material having a first vapor pressure range of 0.0008 to 0.08 Torr at 22° C. is present in an amount ranging from 0.08 to 7.9 wt % of the fragrance component. Alternatively, first at least one perfume raw material having a first vapor pressure range of 0.0008 to 0.08 Torr at 22° C. is present in an amount ranging from 0.08 to 7.8 wt % of the fragrance component. Alternatively, first at least one perfume raw material having a first vapor pressure range of 0.0008 to 0.08 Torr at 22° C. is present in an amount ranging from 0.08 to 7.7 wt % of the fragrance component. Alternatively, first at least one perfume raw material having a first vapor pressure range of 0.0008 to 0.08 Torr at 22° C. is present in an amount ranging from 0.08 to 7.6 wt % of the fragrance component. Alternatively, first at least one perfume raw material having a first vapor pressure range of 0.0008 to 0.08 Torr at 22° C. is present in an amount ranging from 0.08 to 7.5 wt % of the fragrance component. Alternatively, first at least one perfume raw material having a first vapor pressure range of 0.0008 to 0.08 Torr at 22° C. is present in an amount ranging from 0.08 to 7.4 wt % of the fragrance component. Alternatively, first at least one perfume raw material having a first vapor pressure range of 0.0008 to 0.08 Torr at 22° C. is present in an amount ranging from 0.08 to 7.3 wt % of the fragrance component. Alternatively, first at least one perfume raw material having a first vapor pressure range of 0.0008 to 0.08 Torr at 22° C. is present in an amount ranging from 0.08 to 7.2 wt % of the fragrance component. Alternatively, first at least one perfume raw material having a first vapor pressure range of 0.0008 to 0.08 Torr at 22° C. is present in an amount ranging from 0.08 to 7.1 wt % of the fragrance component. Alternatively, first at least one perfume raw material having a first vapor pressure range of 0.0008 to 0.08 Torr at 22° C. is present in an amount ranging from 0.08 to 7 wt % of the fragrance component. Alternatively, first at least one perfume raw material having a first vapor pressure range of 0.0008 to 0.08 Torr at 22° C. is present in an amount ranging from 0.08 to 6.9 wt % of the fragrance component. Alternatively, first at least one perfume raw material having a first vapor pressure range of 0.0008 to 0.08 Torr at 22° C. is present in an amount ranging from 0.08 to 6.8 wt % of the fragrance component. Alternatively, first at least one perfume raw material having a first vapor pressure range of 0.0008 to 0.08 Torr at 22° C. is present in an amount ranging from 0.08 to 6.7 wt % of the fragrance component. Alternatively, first at least one perfume raw material having a first vapor pressure range of 0.0008 to 0.08 Torr at 22° C. is present in an amount ranging from 0.08 to 6.6 wt % of the fragrance component. Alternatively, first at least one perfume raw material having a first vapor pressure range of 0.0008 to 0.08 Torr at 22° C. is present in an amount ranging from 0.08 to 6.5 wt % of the fragrance component. Alternatively, first at least one perfume raw material having a first vapor pressure range of 0.0008 to 0.08 Torr at 22° C. is present in an amount ranging from 0.08 to 6.4 wt % of the fragrance component. Alternatively, first at least one perfume raw material having a first vapor pressure range of 0.0008 to 0.08 Torr at 22° C. is present in an amount ranging from 0.08 to 6.3 wt % of the fragrance component. Alternatively, first at least one perfume raw material having a first vapor pressure range of 0.0008 to 0.08 Torr at 22° C. is present in an amount ranging from 0.08 to 6.2 wt % of the fragrance component. Alternatively, first at least one perfume raw material having a first vapor pressure range of 0.0008 to 0.08 Torr at 22° C. is present in an amount ranging from 0.08 to 6.1 wt % of the fragrance component. Alternatively, first at least one perfume raw material having a first vapor pressure range of 0.0008 to 0.08 Torr at 22° C. is present in an amount ranging from 0.08 to 6 wt % of the fragrance component. Alternatively, first at least one perfume raw material having a first vapor pressure range of 0.0008 to 0.08 Torr at 22° C. is present in an amount ranging from 0.08 to 5.9 wt % of the fragrance component. Alternatively, first at least one perfume raw material having a first vapor pressure range of 0.0008 to 0.08 Torr at 22° C. is present in an amount ranging from 0.08 to 5.8 wt % of the fragrance component. Alternatively, first at least one perfume raw material having a first vapor pressure range of 0.0008 to 0.08 Torr at 22° C. is present in an amount ranging from 0.08 to 5.7 wt % of the fragrance component. Alternatively, first at least one perfume raw material having a first vapor pressure range of 0.0008 to 0.08 Torr at 22° C. is present in an amount ranging from 0.08 to 5.6 wt % of the fragrance component. Alternatively, first at least one perfume raw material having a first vapor pressure range of 0.0008 to 0.08 Torr at 22° C. is present in an amount ranging from 0.08 to 5.5 wt % of the fragrance component. Alternatively, first at least one perfume raw material having a first vapor pressure range of 0.0008 to 0.08 Torr at 22° C. is present in an amount ranging from 0.08 to 5.4 wt % of the fragrance component. Alternatively, first at least one perfume raw material having a first vapor pressure range of 0.0008 to 0.08 Torr at 22° C. is present in an amount ranging from 0.08 to 5.3 wt % of the fragrance component. Alternatively, first at least one perfume raw material having a first vapor pressure range of 0.0008 to 0.08 Torr at 22° C. is present in an amount ranging from 0.08 to 5.2 wt % of the fragrance component. Alternatively, first at least one perfume raw material having a first vapor pressure range of 0.0008 to 0.08 Torr at 22° C. is present in an amount ranging from 0.08 to 5.1 wt % of the fragrance component. Alternatively, first at least one perfume raw material having a first vapor pressure range of 0.0008 to 0.08 Torr at 22° C. is present in an amount ranging from 0.08 to 5 wt % of the fragrance component. Alternatively, first at least one perfume raw material having a first vapor pressure range of 0.0008 to 0.08 Torr at 22° C. is present in an amount ranging from 0.08 to 4.9 wt % of the fragrance component. Alternatively, first at least one perfume raw material having a first vapor pressure range of 0.0008 to 0.08 Torr at 22° C. is present in an amount ranging from 0.08 to 4.8 wt % of the fragrance component. Alternatively, first at least one perfume raw material having a first vapor pressure range of 0.0008 to 0.08 Torr at 22° C. is present in an amount ranging from 0.08 to 4.7 wt % of the fragrance component. Alternatively, first at least one perfume raw material having a first vapor pressure range of 0.0008 to 0.08 Torr at 22° C. is present in an amount ranging from 0.08 to 4.6 wt % of the fragrance component. Alternatively, first at least one perfume raw material having a first vapor pressure range of 0.0008 to 0.08 Torr at 22° C. is present in an amount ranging from 0.08 to 4.5 wt % of the fragrance component. Alternatively, first at least one perfume raw material having a first vapor pressure range of 0.0008 to 0.08 Torr at 22° C. is present in an amount ranging from 0.08 to 4.4 wt % of the fragrance component. Alternatively, first at least one perfume raw material having a first vapor pressure range of 0.0008 to 0.08 Torr at 22° C. is present in an amount ranging from 0.08 to 4.3 wt % of the fragrance component. Alternatively, first at least one perfume raw material having a first vapor pressure range of 0.0008 to 0.08 Torr at 22° C. is present in an amount ranging from 0.08 to 4.2 wt % of the fragrance component. Alternatively, first at least one perfume raw material having a first vapor pressure range of 0.0008 to 0.08 Torr at 22° C. is present in an amount ranging from 0.08 to 4.1 wt % of the fragrance component. Alternatively, first at least one perfume raw material having a first vapor pressure range of 0.0008 to 0.08 Torr at 22° C. is present in an amount ranging from 0.08 to 4 wt % of the fragrance component. Alternatively, first at least one perfume raw material having a first vapor pressure range of 0.0008 to 0.08 Torr at 22° C. is present in an amount ranging from 0.08 to 3.9 wt % of the fragrance component. Alternatively, first at least one perfume raw material having a first vapor pressure range of 0.0008 to 0.08 Torr at 22° C. is present in an amount ranging from 0.08 to 3.8 wt % of the fragrance component. Alternatively, first at least one perfume raw material having a first vapor pressure range of 0.0008 to 0.08 Torr at 22° C. is present in an amount ranging from 0.08 to 3.7 wt % of the fragrance component. Alternatively, first at least one perfume raw material having a first vapor pressure range of 0.0008 to 0.08 Torr at 22° C. is present in an amount ranging from 0.08 to 3.6 wt % of the fragrance component. Alternatively, first at least one perfume raw material having a first vapor pressure range of 0.0008 to 0.08 Torr at 22° C. is present in an amount ranging from 0.08 to 3.5 wt % of the fragrance component. Alternatively, first at least one perfume raw material having a first vapor pressure range of 0.0008 to 0.08 Torr at 22° C. is present in an amount ranging from 0.08 to 3.4 wt % of the fragrance component. Alternatively, first at least one perfume raw material having a first vapor pressure range of 0.0008 to 0.08 Torr at 22° C. is present in an amount ranging from 0.08 to 3.3 wt % of the fragrance component. Alternatively, first at least one perfume raw material having a first vapor pressure range of 0.0008 to 0.08 Torr at 22° C. is present in an amount ranging from 0.08 to 3.2 wt % of the fragrance component. Alternatively, first at least one perfume raw material having a first vapor pressure range of 0.0008 to 0.08 Torr at 22° C. is present in an amount ranging from 0.08 to 3.1 wt % of the fragrance component. Alternatively, first at least one perfume raw material having a first vapor pressure range of 0.0008 to 0.08 Torr at 22° C. is present in an amount ranging from 0.08 to 3 wt % of the fragrance component. Alternatively, first at least one perfume raw material having a first vapor pressure range of 0.0008 to 0.08 Torr at 22° C. is present in an amount ranging from 0.08 to 2.9 wt % of the fragrance component. Alternatively, first at least one perfume raw material having a first vapor pressure range of 0.0008 to 0.08 Torr at 22° C. is present in an amount ranging from 0.08 to 2.8 wt % of the fragrance component. Alternatively, first at least one perfume raw material having a first vapor pressure range of 0.0008 to 0.08 Torr at 22° C. is present in an amount ranging from 0.08 to 2.7 wt % of the fragrance component. Alternatively, first at least one perfume raw material having a first vapor pressure range of 0.0008 to 0.08 Torr at 22° C. is present in an amount ranging from 0.08 to 2.6 wt % of the fragrance component. Alternatively, first at least one perfume raw material having a first vapor pressure range of 0.0008 to 0.08 Torr at 22° C. is present in an amount ranging from 0.08 to 2.5 wt % of the fragrance component. Alternatively, first at least one perfume raw material having a first vapor pressure range of 0.0008 to 0.08 Torr at 22° C. is present in an amount ranging from 0.08 to 2.4 wt % of the fragrance component. Alternatively, first at least one perfume raw material having a first vapor pressure range of 0.0008 to 0.08 Torr at 22° C. is present in an amount ranging from 0.08 to 2.3 wt % of the fragrance component. Alternatively, first at least one perfume raw material having a first vapor pressure range of 0.0008 to 0.08 Torr at 22° C. is present in an amount ranging from 0.08 to 2.2 wt % of the fragrance component. Alternatively, first at least one perfume raw material having a first vapor pressure range of 0.0008 to 0.08 Torr at 22° C. is present in an amount ranging from 0.08 to 2.1 wt % of the fragrance component. Alternatively, first at least one perfume raw material having a first vapor pressure range of 0.0008 to 0.08 Torr at 22° C. is present in an amount ranging from 0.08 to 2 wt % of the fragrance component. Alternatively, first at least one perfume raw material having a first vapor pressure range of 0.0008 to 0.08 Torr at 22° C. is present in an amount ranging from 0.08 to 1.9 wt % of the fragrance component. Alternatively, first at least one perfume raw material having a first vapor pressure range of 0.0008 to 0.08 Torr at 22° C. is present in an amount ranging from 0.08 to 1.8 wt % of the fragrance component. Alternatively, first at least one perfume raw material having a first vapor pressure range of 0.0008 to 0.08 Torr at 22° C. is present in an amount ranging from 0.08 to 1.7 wt % of the fragrance component. Alternatively, first at least one perfume raw material having a first vapor pressure range of 0.0008 to 0.08 Torr at 22° C. is present in an amount ranging from 0.08 to 1.6 wt % of the fragrance component. Alternatively, first at least one perfume raw material having a first vapor pressure range of 0.0008 to 0.08 Torr at 22° C. is present in an amount ranging from 0.08 to 1.5 wt % of the fragrance component. Alternatively, first at least one perfume raw material having a first vapor pressure range of 0.0008 to 0.08 Torr at 22° C. is present in an amount ranging from 0.08 to 1.4 wt % of the fragrance component. Alternatively, first at least one perfume raw material having a first vapor pressure range of 0.0008 to 0.08 Torr at 22° C. is present in an amount ranging from 0.08 to 1.3 wt % of the fragrance component. Alternatively, first at least one perfume raw material having a first vapor pressure range of 0.0008 to 0.08 Torr at 22° C. is present in an amount ranging from 0.08 to 1.2 wt % of the fragrance component. Alternatively, first at least one perfume raw material having a first vapor pressure range of 0.0008 to 0.08 Torr at 22° C. is present in an amount ranging from 0.08 to 1.1 wt % of the fragrance component. Alternatively, first at least one perfume raw material having a first vapor pressure range of 0.0008 to 0.08 Torr at 22° C. is present in an amount ranging from 0.08 to 1 wt % of the fragrance component. Alternatively, first at least one perfume raw material having a first vapor pressure range of 0.0008 to 0.08 Torr at 22° C. is present in an amount ranging from 0.08 to 0.9 wt % of the fragrance component. Alternatively, first at least one perfume raw material having a first vapor pressure range of 0.0008 to 0.08 Torr at 22° C. is present in an amount ranging from 0.08 to 0.8 wt % of the fragrance component. Alternatively, first at least one perfume raw material having a first vapor pressure range of 0.0008 to 0.08 Torr at 22° C. is present in an amount ranging from 0.08 to 0.7 wt % of the fragrance component. Alternatively, first at least one perfume raw material having a first vapor pressure range of 0.0008 to 0.08 Torr at 22° C. is present in an amount ranging from 0.08 to 0.6 wt % of the fragrance component. Alternatively, first at least one perfume raw material having a first vapor pressure range of 0.0008 to 0.08 Torr at 22° C. is present in an amount ranging from 0.08 to 0.5 wt % of the fragrance component. Alternatively, first at least one perfume raw material having a first vapor pressure range of 0.0008 to 0.08 Torr at 22° C. is present in an amount ranging from 0.08 to 0.4 wt % of the fragrance component. Alternatively, first at least one perfume raw material having a first vapor pressure range of 0.0008 to 0.08 Torr at 22° C. is present in an amount ranging from 0.08 to 0.3 wt % of the fragrance component. Alternatively, first at least one perfume raw material having a first vapor pressure range of 0.0008 to 0.08 Torr at 22° C. is present in an amount ranging from 0.08 to 0.2 wt % of the fragrance component. Alternatively, first at least one perfume raw material having a first vapor pressure range of 0.0008 to 0.08 Torr at 22° C. is present in an amount ranging from 0.08 to 0.1 wt % of the fragrance component. Alternatively, first at least one perfume raw material having a first vapor pressure range of 0.0008 to 0.08 Torr at 22° C. is present in an amount ranging from 0.08 to 0.09 wt % of the fragrance component.

In some aspects, first at least one perfume raw material having a first vapor pressure range of 0.0008 to 0.08 Torr at 22° C. is present at 0.008, 0.009, 0.01, 0.015, 0.02, 0.025, 0.03, 0.035, 0.04, 0.045, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 4.15, 4.2, 4.25, 4.3, 4.35, 4.4, 4.45, 4.5, 4.55, 4.6, 4.65, 4.7, 4.75, 4.8, 4.85, 4.9, 4.95, 5, 5.15, 5.2, 5.25, 5.3, 5.35, 5.4, 5.45, 5.5, 5.55, 5.6, 5.65, 5.7, 5.75, 5.8, 5.85, 5.9, 5.95, 6, 6.15, 6.2, 6.25, 6.3, 6.35, 6.4, 6.45, 6.5, 6.55, 6.6, 6.65, 6.7, 6.75, 6.8, 6.85, 6.9, 6.95, 7, 7.15, 7.2, 7.25, 7.3, 7.35, 7.4, 7.45, 7.5, 7.55, 7.6, 7.65, 7.7, 7.75, 7.8, 7.85, 7.9, 7.95, 8, 8.15, 8.2, 8.25, 8.3, 8.35, 8.4, 8.45, 8.5, 8.55, 8.6, 8.65, 8.7, 8.75, 8.8, 8.85, 8.9, 8.95, 9, 9.15, 9.2, 9.25, 9.3, 9.35, 9.4, 9.45, 9.5, 9.55, 9.6, 9.65, 9.7, 9.75, 9.8, 9.85, 9.9, 9.95, 10, 15, 20, 25, 30, 35, 40, 45, 50, 55, 60, 65, 70, 75, 80, or 85 wt % of the fragrance component.

In one aspect, the high volatility component comprises the second at least one perfume raw material having a first vapor pressure greater than 0.08 Torr at 22° C. in an amount from 0.1 to 40 wt % of the fragrance component. Alternatively, the second at least one perfume raw material having a first vapor pressure greater than 0.08 Torr at 22° C. is present in an amount ranging from 0.15 to 40 wt % of the fragrance component. Alternatively, the second at least one perfume raw material having a first vapor pressure greater than 0.08 Torr at 22° C. is present in an amount ranging from 0.2 to 40 wt % of the fragrance component. Alternatively, the second at least one perfume raw material having a first vapor pressure greater than 0.08 Torr at 22° C. is present in an amount ranging from 0.25 to 40 wt % of the fragrance component. Alternatively, the second at least one perfume raw material having a first vapor pressure greater than 0.08 Torr at 22° C. is present in an amount ranging from 0.3 to 40 wt % of the fragrance component. Alternatively, the second at least one perfume raw material having a first vapor pressure greater than 0.08 Torr at 22° C. is present in an amount ranging from 0.35 to 40 wt % of the fragrance component. Alternatively, the second at least one perfume raw material having a first vapor pressure greater than 0.08 Torr at 22° C. is present in an amount ranging from 0.4 to 40 wt % of the fragrance component. Alternatively, the second at least one perfume raw material having a first vapor pressure greater than 0.08 Torr at 22° C. is present in an amount ranging from 0.45 to 40 wt % of the fragrance component. Alternatively, the second at least one perfume raw material having a first vapor pressure greater than 0.08 Torr at 22° C. is present in an amount ranging from 0.5 to 40 wt % of the fragrance component. Alternatively, the second at least one perfume raw material having a first vapor pressure greater than 0.08 Torr at 22° C. is present in an amount ranging from 0.55 to 40 wt % of the fragrance component. Alternatively, the second at least one perfume raw material having a first vapor pressure greater than 0.08 Torr at 22° C. is present in an amount ranging from 0.6 to 40 wt % of the fragrance component. Alternatively, the second at least one perfume raw material having a first vapor pressure greater than 0.08 Torr at 22° C. is present in an amount ranging from 0.65 to 40 wt % of the fragrance component. Alternatively, the second at least one perfume raw material having a first vapor pressure greater than 0.08 Torr at 22° C. is present in an amount ranging from 0.7 to 40 wt % of the fragrance component. Alternatively, the second at least one perfume raw material having a first vapor pressure greater than 0.08 Torr at 22° C. is present in an amount ranging from 0.75 to 40 wt % of the fragrance component. Alternatively, the second at least one perfume raw material having a first vapor pressure greater than 0.08 Torr at 22° C. is present in an amount ranging from 0.8 to 40 wt % of the fragrance component. Alternatively, the second at least one perfume raw material having a first vapor pressure greater than 0.08 Torr at 22° C. is present in an amount ranging from 0.85 to 40 wt % of the fragrance component. Alternatively, the second at least one perfume raw material having a first vapor pressure greater than 0.08 Torr at 22° C. is present in an amount ranging from 0.9 to 40 wt % of the fragrance component. Alternatively, the second at least one perfume raw material having a first vapor pressure greater than 0.08 Torr at 22° C. is present in an amount ranging from 0.95 to 40 wt % of the fragrance component. Alternatively, the second at least one perfume raw material having a first vapor pressure greater than 0.08 Torr at 22° C. is present in an amount ranging from 1 to 40 wt % of the fragrance component. Alternatively, the second at least one perfume raw material having a first vapor pressure greater than 0.08 Torr at 22° C. is present in an amount ranging from 1.15 to 40 wt % of the fragrance component. Alternatively, the second at least one perfume raw material having a first vapor pressure greater than 0.08 Torr at 22° C. is present in an amount ranging from 1.2 to 40 wt % of the fragrance component. Alternatively, the second at least one perfume raw material having a first vapor pressure greater than 0.08 Torr at 22° C. is present in an amount ranging from 1.25 to 40 wt % of the fragrance component. Alternatively, the second at least one perfume raw material having a first vapor pressure greater than 0.08 Torr at 22° C. is present in an amount ranging from 1.3 to 40 wt % of the fragrance component. Alternatively, the second at least one perfume raw material having a first vapor pressure greater than 0.08 Torr at 22° C. is present in an amount ranging from 1.35 to 40 wt % of the fragrance component. Alternatively, the second at least one perfume raw material having a first vapor pressure greater than 0.08 Torr at 22° C. is present in an amount ranging from 1.4 to 40 wt % of the fragrance component. Alternatively, the second at least one perfume raw material having a first vapor pressure greater than 0.08 Torr at 22° C. is present in an amount ranging from 1.45 to 40 wt % of the fragrance component. Alternatively, the second at least one perfume raw material having a first vapor pressure greater than 0.08 Torr at 22° C. is present in an amount ranging from 1.5 to 40 wt % of the fragrance component. Alternatively, the second at least one perfume raw material having a first vapor pressure greater than 0.08 Torr at 22° C. is present in an amount ranging from 1.55 to 40 wt % of the fragrance component. Alternatively, the second at least one perfume raw material having a first vapor pressure greater than 0.08 Torr at 22° C. is present in an amount ranging from 1.6 to 40 wt % of the fragrance component. Alternatively, the second at least one perfume raw material having a first vapor pressure greater than 0.08 Torr at 22° C. is present in an amount ranging from 1.65 to 40 wt % of the fragrance component. Alternatively, the second at least one perfume raw material having a first vapor pressure greater than 0.08 Torr at 22° C. is present in an amount ranging from 1.7 to 40 wt % of the fragrance component. Alternatively, the second at least one perfume raw material having a first vapor pressure greater than 0.08 Torr at 22° C. is present in an amount ranging from 1.75 to 40 wt % of the fragrance component. Alternatively, the second at least one perfume raw material having a first vapor pressure greater than 0.08 Torr at 22° C. is present in an amount ranging from 1.8 to 40 wt % of the fragrance component. Alternatively, the second at least one perfume raw material having a first vapor pressure greater than 0.08 Torr at 22° C. is present in an amount ranging from 1.85 to 40 wt % of the fragrance component. Alternatively, the second at least one perfume raw material having a first vapor pressure greater than 0.08 Torr at 22° C. is present in an amount ranging from 1.9 to 40 wt % of the fragrance component. Alternatively, the second at least one perfume raw material having a first vapor pressure greater than 0.08 Torr at 22° C. is present in an amount ranging from 1.95 to 40 wt % of the fragrance component. Alternatively, the second at least one perfume raw material having a first vapor pressure greater than 0.08 Torr at 22° C. is present in an amount ranging from 2 to 40 wt % of the fragrance component. Alternatively, the second at least one perfume raw material having a first vapor pressure greater than 0.08 Torr at 22° C. is present in an amount ranging from 2.15 to 40 wt % of the fragrance component. Alternatively, the second at least one perfume raw material having a first vapor pressure greater than 0.08 Torr at 22° C. is present in an amount ranging from 2.2 to 40 wt % of the fragrance component. Alternatively, the second at least one perfume raw material having a first vapor pressure greater than 0.08 Torr at 22° C. is present in an amount ranging from 2.25 to 40 wt % of the fragrance component. Alternatively, the second at least one perfume raw material having a first vapor pressure greater than 0.08 Torr at 22° C. is present in an amount ranging from 2.3 to 40 wt % of the fragrance component. Alternatively, the second at least one perfume raw material having a first vapor pressure greater than 0.08 Torr at 22° C. is present in an amount ranging from 2.35 to 40 wt % of the fragrance component. Alternatively, the second at least one perfume raw material having a first vapor pressure greater than 0.08 Torr at 22° C. is present in an amount ranging from 2.4 to 40 wt % of the fragrance component. Alternatively, the second at least one perfume raw material having a first vapor pressure greater than 0.08 Torr at 22° C. is present in an amount ranging from 2.45 to 40 wt % of the fragrance component. Alternatively, the second at least one perfume raw material having a first vapor pressure greater than 0.08 Torr at 22° C. is present in an amount ranging from 2.5 to 40 wt % of the fragrance component. Alternatively, the second at least one perfume raw material having a first vapor pressure greater than 0.08 Torr at 22° C. is present in an amount ranging from 2.55 to 40 wt % of the fragrance component. Alternatively, the second at least one perfume raw material having a first vapor pressure greater than 0.08 Torr at 22° C. is present in an amount ranging from 2.6 to 40 wt % of the fragrance component. Alternatively, the second at least one perfume raw material having a first vapor pressure greater than 0.08 Torr at 22° C. is present in an amount ranging from 2.65 to 40 wt % of the fragrance component. Alternatively, the second at least one perfume raw material having a first vapor pressure greater than 0.08 Torr at 22° C. is present in an amount ranging from 2.7 to 40 wt % of the fragrance component. Alternatively, the second at least one perfume raw material having a first vapor pressure greater than 0.08 Torr at 22° C. is present in an amount ranging from 2.75 to 40 wt % of the fragrance component. Alternatively, the second at least one perfume raw material having a first vapor pressure greater than 0.08 Torr at 22° C. is present in an amount ranging from 2.8 to 40 wt % of the fragrance component. Alternatively, the second at least one perfume raw material having a first vapor pressure greater than 0.08 Torr at 22° C. is present in an amount ranging from 2.85 to 40 wt % of the fragrance component. Alternatively, the second at least one perfume raw material having a first vapor pressure greater than 0.08 Torr at 22° C. is present in an amount ranging from 2.9 to 40 wt % of the fragrance component. Alternatively, the second at least one perfume raw material having a first vapor pressure greater than 0.08 Torr at 22° C. is present in an amount ranging from 2.95 to 40 wt % of the fragrance component. Alternatively, the second at least one perfume raw material having a first vapor pressure greater than 0.08 Torr at 22° C. is present in an amount ranging from 3 to 40 wt % of the fragrance component. Alternatively, the second at least one perfume raw material having a first vapor pressure greater than 0.08 Torr at 22° C. is present in an amount ranging from 3.15 to 40 wt % of the fragrance component. Alternatively, the second at least one perfume raw material having a first vapor pressure greater than 0.08 Torr at 22° C. is present in an amount ranging from 3.2 to 40 wt % of the fragrance component. Alternatively, the second at least one perfume raw material having a first vapor pressure greater than 0.08 Torr at 22° C. is present in an amount ranging from 3.25 to 40 wt % of the fragrance component. Alternatively, the second at least one perfume raw material having a first vapor pressure greater than 0.08 Torr at 22° C. is present in an amount ranging from 3.3 to 40 wt % of the fragrance component. Alternatively, the second at least one perfume raw material having a first vapor pressure greater than 0.08 Torr at 22° C. is present in an amount ranging from 3.35 to 40 wt % of the fragrance component. Alternatively, the second at least one perfume raw material having a first vapor pressure greater than 0.08 Torr at 22° C. is present in an amount ranging from 3.4 to 40 wt % of the fragrance component. Alternatively, the second at least one perfume raw material having a first vapor pressure greater than 0.08 Torr at 22° C. is present in an amount ranging from 3.45 to 40 wt % of the fragrance component. Alternatively, the second at least one perfume raw material having a first vapor pressure greater than 0.08 Torr at 22° C. is present in an amount ranging from 3.5 to 40 wt % of the fragrance component. Alternatively, the second at least one perfume raw material having a first vapor pressure greater than 0.08 Torr at 22° C. is present in an amount ranging from 3.55 to 40 wt % of the fragrance component. Alternatively, the second at least one perfume raw material having a first vapor pressure greater than 0.08 Torr at 22° C. is present in an amount ranging from 3.6 to 40 wt % of the fragrance component. Alternatively, the second at least one perfume raw material having a first vapor pressure greater than 0.08 Torr at 22° C. is present in an amount ranging from 3.65 to 40 wt % of the fragrance component. Alternatively, the second at least one perfume raw material having a first vapor pressure greater than 0.08 Torr at 22° C. is present in an amount ranging from 3.7 to 40 wt % of the fragrance component. Alternatively, the second at least one perfume raw material having a first vapor pressure greater than 0.08 Torr at 22° C. is present in an amount ranging from 3.75 to 40 wt % of the fragrance component. Alternatively, the second at least one perfume raw material having a first vapor pressure greater than 0.08 Torr at 22° C. is present in an amount ranging from 3.8 to 40 wt % of the fragrance component. Alternatively, the second at least one perfume raw material having a first vapor pressure greater than 0.08 Torr at 22° C. is present in an amount ranging from 3.85 to 40 wt % of the fragrance component. Alternatively, the second at least one perfume raw material having a first vapor pressure greater than 0.08 Torr at 22° C. is present in an amount ranging from 3.9 to 40 wt % of the fragrance component. Alternatively, the second at least one perfume raw material having a first vapor pressure greater than 0.08 Torr at 22° C. is present in an amount ranging from 3.95 to 40 wt % of the fragrance component. Alternatively, the second at least one perfume raw material having a first vapor pressure greater than 0.08 Torr at 22° C. is present in an amount ranging from 4 to 40 wt % of the fragrance component. Alternatively, the second at least one perfume raw material having a first vapor pressure greater than 0.08 Torr at 22° C. is present in an amount ranging from 4.15 to 40 wt % of the fragrance component. Alternatively, the second at least one perfume raw material having a first vapor pressure greater than 0.08 Torr at 22° C. is present in an amount ranging from 4.2 to 40 wt % of the fragrance component. Alternatively, the second at least one perfume raw material having a first vapor pressure greater than 0.08 Torr at 22° C. is present in an amount ranging from 4.25 to 40 wt % of the fragrance component. Alternatively, the second at least one perfume raw material having a first vapor pressure greater than 0.08 Torr at 22° C. is present in an amount ranging from 4.3 to 40 wt % of the fragrance component. Alternatively, the second at least one perfume raw material having a first vapor pressure greater than 0.08 Torr at 22° C. is present in an amount ranging from 4.35 to 40 wt % of the fragrance component. Alternatively, the second at least one perfume raw material having a first vapor pressure greater than 0.08 Torr at 22° C. is present in an amount ranging from 4.4 to 40 wt % of the fragrance component. Alternatively, the second at least one perfume raw material having a first vapor pressure greater than 0.08 Torr at 22° C. is present in an amount ranging from 4.45 to 40 wt % of the fragrance component. Alternatively, the second at least one perfume raw material having a first vapor pressure greater than 0.08 Torr at 22° C. is present in an amount ranging from 4.5 to 40 wt % of the fragrance component. Alternatively, the second at least one perfume raw material having a first vapor pressure greater than 0.08 Torr at 22° C. is present in an amount ranging from 4.55 to 40 wt % of the fragrance component. Alternatively, the second at least one perfume raw material having a first vapor pressure greater than 0.08 Torr at 22° C. is present in an amount ranging from 4.6 to 40 wt % of the fragrance component. Alternatively, the second at least one perfume raw material having a first vapor pressure greater than 0.08 Torr at 22° C. is present in an amount ranging from 4.65 to 40 wt % of the fragrance component. Alternatively, the second at least one perfume raw material having a first vapor pressure greater than 0.08 Torr at 22° C. is present in an amount ranging from 4.7 to 40 wt % of the fragrance component. Alternatively, the second at least one perfume raw material having a first vapor pressure greater than 0.08 Torr at 22° C. is present in an amount ranging from 4.75 to 40 wt % of the fragrance component. Alternatively, the second at least one perfume raw material having a first vapor pressure greater than 0.08 Torr at 22° C. is present in an amount ranging from 4.8 to 40 wt % of the fragrance component. Alternatively, the second at least one perfume raw material having a first vapor pressure greater than 0.08 Torr at 22° C. is present in an amount ranging from 4.85 to 40 wt % of the fragrance component. Alternatively, the second at least one perfume raw material having a first vapor pressure greater than 0.08 Torr at 22° C. is present in an amount ranging from 4.9 to 40 wt % of the fragrance component. Alternatively, the second at least one perfume raw material having a first vapor pressure greater than 0.08 Torr at 22° C. is present in an amount ranging from 4.95 to 40 wt % of the fragrance component. Alternatively, the second at least one perfume raw material having a first vapor pressure greater than 0.08 Torr at 22° C. is present in an amount ranging from 5 to 40 wt % of the fragrance component. Alternatively, the second at least one perfume raw material having a first vapor pressure greater than 0.08 Torr at 22° C. is present in an amount ranging from 5.15 to 40 wt % of the fragrance component. Alternatively, the second at least one perfume raw material having a first vapor pressure greater than 0.08 Torr at 22° C. is present in an amount ranging from 5.2 to 40 wt % of the fragrance component. Alternatively, the second at least one perfume raw material having a first vapor pressure greater than 0.08 Torr at 22° C. is present in an amount ranging from 5.25 to 40 wt % of the fragrance component. Alternatively, the second at least one perfume raw material having a first vapor pressure greater than 0.08 Torr at 22° C. is present in an amount ranging from 5.3 to 40 wt % of the fragrance component. Alternatively, the second at least one perfume raw material having a first vapor pressure greater than 0.08 Torr at 22° C. is present in an amount ranging from 5.35 to 40 wt % of the fragrance component. Alternatively, the second at least one perfume raw material having a first vapor pressure greater than 0.08 Torr at 22° C. is present in an amount ranging from 5.4 to 40 wt % of the fragrance component. Alternatively, the second at least one perfume raw material having a first vapor pressure greater than 0.08 Torr at 22° C. is present in an amount ranging from 5.45 to 40 wt % of the fragrance component. Alternatively, the second at least one perfume raw material having a first vapor pressure greater than 0.08 Torr at 22° C. is present in an amount ranging from 5.5 to 40 wt % of the fragrance component. Alternatively, the second at least one perfume raw material having a first vapor pressure greater than 0.08 Torr at 22° C. is present in an amount ranging from 5.55 to 40 wt % of the fragrance component. Alternatively, the second at least one perfume raw material having a first vapor pressure greater than 0.08 Torr at 22° C. is present in an amount ranging from 5.6 to 40 wt % of the fragrance component. Alternatively, the second at least one perfume raw material having a first vapor pressure greater than 0.08 Torr at 22° C. is present in an amount ranging from 5.65 to 40 wt % of the fragrance component. Alternatively, the second at least one perfume raw material having a first vapor pressure greater than 0.08 Torr at 22° C. is present in an amount ranging from 5.7 to 40 wt % of the fragrance component. Alternatively, the second at least one perfume raw material having a first vapor pressure greater than 0.08 Torr at 22° C. is present in an amount ranging from 5.75 to 40 wt % of the fragrance component. Alternatively, the second at least one perfume raw material having a first vapor pressure greater than 0.08 Torr at 22° C. is present in an amount ranging from 5.8 to 40 wt % of the fragrance component. Alternatively, the second at least one perfume raw material having a first vapor pressure greater than 0.08 Torr at 22° C. is present in an amount ranging from 5.85 to 40 wt % of the fragrance component. Alternatively, the second at least one perfume raw material having a first vapor pressure greater than 0.08 Torr at 22° C. is present in an amount ranging from 5.9 to 40 wt % of the fragrance component. Alternatively, the second at least one perfume raw material having a first vapor pressure greater than 0.08 Torr at 22° C. is present in an amount ranging from 5.95 to 40 wt % of the fragrance component. Alternatively, the second at least one perfume raw material having a first vapor pressure greater than 0.08 Torr at 22° C. is present in an amount ranging from 6 to 40 wt % of the fragrance component. Alternatively, the second at least one perfume raw material having a first vapor pressure greater than 0.08 Torr at 22° C. is present in an amount ranging from 6.15 to 40 wt % of the fragrance component. Alternatively, the second at least one perfume raw material having a first vapor pressure greater than 0.08 Torr at 22° C. is present in an amount ranging from 6.2 to 40 wt % of the fragrance component. Alternatively, the second at least one perfume raw material having a first vapor pressure greater than 0.08 Torr at 22° C. is present in an amount ranging from 6.25 to 40 wt % of the fragrance component. Alternatively, the second at least one perfume raw material having a first vapor pressure greater than 0.08 Torr at 22° C. is present in an amount ranging from 6.3 to 40 wt % of the fragrance component. Alternatively, the second at least one perfume raw material having a first vapor pressure greater than 0.08 Torr at 22° C. is present in an amount ranging from 6.35 to 40 wt % of the fragrance component. Alternatively, the second at least one perfume raw material having a first vapor pressure greater than 0.08 Torr at 22° C. is present in an amount ranging from 6.4 to 40 wt % of the fragrance component. Alternatively, the second at least one perfume raw material having a first vapor pressure greater than 0.08 Torr at 22° C. is present in an amount ranging from 6.45 to 40 wt % of the fragrance component. Alternatively, the second at least one perfume raw material having a first vapor pressure greater than 0.08 Torr at 22° C. is present in an amount ranging from 6.5 to 40 wt % of the fragrance component. Alternatively, the second at least one perfume raw material having a first vapor pressure greater than 0.08 Torr at 22° C. is present in an amount ranging from 6.55 to 40 wt % of the fragrance component. Alternatively, the second at least one perfume raw material having a first vapor pressure greater than 0.08 Torr at 22° C. is present in an amount ranging from 6.6 to 40 wt % of the fragrance component. Alternatively, the second at least one perfume raw material having a first vapor pressure greater than 0.08 Torr at 22° C. is present in an amount ranging from 6.65 to 40 wt % of the fragrance component. Alternatively, the second at least one perfume raw material having a first vapor pressure greater than 0.08 Torr at 22° C. is present in an amount ranging from 6.7 to 40 wt % of the fragrance component. Alternatively, the second at least one perfume raw material having a first vapor pressure greater than 0.08 Torr at 22° C. is present in an amount ranging from 6.75 to 40 wt % of the fragrance component. Alternatively, the second at least one perfume raw material having a first vapor pressure greater than 0.08 Torr at 22° C. is present in an amount ranging from 6.8 to 40 wt % of the fragrance component. Alternatively, the second at least one perfume raw material having a first vapor pressure greater than 0.08 Torr at 22° C. is present in an amount ranging from 6.85 to 40 wt % of the fragrance component. Alternatively, the second at least one perfume raw material having a first vapor pressure greater than 0.08 Torr at 22° C. is present in an amount ranging from 6.9 to 40 wt % of the fragrance component. Alternatively, the second at least one perfume raw material having a first vapor pressure greater than 0.08 Torr at 22° C. is present in an amount ranging from 6.95 to 40 wt % of the fragrance component. Alternatively, the second at least one perfume raw material having a first vapor pressure greater than 0.08 Torr at 22° C. is present in an amount ranging from 7 to 40 wt % of the fragrance component. Alternatively, the second at least one perfume raw material having a first vapor pressure greater than 0.08 Torr at 22° C. is present in an amount ranging from 7.15 to 40 wt % of the fragrance component. Alternatively, the second at least one perfume raw material having a first vapor pressure greater than 0.08 Torr at 22° C. is present in an amount ranging from 7.2 to 40 wt % of the fragrance component. Alternatively, the second at least one perfume raw material having a first vapor pressure greater than 0.08 Torr at 22° C. is present in an amount ranging from 7.25 to 40 wt % of the fragrance component. Alternatively, the second at least one perfume raw material having a first vapor pressure greater than 0.08 Torr at 22° C. is present in an amount ranging from 7.3 to 40 wt % of the fragrance component. Alternatively, the second at least one perfume raw material having a first vapor pressure greater than 0.08 Torr at 22° C. is present in an amount ranging from 7.35 to 40 wt % of the fragrance component. Alternatively, the second at least one perfume raw material having a first vapor pressure greater than 0.08 Torr at 22° C. is present in an amount ranging from 7.4 to 40 wt % of the fragrance component. Alternatively, the second at least one perfume raw material having a first vapor pressure greater than 0.08 Torr at 22° C. is present in an amount ranging from 7.45 to 40 wt % of the fragrance component. Alternatively, the second at least one perfume raw material having a first vapor pressure greater than 0.08 Torr at 22° C. is present in an amount ranging from 7.5 to 40 wt % of the fragrance component. Alternatively, the second at least one perfume raw material having a first vapor pressure greater than 0.08 Torr at 22° C. is present in an amount ranging from 7.55 to 40 wt % of the fragrance component. Alternatively, the second at least one perfume raw material having a first vapor pressure greater than 0.08 Torr at 22° C. is present in an amount ranging from 7.6 to 40 wt % of the fragrance component. Alternatively, the second at least one perfume raw material having a first vapor pressure greater than 0.08 Torr at 22° C. is present in an amount ranging from 7.65 to 40 wt % of the fragrance component. Alternatively, the second at least one perfume raw material having a first vapor pressure greater than 0.08 Torr at 22° C. is present in an amount ranging from 7.7 to 40 wt % of the fragrance component. Alternatively, the second at least one perfume raw material having a first vapor pressure greater than 0.08 Torr at 22° C. is present in an amount ranging from 7.75 to 40 wt % of the fragrance component. Alternatively, the second at least one perfume raw material having a first vapor pressure greater than 0.08 Torr at 22° C. is present in an amount ranging from 7.8 to 40 wt % of the fragrance component. Alternatively, the second at least one perfume raw material having a first vapor pressure greater than 0.08 Torr at 22° C. is present in an amount ranging from 7.85 to 40 wt % of the fragrance component. Alternatively, the second at least one perfume raw material having a first vapor pressure greater than 0.08 Torr at 22° C. is present in an amount ranging from 7.9 to 40 wt % of the fragrance component. Alternatively, the second at least one perfume raw material having a first vapor pressure greater than 0.08 Torr at 22° C. is present in an amount ranging from 7.95 to 40 wt % of the fragrance component. Alternatively, the second at least one perfume raw material having a first vapor pressure greater than 0.08 Torr at 22° C. is present in an amount ranging from 8 to 40 wt % of the fragrance component. Alternatively, the second at least one perfume raw material having a first vapor pressure greater than 0.08 Torr at 22° C. is present in an amount ranging from 8.15 to 40 wt % of the fragrance component. Alternatively, the second at least one perfume raw material having a first vapor pressure greater than 0.08 Torr at 22° C. is present in an amount ranging from 8.2 to 40 wt % of the fragrance component. Alternatively, the second at least one perfume raw material having a first vapor pressure greater than 0.08 Torr at 22° C. is present in an amount ranging from 8.25 to 40 wt % of the fragrance component. Alternatively, the second at least one perfume raw material having a first vapor pressure greater than 0.08 Torr at 22° C. is present in an amount ranging from 8.3 to 40 wt % of the fragrance component. Alternatively, the second at least one perfume raw material having a first vapor pressure greater than 0.08 Torr at 22° C. is present in an amount ranging from 8.35 to 40 wt % of the fragrance component. Alternatively, the second at least one perfume raw material having a first vapor pressure greater than 0.08 Torr at 22° C. is present in an amount ranging from 8.4 to 40 wt % of the fragrance component. Alternatively, the second at least one perfume raw material having a first vapor pressure greater than 0.08 Torr at 22° C. is present in an amount ranging from 8.45 to 40 wt % of the fragrance component. Alternatively, the second at least one perfume raw material having a first vapor pressure greater than 0.08 Torr at 22° C. is present in an amount ranging from 8.5 to 40 wt % of the fragrance component. Alternatively, the second at least one perfume raw material having a first vapor pressure greater than 0.08 Torr at 22° C. is present in an amount ranging from 8.55 to 40 wt % of the fragrance component. Alternatively, the second at least one perfume raw material having a first vapor pressure greater than 0.08

Torr at 22° C. is present in an amount ranging from 8.6 to 40 wt % of the fragrance component. Alternatively, the second at least one perfume raw material having a first vapor pressure greater than 0.08 Torr at 22° C. is present in an amount ranging from 8.65 to 40 wt % of the fragrance component. Alternatively, the second at least one perfume raw material having a first vapor pressure greater than 0.08 Torr at 22° C. is present in an amount ranging from 8.7 to 40 wt % of the fragrance component. Alternatively, the second at least one perfume raw material having a first vapor pressure greater than 0.08 Torr at 22° C. is present in an amount ranging from 8.75 to 40 wt % of the fragrance component. Alternatively, the second at least one perfume raw material having a first vapor pressure greater than 0.08 Torr at 22° C. is present in an amount ranging from 8.8 to 40 wt % of the fragrance component. Alternatively, the second at least one perfume raw material having a first vapor pressure greater than 0.08 Torr at 22° C. is present in an amount ranging from 8.85 to 40 wt % of the fragrance component. Alternatively, the second at least one perfume raw material having a first vapor pressure greater than 0.08 Torr at 22° C. is present in an amount ranging from 8.9 to 40 wt % of the fragrance component. Alternatively, the second at least one perfume raw material having a first vapor pressure greater than 0.08 Torr at 22° C. is present in an amount ranging from 8.95 to 40 wt % of the fragrance component. Alternatively, the second at least one perfume raw material having a first vapor pressure greater than 0.08 Torr at 22° C. is present in an amount ranging from 9 to 40 wt % of the fragrance component. Alternatively, the second at least one perfume raw material having a first vapor pressure greater than 0.08 Torr at 22° C. is present in an amount ranging from 9.15 to 40 wt % of the fragrance component. Alternatively, the second at least one perfume raw material having a first vapor pressure greater than 0.08 Torr at 22° C. is present in an amount ranging from 9.2 to 40 wt % of the fragrance component. Alternatively, the second at least one perfume raw material having a first vapor pressure greater than 0.08 Torr at 22° C. is present in an amount ranging from 9.25 to 40 wt % of the fragrance component. Alternatively, the second at least one perfume raw material having a first vapor pressure greater than 0.08 Torr at 22° C. is present in an amount ranging from 9.3 to 40 wt % of the fragrance component. Alternatively, the second at least one perfume raw material having a first vapor pressure greater than 0.08 Torr at 22° C. is present in an amount ranging from 9.35 to 40 wt % of the fragrance component. Alternatively, the second at least one perfume raw material having a first vapor pressure greater than 0.08 Torr at 22° C. is present in an amount ranging from 9.4 to 40 wt % of the fragrance component. Alternatively, the second at least one perfume raw material having a first vapor pressure greater than 0.08 Torr at 22° C. is present in an amount ranging from 9.45 to 40 wt % of the fragrance component. Alternatively, the second at least one perfume raw material having a first vapor pressure greater than 0.08 Torr at 22° C. is present in an amount ranging from 9.5 to 40 wt % of the fragrance component. Alternatively, the second at least one perfume raw material having a first vapor pressure greater than 0.08 Torr at 22° C. is present in an amount ranging from 9.55 to 40 wt % of the fragrance component. Alternatively, the second at least one perfume raw material having a first vapor pressure greater than 0.08 Torr at 22° C. is present in an amount ranging from 9.6 to 40 wt % of the fragrance component. Alternatively, the second at least one perfume raw material having a first vapor pressure greater than 0.08 Torr at 22° C. is present in an amount ranging from 9.65 to 40 wt % of the fragrance component. Alternatively, the second at least one perfume raw material having a first vapor pressure greater than 0.08 Torr at 22° C. is present in an amount ranging from 9.7 to 40 wt % of the fragrance component. Alternatively, the second at least one perfume raw material having a first vapor pressure greater than 0.08 Torr at 22° C. is present in an amount ranging from 9.75 to 40 wt % of the fragrance component. Alternatively, the second at least one perfume raw material having a first vapor pressure greater than 0.08 Torr at 22° C. is present in an amount ranging from 9.8 to 40 wt % of the fragrance component. Alternatively, the second at least one perfume raw material having a first vapor pressure greater than 0.08 Torr at 22° C. is present in an amount ranging from 9.85 to 40 wt % of the fragrance component. Alternatively, the second at least one perfume raw material having a first vapor pressure greater than 0.08 Torr at 22° C. is present in an amount ranging from 9.9 to 40 wt % of the fragrance component. Alternatively, the second at least one perfume raw material having a first vapor pressure greater than 0.08 Torr at 22° C. is present in an amount ranging from 9.95 to 40 wt % of the fragrance component. Alternatively, the second at least one perfume raw material having a first vapor pressure greater than 0.08 Torr at 22° C. is present in an amount ranging from 10 to 40 wt % of the fragrance component. Alternatively, the second at least one perfume raw material having a first vapor pressure greater than 0.08 Torr at 22° C. is present in an amount ranging from 15 to 40 wt % of the fragrance component. Alternatively, the second at least one perfume raw material having a first vapor pressure greater than 0.08 Torr at 22° C. is present in an amount ranging from 20 to 40 wt % of the fragrance component. Alternatively, the second at least one perfume raw material having a first vapor pressure greater than 0.08 Torr at 22° C. is present in an amount ranging from 25 to 40 wt % of the fragrance component. Alternatively, the second at least one perfume raw material having a first vapor pressure greater than 0.08 Torr at 22° C. is present in an amount ranging from 30 to 40 wt % of the fragrance component. Alternatively, the second at least one perfume raw material having a first vapor pressure greater than 0.08 Torr at 22° C. is present in an amount ranging from 35 to 40 wt % of the fragrance component.

Alternatively, the second at least one perfume raw material having a first vapor pressure greater than 0.08 Torr at 22° C. is present in an amount ranging from 0.1 to 35 wt % of the fragrance component. Alternatively, the second at least one perfume raw material having a first vapor pressure greater than 0.08 Torr at 22° C. is present in an amount ranging from 0.1 to 30 wt % of the fragrance component. Alternatively, the second at least one perfume raw material having a first vapor pressure greater than 0.08 Torr at 22° C. is present in an amount ranging from 0.1 to 25 wt % of the fragrance component. Alternatively, the second at least one perfume raw material having a first vapor pressure greater than 0.08 Torr at 22° C. is present in an amount ranging from 0.1 to 20 wt % of the fragrance component. Alternatively, the second at least one perfume raw material having a first vapor pressure greater than 0.08 Torr at 22° C. is present in an amount ranging from 0.1 to 15 wt % of the fragrance component. Alternatively, the second at least one perfume raw material having a first vapor pressure greater than 0.08 Torr at 22° C. is present in an amount ranging from 0.1 to 10 wt % of the fragrance component. Alternatively, the second at least one perfume raw material having a first vapor pressure greater than 0.08 Torr at 22° C. is present in an amount ranging from 0.1 to 9.9 wt % of the fragrance component. Alternatively, the second at least one perfume raw material having a first vapor pressure greater than 0.08 Torr at 22° C. is present in an amount ranging from 0.1 to 9.8 wt % of the fragrance component. Alternatively, the second at least one perfume raw material having a first vapor pressure greater than 0.08 Torr at 22° C. is present in an amount ranging from 0.1 to 9.7 wt % of the fragrance component. Alternatively, the second at least one perfume raw material having a first vapor pressure greater than 0.08 Torr at 22° C. is present in an amount ranging from 0.1 to 9.6 wt % of the fragrance component. Alternatively, the second at least one perfume raw material having a first vapor pressure greater than 0.08 Torr at 22° C. is present in an amount ranging from 0.1 to 9.5 wt % of the fragrance component. Alternatively, the second at least one perfume raw material having a first vapor pressure greater than 0.08 Torr at 22° C. is present in an amount ranging from 0.1 to 9.4 wt % of the fragrance component. Alternatively, the second at least one perfume raw material having a first vapor pressure greater than 0.08 Torr at 22° C. is present in an amount ranging from 0.1 to 9.3 wt % of the fragrance component. Alternatively, the second at least one perfume raw material having a first vapor pressure greater than 0.08 Torr at 22° C. is present in an amount ranging from 0.1 to 9.2 wt % of the fragrance component. Alternatively, the second at least one perfume raw material having a first vapor pressure greater than 0.08 Torr at 22° C. is present in an amount ranging from 0.1 to 9.1 wt % of the fragrance component. Alternatively, the second at least one perfume raw material having a first vapor pressure greater than 0.08 Torr at 22° C. is present in an amount ranging from 0.1 to 9 wt % of the fragrance component. Alternatively, the second at least one perfume raw material having a first vapor pressure greater than 0.08 Torr at 22° C. is present in an amount ranging from 0.1 to 8.9 wt % of the fragrance component. Alternatively, the second at least one perfume raw material having a first vapor pressure greater than 0.08 Torr at 22° C. is present in an amount ranging from 0.1 to 8.8 wt % of the fragrance component. Alternatively, the second at least one perfume raw material having a first vapor pressure greater than 0.08 Torr at 22° C. is present in an amount ranging from 0.1 to 8.7 wt % of the fragrance component. Alternatively, the second at least one perfume raw material having a first vapor pressure greater than 0.08 Torr at 22° C. is present in an amount ranging from 0.1 to 8.6 wt % of the fragrance component. Alternatively, the second at least one perfume raw material having a first vapor pressure greater than 0.08 Torr at 22° C. is present in an amount ranging from 0.1 to 8.5 wt % of the fragrance component. Alternatively, the second at least one perfume raw material having a first vapor pressure greater than 0.08 Torr at 22° C. is present in an amount ranging from 0.1 to 8.4 wt % of the fragrance component. Alternatively, the second at least one perfume raw material having a first vapor pressure greater than 0.08 Torr at 22° C. is present in an amount ranging from 0.1 to 8.3 wt % of the fragrance component. Alternatively, the second at least one perfume raw material having a first vapor pressure greater than 0.08 Torr at 22° C. is present in an amount ranging from 0.1 to 8.2 wt % of the fragrance component. Alternatively, the second at least one perfume raw material having a first vapor pressure greater than 0.08 Torr at 22° C. is present in an amount ranging from 0.1 to 8.1 wt % of the fragrance component. Alternatively, the second at least one perfume raw material having a first vapor pressure greater than 0.08 Torr at 22° C. is present in an amount ranging from 0.1 to 8 wt % of the fragrance component. Alternatively, the second at least one perfume raw material having a first vapor pressure greater than 0.08 Torr at 22° C. is present in an amount ranging from 0.1 to 7.9 wt % of the fragrance component. Alternatively, the second at least one perfume raw material having a first vapor pressure greater than 0.08 Torr at 22° C. is present in an amount ranging from 0.1 to 7.8 wt % of the fragrance component. Alternatively, the second at least one perfume raw material having a first vapor pressure greater than 0.08 Torr at 22° C. is present in an amount ranging from 0.1 to 7.7 wt % of the fragrance component. Alternatively, the second at least one perfume raw material having a first vapor pressure greater than 0.08 Torr at 22° C. is present in an amount ranging from 0.1 to 7.6 wt % of the fragrance component. Alternatively, the second at least one perfume raw material having a first vapor pressure greater than 0.08 Torr at 22° C. is present in an amount ranging from 0.1 to 7.5 wt % of the fragrance component. Alternatively, the second at least one perfume raw material having a first vapor pressure greater than 0.08 Torr at 22° C. is present in an amount ranging from 0.1 to 7.4 wt % of the fragrance component. Alternatively, the second at least one perfume raw material having a first vapor pressure greater than 0.08 Torr at 22° C. is present in an amount ranging from 0.1 to 7.3 wt % of the fragrance component. Alternatively, the second at least one perfume raw material having a first vapor pressure greater than 0.08 Torr at 22° C. is present in an amount ranging from 0.1 to 7.2 wt % of the fragrance component. Alternatively, the second at least one perfume raw material having a first vapor pressure greater than 0.08 Torr at 22° C. is present in an amount ranging from 0.1 to 7.1 wt % of the fragrance component. Alternatively, the second at least one perfume raw material having a first vapor pressure greater than 0.08 Torr at 22° C. is present in an amount ranging from 0.1 to 7 wt % of the fragrance component. Alternatively, the second at least one perfume raw material having a first vapor pressure greater than 0.08 Torr at 22° C. is present in an amount ranging from 0.1 to 6.9 wt % of the fragrance component. Alternatively, the second at least one perfume raw material having a first vapor pressure greater than 0.08 Torr at 22° C. is present in an amount ranging from 0.1 to 6.8 wt % of the fragrance component. Alternatively, the second at least one perfume raw material having a first vapor pressure greater than 0.08 Torr at 22° C. is present in an amount ranging from 0.1 to 6.7 wt % of the fragrance component. Alternatively, the second at least one perfume raw material having a first vapor pressure greater than 0.08 Torr at 22° C. is present in an amount ranging from 0.1 to 6.6 wt % of the fragrance component. Alternatively, the second at least one perfume raw material having a first vapor pressure greater than 0.08 Torr at 22° C. is present in an amount ranging from 0.1 to 6.5 wt % of the fragrance component. Alternatively, the second at least one perfume raw material having a first vapor pressure greater than 0.08 Torr at 22° C. is present in an amount ranging from 0.1 to 6.4 wt % of the fragrance component. Alternatively, the second at least one perfume raw material having a first vapor pressure greater than 0.08 Torr at 22° C. is present in an amount ranging from 0.1 to 6.3 wt % of the fragrance component. Alternatively, the second at least one perfume raw material having a first vapor pressure greater than 0.08 Torr at 22° C. is present in an amount ranging from 0.1 to 6.2 wt % of the fragrance component. Alternatively, the second at least one perfume raw material having a first vapor pressure greater than 0.08 Torr at 22° C. is present in an amount ranging from 0.1 to 6.1 wt % of the fragrance component. Alternatively, the second at least one perfume raw material having a first vapor pressure greater than 0.08 Torr at 22° C. is present in an amount ranging from 0.1 to 6 wt % of the fragrance component. Alternatively, the second at least one perfume raw material having a first vapor pressure greater than 0.08 Torr at 22° C. is present in an amount ranging from 0.1 to 5.9 wt % of the fragrance component. Alternatively, the second at least one perfume raw material having a first vapor pressure greater than 0.08 Torr at 22° C. is present in an amount ranging from 0.1 to 5.8 wt % of the fragrance component. Alternatively, the second at least one perfume raw material having a first vapor pressure greater than 0.08 Torr at 22° C. is present in an amount ranging from 0.1 to 5.7 wt % of the fragrance component. Alternatively, the second at least one perfume raw material having a first vapor pressure greater than 0.08 Torr at 22° C. is present in an amount ranging from 0.1 to 5.6 wt % of the fragrance component. Alternatively, the second at least one perfume raw material having a first vapor pressure greater than 0.08 Torr at 22° C. is present in an amount ranging from 0.1 to 5.5 wt % of the fragrance component. Alternatively, the second at least one perfume raw material having a first vapor pressure greater than 0.08 Torr at 22° C. is present in an amount ranging from 0.1 to 5.4 wt % of the fragrance component. Alternatively, the second at least one perfume raw material having a first vapor pressure greater than 0.08 Torr at 22° C. is present in an amount ranging from 0.1 to 5.3 wt % of the fragrance component. Alternatively, the second at least one perfume raw material having a first vapor pressure greater than 0.08 Torr at 22° C. is present in an amount ranging from 0.1 to 5.2 wt % of the fragrance component. Alternatively, the second at least one perfume raw material having a first vapor pressure greater than 0.08 Torr at 22° C. is present in an amount ranging from 0.1 to 5.1 wt % of the fragrance component. Alternatively, the second at least one perfume raw material having a first vapor pressure greater than 0.08 Torr at 22° C. is present in an amount ranging from 0.1 to 5 wt % of the fragrance component. Alternatively, the second at least one perfume raw material having a first vapor pressure greater than 0.08 Torr at 22° C. is present in an amount ranging from 0.1 to 4.9 wt % of the fragrance component. Alternatively, the second at least one perfume raw material having a first vapor pressure greater than 0.08 Torr at 22° C. is present in an amount ranging from 0.1 to 4.8 wt % of the fragrance component. Alternatively, the second at least one perfume raw material having a first vapor pressure greater than 0.08 Torr at 22° C. is present in an amount ranging from 0.1 to 4.7 wt % of the fragrance component. Alternatively, the second at least one perfume raw material having a first vapor pressure greater than 0.08 Torr at 22° C. is present in an amount ranging from 0.1 to 4.6 wt % of the fragrance component. Alternatively, the second at least one perfume raw material having a first vapor pressure greater than 0.08 Torr at 22° C. is present in an amount ranging from 0.1 to 4.5 wt % of the fragrance component. Alternatively, the second at least one perfume raw material having a first vapor pressure greater than 0.08 Torr at 22° C. is present in an amount ranging from 0.1 to 4.4 wt % of the fragrance component. Alternatively, the second at least one perfume raw material having a first vapor pressure greater than 0.08 Torr at 22° C. is present in an amount ranging from 0.1 to 4.3 wt % of the fragrance component. Alternatively, the second at least one perfume raw material having a first vapor pressure greater than 0.08 Torr at 22° C. is present in an amount ranging from 0.1 to 4.2 wt % of the fragrance component. Alternatively, the second at least one perfume raw material having a first vapor pressure greater than 0.08 Torr at 22° C. is present in an amount ranging from 0.1 to 4.1 wt % of the fragrance component. Alternatively, the second at least one perfume raw material having a first vapor pressure greater than 0.08 Torr at 22° C. is present in an amount ranging from 0.1 to 4 wt % of the fragrance component. Alternatively, the second at least one perfume raw material having a first vapor pressure greater than 0.08 Torr at 22° C. is present in an amount ranging from 0.1 to 3.9 wt % of the fragrance component. Alternatively, the second at least one perfume raw material having a first vapor pressure greater than 0.08 Torr at 22° C. is present in an amount ranging from 0.1 to 3.8 wt % of the fragrance component. Alternatively, the second at least one perfume raw material having a first vapor pressure greater than 0.08 Torr at 22° C. is present in an amount ranging from 0.1 to 3.7 wt % of the fragrance component. Alternatively, the second at least one perfume raw material having a first vapor pressure greater than 0.08 Torr at 22° C. is present in an amount ranging from 0.1 to 3.6 wt % of the fragrance component. Alternatively, the second at least one perfume raw material having a first vapor pressure greater than 0.08 Torr at 22° C. is present in an amount ranging from 0.1 to 3.5 wt % of the fragrance component. Alternatively, the second at least one perfume raw material having a first vapor pressure greater than 0.08 Torr at 22° C. is present in an amount ranging from 0.1 to 3.4 wt % of the fragrance component. Alternatively, the second at least one perfume raw material having a first vapor pressure greater than 0.08 Torr at 22° C. is present in an amount ranging from 0.1 to 3.3 wt % of the fragrance component. Alternatively, the second at least one perfume raw material having a first vapor pressure greater than 0.08 Torr at 22° C. is present in an amount ranging from 0.1 to 3.2 wt % of the fragrance component. Alternatively, the second at least one perfume raw material having a first vapor pressure greater than 0.08 Torr at 22° C. is present in an amount ranging from 0.1 to 3.1 wt % of the fragrance component. Alternatively, the second at least one perfume raw material having a first vapor pressure greater than 0.08 Torr at 22° C. is present in an amount ranging from 0.1 to 3 wt % of the fragrance component. Alternatively, the second at least one perfume raw material having a first vapor pressure greater than 0.08 Torr at 22° C. is present in an amount ranging from 0.1 to 2.9 wt % of the fragrance component. Alternatively, the second at least one perfume raw material having a first vapor pressure greater than 0.08 Torr at 22° C. is present in an amount ranging from 0.1 to 2.8 wt % of the fragrance component. Alternatively, the second at least one perfume raw material having a first vapor pressure greater than 0.08 Torr at 22° C. is present in an amount ranging from 0.1 to 2.7 wt % of the fragrance component. Alternatively, the second at least one perfume raw material having a first vapor pressure greater than 0.08 Torr at 22° C. is present in an amount ranging from 0.1 to 2.6 wt % of the fragrance component. Alternatively, the second at least one perfume raw material having a first vapor pressure greater than 0.08 Torr at 22° C. is present in an amount ranging from 0.1 to 2.5 wt % of the fragrance component. Alternatively, the second at least one perfume raw material having a first vapor pressure greater than 0.08 Torr at 22° C. is present in an amount ranging from 0.1 to 2.4 wt % of the fragrance component. Alternatively, the second at least one perfume raw material having a first vapor pressure greater than 0.08 Torr at 22° C. is present in an amount ranging from 0.1 to 2.3 wt % of the fragrance component. Alternatively, the second at least one perfume raw material having a first vapor pressure greater than 0.08 Torr at 22° C. is present in an amount ranging from 0.1 to 2.2 wt % of the fragrance component. Alternatively, the second at least one perfume raw material having a first vapor pressure greater than 0.08 Torr at 22° C. is present in an amount ranging from 0.1 to 2.1 wt % of the fragrance component. Alternatively, the second at least one perfume raw material having a first vapor pressure greater than 0.08 Torr at 22° C. is present in an amount ranging from 0.1 to 2 wt % of the fragrance component. Alternatively, the second at least one perfume raw material having a first vapor pressure greater than 0.08 Torr at 22° C. is present in an amount ranging from 0.1 to 1.9 wt % of the fragrance component. Alternatively, the second at least one perfume raw material having a first vapor pressure greater than 0.08 Torr at 22° C. is present in an amount ranging from 0.1 to 1.8 wt % of the fragrance component. Alternatively, the second at least one perfume raw material having a first vapor pressure greater than 0.08 Torr at 22° C. is present in an amount ranging from 0.1 to 1.7 wt % of the fragrance component. Alternatively, the second at least one perfume raw material having a first vapor pressure greater than 0.08 Torr at 22° C. is present in an amount ranging from 0.1 to 1.6 wt % of the fragrance component. Alternatively, the second at least one perfume raw material having a first vapor pressure greater than 0.08 Torr at 22° C. is present in an amount ranging from 0.1 to 1.5 wt % of the fragrance component. Alternatively, the second at least one perfume raw material having a first vapor pressure greater than 0.08 Torr at 22° C. is present in an amount ranging from 0.1 to 1.4 wt % of the fragrance component. Alternatively, the second at least one perfume raw material having a first vapor pressure greater than 0.08 Torr at 22° C. is present in an amount ranging from 0.1 to 1.3 wt % of the fragrance component. Alternatively, the second at least one perfume raw material having a first vapor pressure greater than 0.08 Torr at 22° C. is present in an amount ranging from 0.1 to 1.2 wt % of the fragrance component. Alternatively, the second at least one perfume raw material having a first vapor pressure greater than 0.08 Torr at 22° C. is present in an amount ranging from 0.1 to 1.1 wt % of the fragrance component. Alternatively, the second at least one perfume raw material having a first vapor pressure greater than 0.08 Torr at 22° C. is present in an amount ranging from 0.1 to 1 wt % of the fragrance component. Alternatively, the second at least one perfume raw material having a first vapor pressure greater than 0.08 Torr at 22° C. is present in an amount ranging from 0.1 to 0.9 wt % of the fragrance component. Alternatively, the second at least one perfume raw material having a first vapor pressure greater than 0.08 Torr at 22° C. is present in an amount ranging from 0.1 to 0.8 wt % of the fragrance component. Alternatively, the second at least one perfume raw material having a first vapor pressure greater than 0.08 Torr at 22° C. is present in an amount ranging from 0.1 to 0.7 wt % of the fragrance component. Alternatively, the second at least one perfume raw material having a first vapor pressure greater than 0.08 Torr at 22° C. is present in an amount ranging from 0.1 to 0.6 wt % of the fragrance component. Alternatively, the second at least one perfume raw material having a first vapor pressure greater than 0.08 Torr at 22° C. is present in an amount ranging from 0.1 to 0.5 wt % of the fragrance component. Alternatively, the second at least one perfume raw material having a first vapor pressure greater than 0.08 Torr at 22° C. is present in an amount ranging from 0.1 to 0.4 wt % of the fragrance component. Alternatively, the second at least one perfume raw material having a first vapor pressure greater than 0.08 Torr at 22° C. is present in an amount ranging from 0.1 to 0.3 wt % of the fragrance component. Alternatively, the second at least one perfume raw material having a first vapor pressure greater than 0.08 Torr at 22° C. is present in an amount ranging from 0.1 to 0.2 wt % of the fragrance component.

In some aspects, the second at least one perfume raw material having a first vapor pressure greater than 0.08 Torr at 22° C. is present at 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 4.15, 4.2, 4.25, 4.3, 4.35, 4.4, 4.45, 4.5, 4.55, 4.6, 4.65, 4.7, 4.75, 4.8, 4.85, 4.9, 4.95, 5, 5.15, 5.2, 5.25, 5.3, 5.35, 5.4, 5.45, 5.5, 5.55, 5.6, 5.65, 5.7, 5.75, 5.8, 5.85, 5.9, 5.95, 6, 6.15, 6.2, 6.25, 6.3, 6.35, 6.4, 6.45, 6.5, 6.55, 6.6, 6.65, 6.7, 6.75, 6.8, 6.85, 6.9, 6.95, 7, 7.15, 7.2, 7.25, 7.3, 7.35, 7.4, 7.45, 7.5, 7.55, 7.6, 7.65, 7.7, 7.75, 7.8, 7.85, 7.9, 7.95, 8, 8.15, 8.2, 8.25, 8.3, 8.35, 8.4, 8.45, 8.5, 8.55, 8.6, 8.65, 8.7, 8.75, 8.8, 8.85, 8.9, 8.95, 9, 9.15, 9.2, 9.25, 9.3, 9.35, 9.4, 9.45, 9.5, 9.55, 9.6, 9.65, 9.7, 9.75, 9.8, 9.85, 9.9, 9.95, 10, 15, 20, 25, 30, 35, or 40 wt % of the fragrance component.

In one aspect, the medium volatility component comprises the second at least one perfume raw material having a first vapor pressure range of 0.0008 to 0.08 Torr at 22° C. in an amount from 20 to 45 wt % of the fragrance component. Alternatively, the second at least one perfume raw material having a first vapor pressure range of 0.0008 to 0.08 Torr at 22° C. is present in an amount ranging from 20 to 40 wt % of the fragrance component. Alternatively, the second at least one perfume raw material having a first vapor pressure range of 0.0008 to 0.08 Torr at 22° C. is present in an amount ranging from 25 to 40 wt % of the fragrance component. Alternatively, the second at least one perfume raw material having a first vapor pressure range of 0.0008 to 0.08 Torr at 22° C. is present in an amount ranging from 30 to 40 wt % of the fragrance component. Alternatively, the second at least one perfume raw material having a first vapor pressure range of 0.0008 to 0.08 Torr at 22° C. is present in an amount ranging from 35 to 40 wt % of the fragrance component.

Alternatively, the second at least one perfume raw material having a first vapor pressure range of 0.0008 to 0.08 Torr at 22° C. is present in an amount ranging from 20 to 40 wt % of the fragrance component. Alternatively, the second at least one perfume raw material having a first vapor pressure range of 0.0008 to 0.08 Torr at 22° C. is present in an amount ranging from 20 to 35 wt % of the fragrance component. Alternatively, the second at least one perfume raw material having a first vapor pressure range of 0.0008 to 0.08 Torr at 22° C. is present in an amount ranging from 20 to 30 wt % of the fragrance component. Alternatively, the second at least one perfume raw material having a first vapor pressure range of 0.0008 to 0.08 Torr at 22° C. is present in an amount ranging from 20 to 25 wt % of the fragrance component.

In some aspects, the second at least one perfume raw material having a first vapor pressure range of 0.0008 to 0.08 Torr at 22° C. is present at 20, 25, 30, 35, 40, or 45 wt % of the fragrance component.

In one aspect, the fragrance component further comprises at least one perfume raw material having a first vapor pressure less than 0.0008 Torr at 22° C. in an amount from 10 to 55 wt % of the fragrance component.

In one aspect, the fragrance component further comprises at least one perfume raw material having a first vapor pressure less than 0.0008 Torr at 22° C. in an amount from 30 to 55 wt % of the fragrance component.

In one aspect, the fragrance component further comprises at least one perfume raw material having a first vapor pressure less than 0.0008 Torr at 22° C. in an amount from 10 to 30 wt % of the fragrance component.

The at Least One Modulator: The compositions presented herein further comprise at least one modulator. Without intending to be limited to any particular theory, the at least one modulator is configured to allow a perfumer to formulate a fragrance profile with an accord, such as, for example, a floral, or a fruity, or an aromatic, or a spicy, or an oriental accord characteristic of the middle notes, which can last for very long periods, especially throughout the life of the composition after its application, without giving way to the stronger odors of the base notes. In addition the modulator is configured to allow a perfumer to utilize modulators in a manner that does not affect the consumer's initial perception of a fragrance profile: For example, a perfumer may select, based on a perfume raw materials calculated second vapor pressure, a top note that does not decrease in volatility in the presence of a modulator at a particular concentration. Moreover, the modulator is configured to reduce, prevent, or ameliorate the formation of a film on the consumer's skin.

In another aspect, the at least one modulator is configured to allow the removal of water from perfume compositions without negatively impacting the performance of the perfuming compositions.

In one aspect, the at least one modulator comprises a compound having:
  i. a vapor pressure of less than 0.0008 Torr at 22° C.;
  ii. at least two Hansen solubility parameters selected from a first group consisting of: an atomic dispersion force ($\delta_d$) from 12 to 20, a dipole moment ($\delta_p$) from 1 to 7, and a hydrogen bonding ($\delta_h$) from 2.5 to 11, when in solution with a compound having a vapor pressure greater than 0.08 Torr at 22° C.; and
  iii. at least two Hansen solubility parameters selected from a second group consisting of: an atomic dispersion force ($\delta_d$) from 14 to 20, a dipole moment ($\delta_p$) from 1 to 8, and a hydrogen bonding ($\delta_h$) from 4 to 11, when in solution with a compound having a vapor pressure range of 0.0008 to 0.08 Torr at 22° C.

In one aspect, the first group comprises at least two Hansen solubility parameters selected from the group consisting of: an atomic dispersion force ($\delta_d$) of 15.84±3.56, a dipole moment ($\delta_p$) of 4.15±2.65, and a hydrogen bonding ($\delta_h$) of 6.72±4.11, when in solution with a compound having a vapor pressure greater than 0.08 Torr at 22° C.

In one aspect, the second group comprises at least two Hansen solubility parameters selected from the group consisting of: an atomic dispersion force ($\delta_d$) of 16.86±2.72, a dipole moment ($\delta_p$) of 4.61±3.10, and a hydrogen bonding ($\delta_h$) of 7.66±3.29, when in solution with a compound having a vapor pressure range of 0.0008 to 0.08 Torr at 22° C.

Without intending to be limited to any particular theory, an at least one modulator having (i) at least two Hansen solubility parameters selected from a first group consisting of: an atomic dispersion force ($\delta_d$) from 12 to 20, a dipole moment ($\delta_p$) from 1 to 7, and a hydrogen bonding ($\delta_h$) from 2.5 to 11, when in solution with a compound having a vapor pressure greater than 0.08 Torr at 22° C.; and (ii) at least two Hansen solubility parameters selected from a second group consisting of: an atomic dispersion force ($\delta_d$) from 14 to 20, a dipole moment ($\delta_p$) from 1 to 8, and a hydrogen bonding ($\delta_h$) from 4 to 11, when in solution with a compound having a vapor pressure range of 0.0008 to 0.08 Torr at 22° C. are located within the area denoted by the dashed line and the solid line. Additionally, compounds having a c Log P value from 1.5 to 3.5 are marked with triangles. Such compounds may be incorporated into capsules or cyclodextrin.

In some aspects, the at least one modulator is selected from the compounds listed in Table 9.

In some aspects, the at least one modulator has an odor value from 1 to 10,000.

In some aspects, the at least one modulator has a $C_{I2.5}$ from 0.1 and 10 µg/l.

TABLE 9

Examples of some at least one modulators according to several aspects presented herein

| NAME | IUPAC name | mTorr Pvap | $\delta_D$ | MPa$^{1/2}$ $\delta_P$ | $\delta_H$ | (µg/l air) Volatility |
|---|---|---|---|---|---|---|
| ALCOHOL C 12 | dodecanol | 0.699 | 14.048 | 3.322 | 9.317 | 7.01 |
| SANDALORE | 3-Methyl-5-(2,2,3-trimethylcyclopent-3-en-1-yl)pentan-2-ol | 0.620 | 15.848 | 3.309 | 9.498 | 7.02 |
| METHYLISOEUGENOL | (E)-1,2-Dimethoxy-4-(prop-1-en-1-yl)benzene | 0.571 | 16.393 | 5.737 | 8.702 | 5.48 |
| EXALTONE | Cyclopentadecanone | 0.474 | 17.081 | 2.454 | 3.175 | 5.73 |
| NEROLIDOL | 3,7,11-trimethyl-1,6,10-dodecatrien-3-ol | 0.444 | 16.315 | 3.186 | 9.924 | 5.32 |
| MUGUET ALDEHYDE ARR | 6,10-Dimethyl-3-oxa-9-undecenal | 0.440 | 16.306 | 2.691 | 6.481 | 4.7 |
| CEDROXYDE ® | (4E,8E)-1,5,9-trimethyl-13-oxabicyclo[10.1.0]trideca-4,8-diene | 0.424 | 17.011 | 2.892 | 4.089 | 5.03 |
| JASMOLACTONE DELTA | 6-[(E)-pent-2-enyl]oxan-2-one | 0.379 | 16.754 | 7.251 | 5.856 | 3.43 |
| ROMANDOLIDE ® | Aceticacid,(1-oxopropoxy)-,1-(3,3-dimethylcyclohexyl)ethyl | 0.292 | 14.512 | 3.039 | 7.299 | 4.25 |
| NOOTKATONE PURE | 4-α,5-Dimethyl-1,2,3,4,4a,5,6,7-octahydro-7-keto-3-isopropenylnaphthalene | 0.270 | 16.968 | 5.566 | 6.773 | 3.18 |
| AMIONE | (+-)-(1E)-1-(2,6,6-trimethyl-2-cyclohexen-1-yl)-1,6-heptadien-3- | 0.241 | 16.387 | 3.301 | 5.542 | 3.01 |

TABLE 9-continued

Examples of some at least one modulators according to several aspects presented herein

| NAME | IUPAC name | mTorr Pvap | MPa$^{1/2}$ $\delta_D$ | $\delta_P$ | $\delta_H$ | (µg/l air) Volatility |
|---|---|---|---|---|---|---|
| | one (A); (1E)-1-(2,6,6-trimethyl-1-cyclohexen-1-yl)-1,6-heptadien-3-one (B) | | | | | |
| HEDIONE ® | Methyl 2-(3-oxo-2-pentylcyclopentyl)ethanoate | 0.218 | 16.852 | 3.759 | 5.510 | 2.66 |
| HEXYL SALICYLATE | hexyl 2-hydroxybenzoate | 0.216 | 17.926 | 7.413 | 10.160 | 2.58 |
| EXALTOLIDE ® | oxacyclohexadecan-2-one | 0.195 | 17.303 | 4.621 | 3.899 | 2.52 |
| MUSCONE | 3-methylcyclopentadecan-1-one | 0.140 | 16.712 | 2.286 | 3.132 | 1.8 |
| EXALTENONE | cyclopentadec-4-en-1-one | 0.139 | 16.725 | 2.511 | 4.094 | 1.67 |
| AMBRETTOLIDE | (8E)-1-oxacycloheptadec-8-en-2-one | 0.139 | 16.94 | 4.386 | 4.508 | 1.89 |
| PARADISONE ® | methyl 2-[(1R,2S)-3-oxo-2-pentylcyclopentyl]acetate | 0.134 | 16.852 | 3.759 | 5.510 | 1.63 |
| METHYL JASMONATE | methyl 2-[(1R,2R)-3-oxo-2-[(Z)-pent-2-enyl]cyclopentyl]acetate | 0.132 | 16.426 | 3.861 | 6.230 | 1.59 |
| GALAXOLIDE | 4,6,6,7,8,8-hexamethyl-1,3,4,7-tetrahydrocyclopenta[g]isochromene | 0.114 | 17.216 | 1.874 | 4.745 | 1.59 |
| DODECALACTONE DELTA | 6-heptyloxan-2-one | 0.084 | 17.22 | 5.957 | 4.485 | 0.896 |
| BENZYL BENZOATE | benzyl benzoate | 0.074 | 19.156 | 7.650 | 6.294 | 0.848 |
| AMYLCINNAMIC ALDEHYDE | (2E)-2-benzylideneheptanal | 0.063 | 17.98 | 2.409 | 5.690 | 0.682 |
| HEXYLCINNAMIC ALDEHYDE | (2E)-2-benzylideneoctanal | 0.061 | 17.937 | 2.230 | 5.475 | 0.708 |
| CIVETTONE | (9Z)-cycloheptadec-9-en-1-one | 0.031 | 16.713 | 2.209 | 3.844 | 0.424 |
| IPM | propan-2-yl tetradecanoate | 0.000 | 16.2 | 2.000 | 4.000 | 0 |

The at least one modulator is present in an amount from 0.1 to 20 wt %, relative to the total weight of the composition. Alternatively, the at least one modulator is present in an amount from 0.2 to 20 wt %, relative to the total weight of the composition. Alternatively, the at least one modulator is present in an amount from 0.3 to 20 wt %, relative to the total weight of the composition. Alternatively, the at least one modulator is present in an amount from 0.4 to 20 wt %, relative to the total weight of the composition. Alternatively, the at least one modulator is present in an amount from 0.5 to 20 wt %, relative to the total weight of the composition. Alternatively, the at least one modulator is present in an amount from 0.6 to 20 wt %, relative to the total weight of the composition. Alternatively, the at least one modulator is present in an amount from 0.7 to 20 wt %, relative to the total weight of the composition. Alternatively, the at least one modulator is present in an amount from 0.8 to 20 wt %, relative to the total weight of the composition. Alternatively, the at least one modulator is present in an amount from 0.9 to 20 wt %, relative to the total weight of the composition. Alternatively, the at least one modulator is present in an amount from 1 to 20 wt %, relative to the total weight of the composition. Alternatively, the at least one modulator is present in an amount from 0.1 to 20 wt %, relative to the total weight of the composition. Alternatively, the at least one modulator is present in an amount from 1.1 to 20 wt %, relative to the total weight of the composition. Alternatively, the at least one modulator is present in an amount from 1.2 to 20 wt %, relative to the total weight of the composition. Alternatively, the at least one modulator is present in an amount from 1.3 to 20 wt %, relative to the total weight of the composition. Alternatively, the at least one modulator is present in an amount from 1.4 to 20 wt %, relative to the total weight of the composition. Alternatively, the at least one modulator is present in an amount from 1.5 to 20 wt %, relative to the total weight of the composition. Alternatively, the at least one modulator is present in an amount from 1.6 to 20 wt %, relative to the total weight of the composition. Alternatively, the at least one modulator is present in an amount from 1.7 to 20 wt %, relative to the total weight of the composition. Alternatively, the at least one modulator is present in an amount from 1.8 to 20 wt %, relative to the total weight of the composition. Alternatively, the at least one modulator is present in an amount from 1.9 to 20 wt %, relative to the total weight of the composition. Alternatively, the at least one modulator is present in an amount from 2 to 20 wt %, relative to the total weight of the composition. Alternatively, the at least one modulator is present in an amount from 2.1 to 20 wt %, relative to the total weight of the composition. Alternatively, the at least one modulator is present in an amount from 2.2 to 20 wt %, relative to the total weight of the composition. Alternatively, the at least one modulator is present in an amount from 2.3 to 20 wt %, relative to the total weight of the composition. Alternatively, the at least one modulator is present in an amount from 2.4 to 20 wt %, relative to the total weight of the composition. Alternatively, the at least one modulator is present in an amount from 2.5 to 20 wt %, relative to the total weight of the composition. Alternatively, the at least one modulator is present in an amount from 2.6 to 20 wt %, relative to the total weight of the composition. Alternatively, the at least one modulator is present in an amount from 2.7 to 20 wt %, relative to the total weight of the composition. Alternatively, the at least one modulator is present in an amount from 2.8 to 20 wt %, relative to the total weight of the composition. Alternatively, the at least one modulator is present in an amount from 2.9 to 20 wt %, relative to the total weight of the composition. Alternatively, the at least one modulator is present in an amount from 3 to 20 wt %, relative to the total weight of the composition. Alternatively, the at least one modulator is present in an amount from 3.1 to 20 wt %, relative to the total weight of the composition. Alternatively, the at least one modulator is present in an amount from 3.2 to 20 wt %, relative to the total weight of the composition. Alternatively, the at least one modulator is present in an amount from 3.3 to 20 wt %, relative to the total weight of the composition. Alternatively, the at least one modulator is present in an amount from 3.4 to 20 wt %, relative to the total weight of the composition. Alternatively, the at least one modulator is present in an amount from 3.5 to 20 wt %, relative to the total weight of the composition. Alternatively, the at least one modulator is present in an amount from 3.6 to 20 wt %, relative to the total weight of the composition. Alternatively, the at least one modulator is present in an amount from 3.7 to 20 wt %, relative to the total weight of the composition. Alternatively, the at least one modulator is present in an amount from 3.8 to 20 wt %, relative to the total weight of the composition. Alternatively, the at least one modulator is present in an amount from 3.9 to 20 wt %, relative to the total weight of the composition. Alternatively, the at least one modulator is present in an amount from 4 to 20 wt %, relative to the total weight of the composition. Alternatively, the at least one modulator is present in an amount from 4.1 to 20 wt %, relative to the total weight of the composition. Alternatively, the at least one modulator is present in an amount from 4.2 to 20 wt %, relative to the total weight of the composition. Alternatively, the at least one modulator is present in an amount from 4.3 to 20 wt %, relative to the total weight of the composition. Alternatively, the at least one modulator is present in an amount from 4.4 to 20 wt %, relative to the total weight of the composition. Alternatively, the at least one modulator is present in an amount from 4.5 to 20 wt %, relative to the total weight of the composition. Alternatively, the at least one modulator is present in an amount from 4.6 to 20 wt %, relative to the total weight of the composition. Alternatively, the at least one modulator is present in an amount from 4.7 to 20 wt %, relative to the total weight of the composition. Alternatively, the at least one modulator is present in an amount from 4.8 to 20 wt %, relative to the total weight of the composition. Alternatively, the at least one modulator is present in an amount from 4.9 to 20 wt %, relative to the total weight of the composition. Alternatively, the at least one modulator is present in an amount from 5 to 20 wt %, relative to the total weight of the composition. Alternatively, the at least one modulator is present in an amount from 5.1 to 20 wt %, relative to the total weight of the composition. Alternatively, the at least one modulator is present in an amount from 5.2 to 20 wt %, relative to the total weight of the composition. Alternatively, the at least one modulator is present in an amount from 5.3 to 20 wt %, relative to the total weight of the composition. Alternatively, the at least one modulator is present in an amount from 5.4 to 20 wt %, relative to the total weight of the composition. Alternatively, the at least one modulator is present in an amount from 5.5 to 20 wt %, relative to the total weight of the composition. Alternatively, the at least one modulator is present in an amount from 5.6 to 20 wt %, relative to the total weight of the composition. Alternatively, the at least one modulator is present in an amount from 5.7 to 20 wt %, relative to the total weight of the composition. Alternatively, the at least one modulator is present in an amount from 5.8 to 20 wt %, relative to the total weight of the composition. Alternatively, the at least one modulator is present in an amount from 5.9 to 20 wt %, relative to the total weight of the composition. Alternatively, the at least one modulator is present in an amount from 6 to 20 wt %, relative to the total weight of the composition. Alternatively, the at least one modulator is present in an amount from 6.1 to 20 wt %, relative to the total weight of the composition. Alternatively, the at least one modulator is present in an amount from 6.2 to 20 wt %, relative to the total weight of the composition. Alternatively, the at least one modulator is present in an amount from 6.3 to 20 wt %, relative to the total weight of the composition. Alternatively, the at least one modulator is present in an amount from 6.4 to 20 wt %, relative to the total weight of the composition. Alternatively, the at least one modulator is present in an amount from 6.5 to 20 wt %, relative to the total weight of the composition. Alternatively, the at least one modulator is present in an amount from 6.6 to 20 wt %, relative to the total weight of the composition. Alternatively, the at least one modulator is present in an amount from 6.7 to 20 wt %, relative to the total weight of the composition. Alternatively, the at least one modulator is present in an amount from 6.8 to 20 wt %, relative to the total weight of the composition. Alternatively, the at least one modulator is present in an amount from 6.9 to 20 wt %, relative to the total weight of the composition. Alternatively, the at least one modulator is present in an amount from 7 to 20 wt %, relative to the total weight of the composition. Alternatively, the at least one modulator is present in an amount from 7.1 to 20 wt %, relative to the total weight of the composition. Alternatively, the at least one modulator is present in an amount from 7.2 to 20 wt %, relative to the total weight of the composition. Alternatively, the at least one modulator is present in an amount from 7.3 to 20 wt %, relative to the total weight of the composition. Alternatively, the at least one modulator is present in an amount from 7.4 to 20 wt %, relative to the total weight of the composition. Alternatively, the at least one modulator is present in an amount from 7.5 to 20 wt %, relative to the total weight of the composition. Alternatively, the at least one modulator is present in an amount from 7.6 to 20 wt %, relative to the total weight of the composition. Alternatively, the at least one modulator is present in an amount from 7.7 to 20 wt %, relative to the total weight of the composition. Alternatively, the at least one modulator is present in an amount from 7.8 to 20 wt %, relative to the total weight of the composition. Alternatively, the at least one modulator is present in an amount from 7.9 to 20 wt %, relative to the total weight of the composition. Alternatively, the at least one modulator is present in an amount from 8 to 20 wt %, relative to the total weight of the composition. Alternatively, the at least one modulator is present in an amount from 8.1 to 20 wt %, relative to the total weight of the composition. Alternatively, the at least one modulator is present in an amount from 8.2 to 20 wt %, relative to the total weight of the composition. Alternatively, the at least one modulator is present in an amount from 8.3 to 20 wt %, relative to the total weight of the composition. Alternatively, the at least one modulator is present in an amount from 8.4 to 20 wt %, relative to the total weight of the composition. Alternatively, the at least one modulator is present in an amount from 8.5 to 20 wt %, relative to the total weight of the composition. Alternatively, the at least one modulator is present in an amount from 8.6 to 20 wt %, relative to the total weight of the composition. Alternatively, the at least one modulator is present in an amount from 8.7 to 20 wt %, relative to the total weight of the composition. Alternatively, the at least one modulator is present in an amount from 8.8 to 20 wt %, relative to the total weight of the composition. Alternatively, the at least one modulator is present in an amount from 8.9 to 20 wt %, relative to the total weight of the composition. Alternatively, the at least one modulator is present in an amount from 9 to 20 wt %, relative to the total weight of the composition. Alternatively, the at least one modulator is present in an amount from 9.1 to 20 wt %, relative to the total weight of the composition. Alternatively, the at least one modulator is present in an amount from 9.2 to 20 wt %, relative to the total weight of the composition. Alternatively, the at least one modulator is present in an amount from 9.3 to 20 wt %, relative to the total weight of the composition. Alternatively, the at least one modulator is present in an amount from 9.4 to 20 wt %, relative to the total weight of the composition. Alternatively, the at least one modulator is present in an amount from 9.5 to 20 wt %, relative to the total weight of the composition. Alternatively, the at least one modulator is present in an amount from 9.6 to 20 wt %, relative to the total weight of the composition. Alternatively, the at least one modulator is present in an amount from 9.7 to 20 wt %, relative to the total weight of the composition. Alternatively, the at least one modulator is present in an amount from 9.8 to 20 wt %, relative to the total weight of the composition. Alternatively, the at least one modulator is present in an amount from 9.9 to 20 wt %, relative to the total weight of the composition. Alternatively, the at least one modulator is present in an amount from 10 to 20 wt %, relative to the total weight of the composition. Alternatively, the at least one modulator is present in an amount from 10 to 20 wt %, relative to the total weight of the composition. Alternatively, the at least one modulator is present in an amount from 11 to 20 wt %, relative to the total weight of the composition. Alternatively, the at least one modulator is present in an amount from 12 to 20 wt %, relative to the total weight of the composition. Alternatively, the at least one modulator is present in an amount from 13 to 20 wt %, relative to the total weight of the composition. Alternatively, the at least one modulator is present in an amount from 14 to 20 wt %, relative to the total weight of the composition. Alternatively, the at least one modulator is present in an amount from 15 to 20 wt %, relative to the total weight of the composition. Alternatively, the at least one modulator is present in an amount from 16 to 20 wt %, relative to the total weight of the composition. Alternatively, the at least one modulator is present in an amount from 17 to 20 wt %, relative to the total weight of the composition. Alternatively, the at least one modulator is present in an amount from 18 to 20 wt %, relative to the total weight of the composition. Alternatively, the at least one modulator is present in an amount from 19 to 20 wt %, relative to the total weight of the composition.

Alternatively, the at least one modulator is present in an amount from 0.1 to 19 wt %, relative to the total weight of the composition. Alternatively, the at least one modulator is present in an amount from 0.1 to 18 wt %, relative to the total weight of the composition. Alternatively, the at least one modulator is present in an amount from 0.1 to 17 wt %, relative to the total weight of the composition. Alternatively, the at least one modulator is present in an amount from 0.1 to 16 wt %, relative to the total weight of the composition. Alternatively, the at least one modulator is present in an amount from 0.1 to 15 wt %, relative to the total weight of the composition. Alternatively, the at least one modulator is present in an amount from 0.1 to 14 wt %, relative to the total weight of the composition. Alternatively, the at least one modulator is present in an amount from 0.1 to 13 wt %, relative to the total weight of the composition. Alternatively, the at least one modulator is present in an amount from 0.1 to 12 wt %, relative to the total weight of the composition. Alternatively, the at least one modulator is present in an amount from 0.1 to 11 wt %, relative to the total weight of the composition. Alternatively, the at least one modulator is present in an amount from 0.1 to 10 wt %, relative to the total weight of the composition. Alternatively, the at least one modulator is present in an amount from 0.1 to 9 wt %, relative to the total weight of the composition. Alternatively, the at least one modulator is present in an amount from 0.1 to 8 wt %, relative to the total weight of the composition. Alternatively, the at least one modulator is present in an amount from 0.1 to 7 wt %, relative to the total weight of the composition. Alternatively, the at least one modulator is present in an amount from 0.1 to 6 wt %, relative to the total weight of the composition. Alternatively, the at least one modulator is present in an amount from 0.1 to 5 wt %, relative to the total weight of the composition. Alternatively, the at least one modulator is present in an amount from 0.1 to 4 wt %, relative to the total weight of the composition. Alternatively, the at least one modulator is present in an amount from 0.1 to 3 wt %, relative to the total weight of the composition. Alternatively, the at least one modulator is present in an amount from 0.1 to 2 wt %, relative to the total weight of the composition. Alternatively, the at least one modulator is present in an amount from 0.1 to 1 wt %, relative to the total weight of the composition. Alternatively, the at least one modulator is present in an amount from 0.1 to 0.9 wt %, relative to the total weight of the composition. Alternatively, the at least one modulator is present in an amount from 0.1 to 0.8 wt %, relative to the total weight of the composition. Alternatively, the at least one modulator is present in an amount from 0.1 to 0.7 wt %, relative to the total weight of the composition. Alternatively, the at least one modulator is present in an amount from 0.1 to 0.6 wt %, relative to the total weight of the composition. Alternatively, the at least one modulator is present in an amount from 0.1 to 0.5 wt %, relative to the total weight of the composition. Alternatively, the at least one modulator is present in an amount from 0.1 to 0.4 wt %, relative to the total weight of the composition. Alternatively, the at least one modulator is present in an amount from 0.1 to 0.3 wt %, relative to the total weight of the composition. Alternatively, the at least one modulator is present in an amount from 0.1 to 0.2 wt %, relative to the total weight of the composition.

In some aspects, the at least one modulator is present at 0.1, or 0.2, or 0.3, or 0.4, or 0.5, or 0.6, or 0.7, or 0.8, or 0.9, or 1, or 1.1, or 1.2, or 1.3, or 1.4, or 1.5, or 1.6, or 1.7, or 1.8, or 1.9, or 2, or 2.1, or 2.2, or 2.3, or 2.4, or 2.5, or 2.6, or 2.7, or 2.8, or 2.9, or 3, or 3.1, or 3.2, or 3.3, or 3.4, or 3.5, or 3.6, or 3.7, or 3.8, or 3.9, or 4, or 4.1, or 4.2, or 4.3, or 4.4, or 4.5, or 4.6, or 4.7, or 4.8, or 4.9, or 5, or 5.1, or 5.2, or 5.3, or 5.4, or 5.5, or 5.6, or 5.7, or 5.8, or 5.9, or 6, or 6.1, or 6.2, or 6.3, or 6.4, or 6.5, or 6.6, or 6.7, or 6.8, or 6.9, or 7, 7.1, or 7.2, or 7.3, or 7.4, or 7.5, or 7.6, or 7.7, or 7.8, or 7.9, or 8, or 8.1, or 8.2, or 8.3, or 8.4, or 8.5, or 8.6, or 8.7, or 8.8, or 8.9, or 9, or 9.1, or 9.2, or 9.3, or 9.4, or 9.5, or 9.6, or 9.7, or 9.8, or 9.9, or 10, or 10.1, or 10.2, or 10.3, or 10.4, or 10.5, or 10.6, or 10.7, or 10.8, or 10.9, or 11, or 11.1, or 11.2, or 11.3, or 11.4, or 11.5, or 11.6, or 11.7, or 11.8, or 11.9, or 12, or 12.1, or 12.2, or 12.3, or 12.4, or 12.5, or 12.6, or 12.7, or 12.8, or 12.9, or 13, or 13.1, or 13.2, or 13.3, or 13.4, or 13.5, or 13.6, or 13.7, or 13.8, or 13.9, or 14, or 14.1, or 14.2, or 14.3, or 14.4, or 14.5, or 14.6, or 14.7, or 14.8, or 14.9, or 15, or 15.1, or 15.2, or 15.3, or 15.4, or 15.5, or 15.6, or 15.7, or 15.8, or 15.9, or 16, or 16.1, or 16.2, or 16.3, or 16.4, or 16.5, or 16.6, or 16.7, or 16.8, or 16.9, or 17, or 17.1, or 17.2, or 17.3, or 17.4, or 17.5, or 17.6, or 17.7, or 17.8, or 17.9, or 18, 18.1, or 18.2, or 18.3, or 18.4, or 18.5, or 18.6, or 18.7, or 18.8, or 18.9, or 19, or 19.1, or 19.2, or 19.3, or 19.4, or 19.5, or 19.6, or 19.7, or 19.8, or 19.9, or 20, or 20.1, or 20.2, or 20.3, or 20.4, or 20.5, or 20.6, or 20.7, or 20.8, or 20.9, or 21, or 21.1, or 21.2, or 21.3, or 21.4, or 21.5, or 21.6, or 21.7, or 21.8, or 21.9, or 22, or 22.1, or 22.2, or 22.3, or 22.4, or 22.5, or 22.6, or 22.7, or 22.8, or 22.9, or 23, or 23.1, or 23.2, or 23.3, or 23.4, or 23.5, or 23.6, or 23.7, or 23.8, or 23.9, or 24, or 24.1, or 24.2, or 24.3, or 24.4, or 24.5, or 24.6, or 24.7, or 24.8, or 24.9, or 25, or 25.1, or 25.2, or 25.3, or 25.4, or 25.5, or 25.6, or 25.7, or 25.8, or 25.9, or 26, or 26.1, or 26.2, or 26.3, or 26.4, or 26.5, or 26.6, or 26.7, or 26.8, or 26.9, or 27, or 27.1, or 27.2, or 27.3, or 27.4, or 27.5, or 27.6, or 27.7, or 27.8, or 27.9, or 28, 28.1, or 28.2, or 28.3, or 28.4, or 28.5, or 28.6, or 28.7, or 28.8, or 28.9, or 29, or 29.1, or 29.2, or 29.3, or 29.4, or 29.5, or 29.6, or 29.7, or 29.8, or 29.9, or 30, or 30.1, or 30.2, or 30.3, or 30.4, or 30.5, or 30.6, or 30.7, or 30.8, or 30.9, or 31, or 31.1, or 31.2, or 31.3, or 31.4, or 31.5, or 31.6, or 31.7, or 31.8, or 31.9, or 32, or 32.1, or 32.2, or 32.3, or 32.4, or 32.5, or 32.6, or 32.7, or 32.8, or 32.9, or 33, or 33.1, or 33.2, or 33.3, or 33.4, or 33.5, or 33.6, or 33.7, or 33.8, or 33.9, or 34, or 34.1, or 34.2, or 34.3, or 34.4, or 34.5, or 34.6, or 34.7, or 34.8, or 34.9, or 35, or 35.1, or 35.2, or 35.3, or 35.4, or 35.5, or 35.6, or 35.7, or 35.8, or 35.9, or 36, or 36.1, or 36.2, or 36.3, or 36.4, or 36.5, or 36.6, or 36.7, or 36.8, or 36.9, or 37, or 37.1, or 37.2, or 37.3, or 37.4, or 37.5, or 37.6, or 37.7, or 37.8, or 37.9, or 38, 38.1, or 38.2, or 38.3, or 38.4, or 38.5, or 38.6, or 38.7, or 38.8, or 38.9, or 39, or 39.1, or 39.2, or 39.3, or 39.4, or 39.5, or 39.6, or 39.7, or 39.8, or 39.9, or 40, or 40.1, or 40.2, or 40.3, or 40.4, or 40.5, or 40.6, or 40.7, or 40.8, or 40.9, or 41, or 41.1, or 41.2, or 41.3, or 41.4, or 41.5, or 41.6, or 41.7, or 41.8, or 41.9, or 42, or 42.1, or 42.2, or 42.3, or 42.4, or 42.5, or 42.6, or 42.7, or 42.8, or 42.9, or 43, or 43.1, or 43.2, or 43.3, or 43.4, or 43.5, or 43.6, or 43.7, or 43.8, or 43.9, or 44, or 44.1, or 44.2, or 44.3, or 44.4, or 44.5, or 44.6, or 44.7, or 44.8, or 44.9, or 45, or 45.1, or 45.2, or 45.3, or 45.4, or 45.5, or 45.6, or 45.7, or 45.8, or 45.9, or 46, or 46.1, or 46.2, or 46.3, or 46.4, or 46.5, or 46.6, or 46.7, or 46.8, or 46.9, or 47, or 47.1, or 47.2, or 47.3, or 47.4, or 47.5, or 47.6, or 47.7, or 47.8, or 47.9, or 48, 48.1, or 48.2, or 48.3, or 48.4, or 48.5, or 48.6, or 48.7, or 48.8, or 48.9, or 49, or 49.1, or 49.2, or 49.3, or 49.4, or 49.5, or 49.6, or 49.7, or 49.8, or 49.9, or 50 wt %, relative to the total weight of the composition.

In some aspects, the concentration of the at least one modulator is 15 wt %, relative to the total weight of the composition.

In one aspect, the at least one modulator is a liquid at temperatures lower than 100° C. In one aspect, the modulator is liquid at ambient temperature. In some aspects, the at least one modulator fully miscible with the perfume raw materials added to the composition according to some aspects presented herein, thereby forming a single phase liquid. However, if the perfume raw materials are not entirely miscible, or are immiscible, then co-solvents (such as, for example, dipropylene glycol (DPG), triethyl citrate, or others as well known to those skilled in the art) may be added to aid in the solubility of the perfume raw materials in the at least one modulator.

The compositions presented herein may further comprise additional components, such as, for example, polymers; capsules, microcapsules and nanocapsules; liposomes, absorbents; cyclic oligosaccharides and mixtures thereof. Examples of suitable additional components are described in International Patent Application Publication No. WO 2015/089246 A1. In some embodiments, the additional components comprise cyclodextrin. In some embodiments, the cyclodextrin further contains at least one compound having a c Log P value from 1.5 to 3.5. In some aspects, the c Log P value is from 2 to 3.

In some aspects, the at least one compound has an odor value from 1 to 10,000.

In some aspects, the at least one compound within the capsules has a $C_{T2.5}$ from 0.1 and 10 μg/l.

TABLE 10

Examples of at least one compound having a cLogP value from 1.5 to 3.5 according to several aspects presented herein

| COMMON NAME | IUPAC NAME |
|---|---|
| 2 E-HEXENYL ACETATE | HEXYL ACETATE |
| BIONAT K | |
| 2-NAPHTHALENETHIOL | naphthalene-2-thiol |
| 2-NONANONE NAT | 2-NONANONE |
| 4-ETHYL OCTANOIC ACID | (+−)-4-ethyloctanoic acid |
| ALADINATE ® | (2E)-3-methyl-2-hexen-1-yl acetate |
| ALCOHOL C 6 K NAT | 1-hexanol |
| ALCOHOL C 6 K NAT PF | 1-hexanol |
| ALCOHOL C 6 PURIF | 1-hexanol |
| ALCOHOL C 8 REDIST | 1-octanol |
| ALDEHYDE C 6 FC | hexanal |
| ALDEHYDE C 7 | heptanal |
| ALDEHYDE C 8 | octanal |
| ALDEHYDE C 9 | nonanal |
| ALDOLONE ® | 7-PROPYL-2H,4H-1,5-BENZODIOXEPIN-3-ONE |
| ALLYL AMYL GLYCOLATE | (+−)-ALLYL (2-METHYLBUTOXY) ACETATE |
| ALLYL PHENOXYACETATE | ALLYL PHENOXYACETATE |
| AMBRINOL OXIDE | (+−)-4A,8A-EPOXY-PERHYDRO-2.5.5-TRIMETHYL-2-NAPHTHALENOL |
| AMYL ACETATE | 3-METHYLBUTYL ACETATE |
| AMYL ISOBUTYRATE | 3-methylbutyl 2-methylpropanoate |
| AMYL PROPIONATE | (+−)-2-METHYLBUTYL PROPANOATE |
| ANISYL ACETATE | 4-METHOXYBENZYL ACETATE |
| ANISYL ACETONE | 4-(4-methoxyphenyl)butan-2-one |
| APPLINATE | ethyl 2-methylpentanoate |
| AQUOZONE | 3-(butylamino)-4-phenoxy-5-sulfamoylbenzoic acid |
| AROMATONE | (1RS,2SR,5SR,7RS,8SR)-5-methyltricyclo[6.2.1.0~2,7~]undecan-4-one |
| ASMAROL | (+−)-1-HEXYL-1,3-PROPANEDIYL DIACETATE |
| BENZOPHENONE | BENZOPHENONE |
| BENZYL ACETATE | benzyl acetate |
| BENZYL ISOBUTYRATE | BENZYL ISOBUTYRATE |
| BENZYL PROPIONATE | BENZYL PROPANOATE |
| BENZYL TIGLATE | BENZYL (E)-2-METHYL-2-BUTENOATE |
| BENZYL VALERIANATE | BENZYL 3-METHYLBUTANOATE |
| BENZYLDIMETHYLCARBINOL ACETATE | 1,1-DIMETHYL-2-PHENYLETHYL ACETATE |
| BORNEOL CRYST | (+)-(1S,2S,4S)-1,7,7-trimethylbicyclo[2.2.1]heptan-2-ol |
| BOURGEONAL | 3-(4-TERT-BUTYLPHENYL) PROPANAL |
| ISOPROPYL METHYLBUTYRATE | (+−)-ISOPROPYL 2-METHYLBUTANOATE |
| ISOPROPYL QUINOLINE | 8-isopropylquinoline |
| ISOPULEGOL | (1R,2S,5R)-5-methyl-2-prop-1-en-2-ylcyclohexan-1-ol |
| JASMAL | (3RS,4SR)-3-pentyltetrahydro-2H-pyran-4-yl acetate TETRAHYDRO-3-PENTYL-4(2H)-PYRANYL ACETATE |
| JASMOLACTONE DELTA | (+−)-(Z)-8-DECEN-5-OLIDE |
| JOSENOL ® | (2E)-2-METHYL-3-(4-METHYLPHENYL)-2-PROPEN-1-OL |
| KOUMALACTONE ® | (3SR,3ARS,6SR,7ASR)-PERHYDRO-3,6-DIMETHYL-BENZO[B]FURAN-2-ONE |

TABLE 10-continued

Examples of at least one compound having a cLogP value from 1.5 to 3.5 according to several aspects presented herein

| COMMON NAME | IUPAC NAME |
|---|---|
| LEMONILE | 3.7-DIMETHYL-2.6-NONADIENENITRILE |
| LEVOCITROL | (+−)-3,7-DIMETHYL-6-OCTEN-1-OL |
| LIFFAROME | (3Z)-hex-3-en-1-yl methyl carbonate |
| LILYFLORE ® | (+−)-2,5-DIMETHYL-2-INDANMETHANOL |
| LIME OXIDE | 1,3,3-trimethyl]-2-oxabicyclo[2.2.2]octane |
| LINALOL BJ | (+−)-3,7-dimethyl-1,6-octadien-3-ol |
| LYRAL | (+−)-4-(4-hydroxy-4-methylpentyl)-3-cyclohexene-1-carbaldehyde |
| MAGNOLAN | (+−)-2,4-dimethyl-4,4a,5,9b-tetrahydroindeno[1,2-d[1,3]dioxine (ISOMER A) |
| MAYOL ® | trans-4-(2-propanyl)cyclohexyl]methanol |
| MELONAL | 2,6-Dimethyl-5-heptenal |
| MENTHOL | (−)-L-MENTHOL |
| MENTHONE PURIFIED | (2RS,5SR)-5-methyl-2-(2-propanyl)cyclohexanone |
| METHYL ANISATE | METHYL 4-METHOXYBENZOATE |
| METHYL BENZOATE | METHYL BENZOATE |
| METHYL BENZOATE NAT FIRINC | METHYL BENZOATE |
| METHYL CAPROATE | METHYL HEXANOATE |
| METHYL CINNAMATE | methyl (E)-3-phenylprop-2-enoate |
| METHYL CRESOTINATE | METHYL 2-HYDROXY-5-METHYLBENZOATE |
| METHYL CYCLOGERANATE | 2-cyclohexene-1-carboxylic acid 2,6,6,-trimethyl methyl ester |
| METHYL DISULFIDE MF | METHYL 2-METHYL-3-FURYL DISULFIDE |
| METHYL HEPTINECARBONATE | METHYL 2-OCTYNOATE |
| METHYL JASMONATE | methyl {(1RS,2RS)-3-oxo-2-[(2Z)-2-penten-1-yl]cyclopentyl}acetate |
| METHYL METHYLANTHRANILATE | methyl 2-(rnethylamino)benzoate |
| METHYL SALICYLATE | METHYL 2-HYDROXYBENZOATE |
| METHYLCINNAMIC ALDEHYDE | (2E)-2-methyl-3-phenyl-2-propenal |
| METHYLHEPTYLKETONE | nonan-2-one |
| METHYLHEXYLKETONE | 2-OCTANONE |
| METHYLISOEUGENOL | 1,2-dimethoxy-4-[(1E)-1-propen-1-yl]benzene |

The compositions presented herein may be formulated in any suitable solvent. Examples of suitable solvents include, but are not limited to ethanol or other alcohols (e.g., methanol, propanol, isopropanol, butanol, and mixtures thereof) commonly found in commercial fine fragrance products. Accordingly, ethanol may be present in any of the compositions of the present disclosure, and more specifically, it will form from about 10 wt to about 80 wt %, or even from about 25 wt to about 75 wt % of the composition, or combinations thereof, relative to the total weight of the composition. Alternatively, ethanol may be present in an amount of from about 10 wt or 25 wt to about 75 wt or 80 wt %, relative to the total weight of the composition. Any acceptable quality of ethanol, compatible and safe for the specific intended use of the composition such as, for example, topical applications of fine fragrance or cosmetic compositions, and is convenient for use in the compositions according to the present invention.

The compositions presented herein may comprise a non-volatile solvent or a mixture of non-volatile solvents. Non-limiting examples of non-volatile solvents include benzyl benzoate, diethyl phthalate, isopropyl myristate, propylene glycol, dipropylene glycol, triethyl citrate, and mixtures thereof. These solvents often are introduced to the product via the perfume oil as many perfume raw materials may be purchased as a dilution in one of these solvents. Where non-volatile solvents are present, introduced either with the perfume materials or separately, then for the purposes of calculating the vapor pressure, the total fragrance components does not include non-volatile solvents.

In some aspects, the composition further comprises at least one hydrophilic solvent. In one aspect, the at least one hydrophilic solvent is selected from the group consisting of: propylene glycol, dipropylene glycol, ethylene glycol, triethyl citrate, disisopropyl glycol monomethyl ether, diethylene glycol monoethyl ether; triacetin, methylmethoxybutanol, benzyl alcohol, propylene glycol n-butyl ether; a glycol ether, an ester of diethylene glycol, and a cellosolve derivative. In one aspect, the glycol ether is a glycol ether sold under the tradename DOWANOL. In one aspect, the ether of diethylene glycol is sold under the tradename CARBITOL.

In some aspects, the glycol ether sold under the tradename DOWANOL is selected from the group consisting of: DOWANOL™ DPMA Glycol Ether; DOWANOL™ PM Glycol Ether; DOWANOL EPH ELP; DOWANOL™ EPh; DOWANOL™ PnB Glycol Ether; DOWANOL™ TPnB; DOWANOL™ DPnB Glycol Ether; DOWANOL™ TPM Glycol Ether; DOWANOL™ PPh Glycol Ether; DOWANOL™ PnP Glycol Ether; DOWANOL™ DPH 255 Glycol Ether; DOWANOL™ PGDA Glycol Ether; DOWANOL™ DPM Glycol Ether; DOWANOL™ TPnB-H Gly Ether; DOWANOL™ Solvents for Home & Personal Care; DOWANOL™ DPnP Glycol Ether; DOWANOL™ PMA Glycol Ether; DOWANOL™ DiPPh Glycol Ether.

In some aspects, the cellosolve derivative is selected from the group consisting of: propyl cellosolve, butyl cellosolve, hexyl cellosolve, and cellosolve.

Products and Formulations According to Some Aspects Presented Herein:

One aspect presented herein, provides a perfuming consumer product comprising the composition according to an aspect presented herein.

One aspect presented herein provides a perfuming composition comprising the composition according to an aspect presented herein.

One aspect presented herein, provides a perfuming consumer product comprising the perfuming composition according to an aspect presented herein.

In one aspect, the perfuming consumer product is selected from the group consisting of a perfume, eau de toilette, home care product and a personal care product.

In some aspects, the perfumed consumer product is selected from the group consisting of: air care products, home care products and laundry care products.

It is understood by a person skilled in the art that the composition as defined herein, may be added into the perfuming composition, or the perfuming consumer product in neat form, or in a solvent. Alternatively, the composition may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof.

Accordingly, some aspects presented herein provide a perfuming composition, or a perfuming consumer product comprising:
a. the composition according to an aspect presented herein;
b. at least one ingredient selected from the group consisting of a perfumery carrier and a perfumery base; and
c. optionally at least one perfumery adjuvant.

In some aspects, the perfumed consumer product comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

As used herein, the term "perfumery carrier" refers to a material which is practically neutral from a perfumery point of view, i.e. which does not significantly alter the organoleptic properties of perfuming ingredients. The perfumery carrier may be a liquid or a solid.

Non-limiting examples of liquid perfumery carriers include an emulsifying system, i.e. a solvent and a surfactant system, or a solvent commonly used in perfumery. A detailed description of the nature and type of solvents commonly used in perfumery cannot be exhaustive. However, non-limiting examples solvents include dipropyleneglycol, diethyl phthalate, isopropyl myristate, benzyl benzoate, 2-(2-ethoxyethoxy)-1-ethanol or ethyl citrate. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Non-limiting examples of solid perfumery carriers include absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

As used herein, the term "perfumery base" refers a composition comprising at least one perfuming co-ingredient. As used herein, the term "perfuming co-ingredient" refers to compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

As used herein, the term "perfumery adjuvant" refers to an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

The proportions in which the composition can be incorporated into the various aforementioned products or compositions vary within a wide range of values. These values are dependent on the nature of the consumer product and on the desired organoleptic effect as well as the nature of the co-ingredients in a given formulation when the composition according to an aspect presented herein is mixed with other ingredients, solvents or additives commonly used in the art.

In general, for example, in the case of perfuming compositions, typical concentrations are in the order of 0.001% to 5% by weight, or even more, of the composition according to an aspect presented herein, based on the weight of the formulation into which they are incorporated. Concentrations lower than these, such as in the order of 0.01% to 100% by weight, can be used when the compositions described herein are incorporated into consumer products, the percentage being relative to the weight of the consumer product.

The compositions described herein may include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1, 2,3, 3,3-heptafluoropropane, trans-1,3,3, 3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42% by weight of the total fill of materials stored within the container.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

Non-limiting examples of suitable perfuming consumer product include:

- a perfume, such as a fine perfume, an Eau de Toilette, a cologne or an after-shave lotion;
- a fabric care product, such as a liquid detergent, a powder detergent, detergent tablets, a detergent bar, a detergent paste, a detergent pouch, a liquid fabric softener, fabric softener sheets, a fabric scent booster, a laundry pre-treatment, a fabric refresher, an ironing water, a laundry bleach, a carpet powder or a carpet cleaner;
- a hair care product, such as a shampoo, a hair conditioner, a hair cream, a hair oil, a hair styling product (such as a spray, mousse or gel), a hair coloration product or a hair permanent wave product;
- a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;
- a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;
- a skin-cleansing product, such as a soap bar, a shower gel, a liquid hand soap, a bath foam or an intimate wash product;
- an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or
- a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid; a pet-litter.

In some aspects, the perfumed consumer product comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

In some aspects, the composition as defined in any of the above aspect may be absorbed on a porous or non-porous substrate in loose powder or compacted form, the substrate being selected from cellulose (paper/cardboard), vermiculite, other industrial absorbents, perlite, calcium carbonate, pumice, wood, sawdust, ground corn cob, ground rice hull, rice hull ash, biochars, starches, modified starches and mixtures thereof.

In some aspects, the consumer product is selected from the group consisting of: a fine perfume, a splash or eau de perfume, a cologne, an shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, and a car care product.

The compositions described herein are a useful perfuming composition, which can be advantageously used as consumer products intended to perfume any suitable substrate. As used herein, the term "substrate" means any surface to which the composition of the present invention may be applied to without causing any undue adverse effect. For example, this can include a wide range of surfaces including human or animal skin or hair, paper (fragranced paper), air in a room (air freshener or aromatherapy composition), fabric, furnishings, dishes, hard surfaces and related materials.

The compositions described herein may be used in a conventional manner for fragrancing a substrate. An effective amount of the composition, typically from about 1 µL· to about 10,000 µL, alternatively from about 10 µL to about 1,000 µL, alternatively from about 25 µL· to about 500 µL, alternatively from about 50 µL to about 100 µL, or combinations thereof, is applied to the suitable substrate.

Alternatively, an effective amount of the composition presented herein is from about 1 µL, 10 µL, 25 µL or 50 µL to about 100 µL, 500 µL, 1,000 µL or 10,000 µL. The composition may be applied by hand or applied utilizing a delivery apparatus such as, for example, vaporizer or atomizer. In one aspect, the composition is allowed to dry after its application to the substrate. The scope of the present disclosure should be considered to cover one or more distinct applications of the composition or the continuous release of a composition via a vaporizer or other type of atomizer. In one aspect, the composition relates to fine fragrance compositions in the form of a perfume, an eau de toilette, an eau de parfum, a cologne, a body splash, or a body spray. Therefore, according to these aspects, the present invention provides a method for modifying or enhancing the odor properties of a body surface, preferably hair or skin, comprising contacting or treating the body surface with a composition according to the aspects presented herein.

In another aspect, the present disclosure relates to compositions of the present invention that may be used as consumer products or articles selected from the group consisting of a fabric care product, an air care product, or a home care product. Therefore, according to these aspects, the present invention provides a method for modifying or enhancing the odor properties of a substrate, such as fabric, furnishings, dishes, hard surfaces and related materials, comprising contacting or treating the substrate with a composition according to the aspects presented herein.

In another aspect, the present disclosure is directed to a method of enhancing the fragrance profile of a composition, by improving the longevity of an aroma of the composition. In one aspect, the method comprises bringing into contact or mixing the modulator with the fragrance component.

In one aspect, the fragrance profile or aroma of the composition is detectable by a consumer at later time points such as, for example, 2 hours, 4 hours, 6 hours, 8 hours, 10 hours, and possibly all the way up to 24 hours after application of the composition to a substrate as compared to controls.

The present invention is best illustrated but is not limited to the following examples.

EXAMPLES

Example 1: The Effect of Modulators According to Some Aspects Presented Herein on the Second Vapor Pressure of Selected Perfume Raw Materials, Wherein the Modulator Comprises PPG-20 Methyl Glucose Ether and Isocetyl Alcohol The first vapor pressure for the perfume raw materials indicated in Tables 11 to 15 was determined using standard methods at 22° C. The perfume raw materials were then added to the following modulators, wherein the final concentration of the modulator was 15 wt %, relative to the total weight of the composition:
1. PPG-20 methyl glucose ether and isocetyl alcohol (1:2 ratio);
2. PPG-20 methyl glucose ether and isocetyl alcohol (1.5:1.5 ratio);
3. PPG-20 methyl glucose ether and isocetyl alcohol (2:1); or
4. PPG-20 methyl glucose ether only The second vapor pressure for the selected perfume raw materials was then determined, and the perfume raw materials were classified as follows:

Whether, in the presence of the modulator, the selected perfume raw material either:
  i. remains available for selection for use in the high volatility component, wherein the second vapor pressure of the perfume raw material is greater than 0.08 Torr at 22° C.;
  ii. no longer remains available for selection for use in the high volatility component, but becomes available for selection for use in the medium volatility component, wherein the second vapor pressure of the perfume raw material has a range of 0.0008 to 0.08 Torr at 22° C.;
  iii. remains available for selection for use in the medium volatility component, wherein the second vapor pressure of the perfume raw has a range of 0.0008 to 0.08 Torr at 22° C.;
  iv. no longer remains available for selection for use in the medium volatility component, but becomes available for selection for use in the low volatility component, wherein the second vapor pressure of the perfume raw material is less than 0.0008 Torr at 22° C.; or
  v. remains available for selection for use in the low volatility component, wherein the second vapor pressure of the perfume raw is less than 0.0008 Torr at 22° C.

The results are shown in the tables below.

TABLE 11

Examples of perfume raw materials that remain available for selection for use in the high volatility component, wherein the second vapor pressure of the perfume raw material is greater than greater than 0.08 Torr at 22° C.

Modulator (15 wt %, relative to the total weight of the composition)

| PPG-20 methyl glucose ether and isocetyl alcohol (1:2) | PPG-20 methyl glucose ether and isocetyl alcohol (1.5:1.5) | PPG-20 methyl glucose ether and isocetyl alcohol (2:1) | PPG-20 methyl glucose ether |
|---|---|---|---|
| | | zestover* methyl pamplemousse | methyl pamplemousse |

*Denotes a high impact perfume raw material that remains a high impact perfume raw material in the presence of the modulator

TABLE 12

Examples of perfume raw materials that no longer remain available for selection for use in the high volatility component, but become available for selection for use in the medium volatility component, wherein the second vapor pressure of the perfume raw material has a range of 0.0008 to 0.08 Torr at 22° C.

Modulator (15 wt %, relative to the total weight of the composition)

| PPG-20 methyl glucose ether and isocetyl alcohol (1:2) | PPG-20 methyl glucose ether and isocetyl alcohol (1.5:1.5) | PPG-20 methyl glucose ether and isocetyl alcohol (2:1) | PPG-20 methyl glucose ether |
|---|---|---|---|
| zestover* methyl pamplemousse | zestover* methyl pamplemousse | zestover* | |

*Denotes a high impact perfume raw material that remains a high impact perfume raw material in the presence of the modulator

TABLE 13

Examples of perfume raw materials remain available for selection for use in the medium volatility component, wherein the second vapor pressure of the perfume raw has a range of 0.0008 to 0.08 Torr at 22° C.

Modulator (15 wt %, relative to the total weight of the composition)

| PPG-20 methyl glucose ether and isocetyl alcohol (1:2) | PPG-20 methyl glucose ether and isocetyl alcohol (1.5:1.5) | PPG-20 methyl glucose ether and isocetyl alcohol (2:1) | PPG-20 methyl glucose ether |
|---|---|---|---|
| citral§ Aldehyde C12* citronellol* | citral§ Aldehyde C12* citronellol* | citral* Aldehyde C12* citronellol* foliaver | citral* Aldehyde C12* citronellol* geraniol foliaver |
| decalactone* heliopropanal* | decalactone* | decalactone* javanol | decalactone* javanol |
| | | javanol | |

§Denotes a high impact perfume raw material that became a low impact perfume raw material in the presence of the modulator
*Denotes a high impact perfume raw material that remains a high impact perfume raw material in the presence of the modulator

TABLE 14

Examples of perfume raw materials that no longer remain available for selection for use in the medium volatility component, but become available for selection for use in the low volatility component, wherein the second vapor pressure of the perfume raw material is less than 0.0008 Torr at 22° C.
Modulator (15 wt %, relative to the total weight of the composition)

| PPG-20 methyl glucose ether and isocetyl alcohol (1:2) | PPG-20 methyl glucose ether and isocetyl alcohol (1.5:1.5) | PPG-20 methyl glucose ether and isocetyl alcohol (2:1) | PPG-20 methyl glucose ether |
|---|---|---|---|
| geraniol | geraniol | geraniol[+] | |
| nerol | nerol | nerol[+] | nerol |
| foliaver | foliaver | | |
| lilial | lilial | lilial | lilial* |
| | heliopropanal* | heliopropanal[+] | heliopropanal* |
| calone* | calone* | calone* | calone* |

*Denotes a high impact perfume raw material that remains a high impact perfume raw material in the presence of the modulator
[+]Denotes a perfume raw material that becomes suppressed in the presence of the modulator

TABLE 15

Examples of perfume raw materials that remain available for selection for use in the low volatility component, wherein the second vapor pressure of the perfume raw is less than 0.0008 Torr at 22° C.
Modulator (15 wt %, relative to the total weight of the composition)

| PPG-20 methyl glucose ether and isocetyl alcohol (1:2) | PPG-20 methyl glucose ether and isocetyl alcohol (1.5:1.5) | PPG-20 methyl glucose ether and isocetyl alcohol (2:1) | PPG-20 methyl glucose ether |
|---|---|---|---|
| hedione | hedione | hedione | hedione |
| bacdanol* | bacdanol* | bacdanol[+] | bacdanol* |
| | | astrotone[+] | astrotone[+] |

*Denotes a high impact perfume raw material that remains a high impact perfume raw material in the presence of the modulator
[+]Denotes a perfume raw material that becomes suppressed in the presence of the modulator Example 2: The Effect of Modulators According to Some Aspects Presented Herein on the Second Vapor Pressure of Selected Perfume Raw Materials, Wherein the Modulator Comprises PPG-20 Methyl Glucose Ether and Various Long Chain Alcohols The first vapor pressure for the perfume raw materials indicated in Tables 16 to 20 below was determined using standard methods at 22° C. The perfume raw materials were then added to the following modulators, wherein the final concentration of the modulator was 15 wt %, relative to the total weight of the composition:
1. PPG-20 methyl glucose ether and octyldodecanol (2:1 ratio);
2. PPG-20 methyl glucose ether and isostearyl alcohol (2:1 ratio);
3. PPG-20 methyl glucose ether and isocetyl alcohol (2:1 ratio); or
4. 10% wt % PPG-20 methyl glucose ether only (calculated)

The second vapor pressure for the selected perfume raw materials was then determined, and the perfume raw materials were classified as follows:
Whether, in the presence of the modulator, the selected perfume raw material either:
i. remains available for selection for use in the high volatility component, wherein the second vapor pressure of the perfume raw material is greater than 0.08 Torr at 22° C.;
ii. no longer remains available for selection for use in the high volatility component, but becomes available for selection for use in the medium volatility component, wherein the second vapor pressure of the perfume raw material has a range of 0.0008 to 0.08 Torr at 22° C.;
iii. remains available for selection for use in the medium volatility component, wherein the second vapor pressure of the perfume raw has a range of 0.0008 to 0.08 Torr at 22° C.;
iv. no longer remains available for selection for use in the medium volatility component, but becomes available for selection for use in the low volatility component, wherein the second vapor pressure of the perfume raw material is less than 0.0008 Torr at 22° C.; or
v. remains available for selection for use in the low volatility component, wherein the second vapor pressure of the perfume raw is less than 0.0008 Torr at 22° C.

The results are shown in the tables below.

TABLE 16

Examples of perfume raw materials that remain available for selection for use in the high volatility component, wherein the second vapor pressure of the perfume raw material is greater than greater than 0.08 Torr at 22° C.
Modulator (15 wt %, relative to the total weight of the composition)

| PPG-20 methyl glucose ether and octyldodecanol (2:1) | PPG-20 methyl glucose ether and isostearyl alcohol (2:1) | PPG-20 methyl glucose ether and isocetyl alcohol (2:1) | PPG-20 methyl glucose ether and vehicle |
|---|---|---|---|
| zestover* | zestover* | | zestover* |
| methyl pamplemousse | methyl pamplemousse | methyl pamplemousse | methyl pamplemousse |

*Denotes a high impact perfume raw material that remains a high impact perfume raw material in the presence of the modulator

TABLE 17

Examples of perfume raw materials that no longer remain available for selection for use in the high volatility component, but become available for selection for use in the medium volatility component, wherein the second vapor pressure of the perfume raw material has a range of 0.0008 to 0.08 Torr at 22° C.
Modulator (15 wt %, relative to the total weight of the composition)

| PPG-20 methyl glucose ether and octyldodecanol (2:1) | PPG-20 methyl glucose ether and isostearyl alcohol (2:1) | PPG-20 methyl glucose ether and isocetyl alcohol (2:1) | PPG-20 methyl glucose ether and vehicle |
|---|---|---|---|
| | | | zestover* |

*Denotes a high impact perfume raw material that remains a high impact perfume raw material in the presence of the modulator

TABLE 18

Examples of perfume raw materials remain available for selection for use in the medium volatility component, wherein the second vapor pressure of the perfume raw has a range of 0.0008 to 0.08 Torr at 22° C.
Modulator (15 wt %, relative to the total weight of the composition)

| PPG-20 methyl glucose ether and octyldodecanol (2:1) | PPG-20 methyl glucose ether and isostearyl alcohol (2:1) | PPG-20 methyl glucose ether and isocetyl alcohol (2:1) | PPG-20 methyl glucose ether and vehicle |
|---|---|---|---|
| citral | citral | citral* | citral* |
| | | Aldehyde C12* | Aldehyde C12* |
| | | citronellol* | citronellol* |
| | | | geraniol |
| | | | nerol[§] |

TABLE 18-continued

Examples of perfume raw materials remain available for selection for use in the medium volatility component, wherein the second vapor pressure of the perfume raw has a range of 0.0008 to 0.08 Torr at 22° C. Modulator (15 wt %, relative to the total weight of the composition)

| PPG-20 methyl glucose ether and octyldodecanol (2:1) | PPG-20 methyl glucose ether and isostearyl alcohol (2:1) | PPG-20 methyl glucose ether and isocetyl alcohol (2:1) | PPG-20 methyl glucose ether and vehicle |
|---|---|---|---|
| | | foliaver decalactone* javanol | foliaver decalactone* javanol |

§Denotes a high impact perfume raw material that became a low impact perfume raw material in the presence of the modulator
*Denotes a high impact perfume raw material that remains a high impact perfume raw material in the presence of the modulator

TABLE 19

Examples of perfume raw materials that no longer remain available for selection for use in the medium volatility component, but become available for selection for use in the low volatility component, wherein the second vapor pressure of the perfume raw material is less than 0.0008 Torr at 22° C. Modulator (15 wt %, relative to the total weight of the composition)

| PPG-20 methyl glucose ether and octyldodecanol (2:1) | PPG-20 methyl glucose ether and isostearyl alcohol (2:1) | PPG-20 methyl glucose ether and isocetyl alcohol (2:1) | PPG-20 methyl glucose ether and vehicle |
|---|---|---|---|
| Aldehyde C12* citronellol* geraniol⁺ nerol foliaver decolactone* lilial heliopropanal* javanol calone* | Aldehyde C12* citronellol* geraniol nerol foliaver decolactone§ lilial helioprop anal* javanol⁺ calone* | geraniol⁺ nerol⁺ lilial heliopropanal⁺ calone* | nerol lilial* heliopropanal* calone* |

§Denotes a high impact perfume raw material that became a low impact perfume raw material in the presence of the modulator
*Denotes a high impact perfume raw material that remains a high impact perfume raw material in the presence of the modulator
⁺Denotes a perfume raw material that becomes suppressed in the presence of the modulator

TABLE 20

Examples of perfume raw materials that remain available for selection for use in the low volatility component, wherein the second vapor pressure of the perfume raw is less than 0.0008 Torr at 22° C. Modulator (15 wt %, relative to the total weight of the composition)

| PPG-20 methyl glucose ether and octyldodecanol (2:1) | PPG-20 methyl glucose ether and isostearyl alcohol (2:1) | PPG-20 methyl glucose ether and isocetyl alcohol (2:1) | PPG-20 methyl glucose ether and vehicle |
|---|---|---|---|
| hedione bacdanol* astrotone⁺ | hedione bacdanol⁺ astrotone⁺ | hedione bacdanol⁺ astrotone⁺ | hedione bacdanol* astrotone⁺ |

Figure 6:
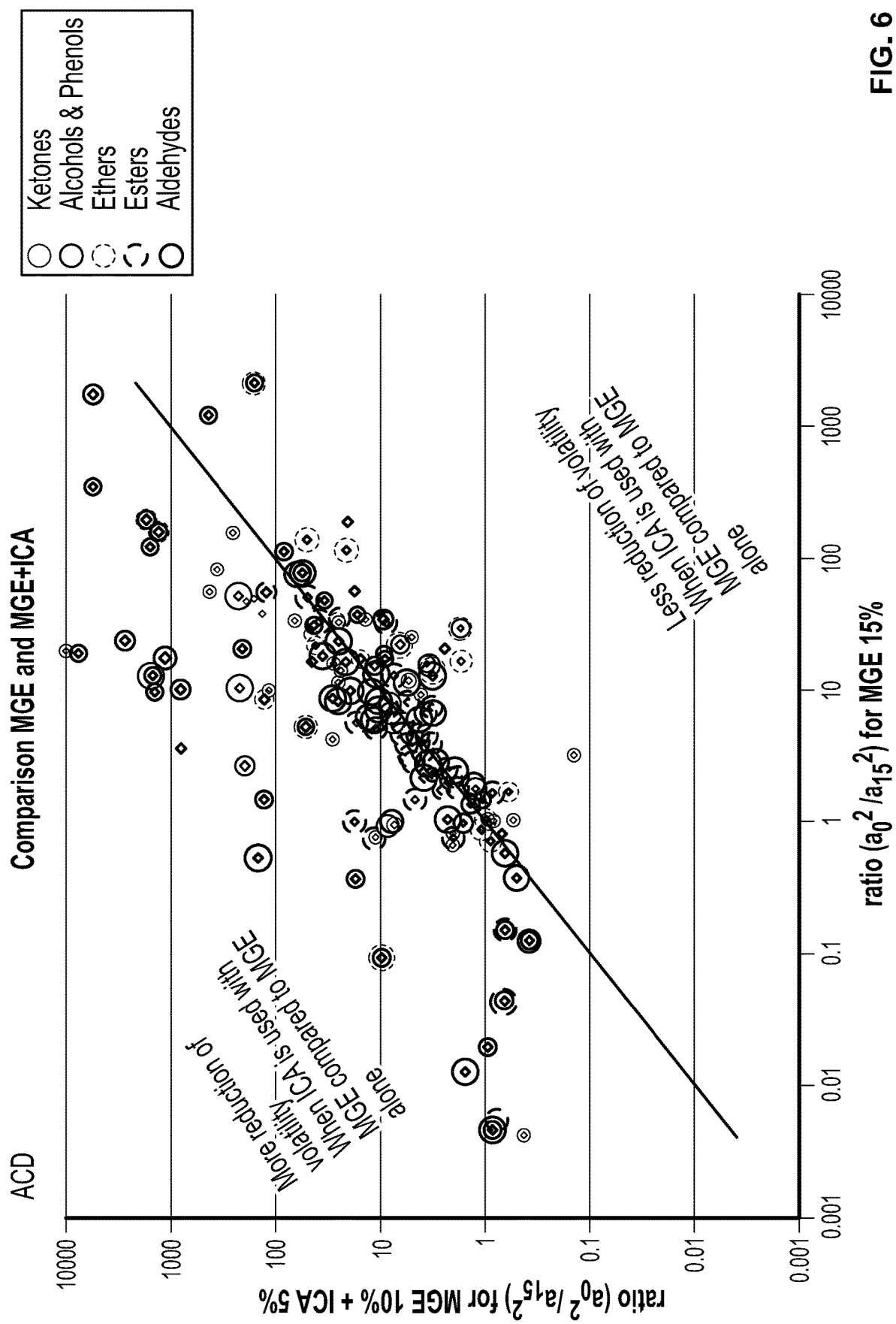
FIG. 6 denotes perfume raw materials wherein the second vapor pressure is different in a modulator comprising 15 wt % PPG-20 methyl glucose ether ("MGE"), relative to the total weight of the composition, compared to a modulator comprising 10 wt % PPG-20 methyl glucose ether and 5 wt % isocetyl alcohol ("ICA").

*Denotes a high impact perfume raw material that remains a high impact perfume raw material in the presence of the modulator
⁺Denotes a perfume raw material that becomes suppressed in the presence of the modulator Taken together, the data presented in Examples 1 and 2 demonstrate that the effect that one modulator may have on the second vapor pressure of a given perfume raw material may be different than another modulator. This is further illustrated in FIG. 6, which denotes perfume raw materials wherein the second vapor pressure is different in a modulator comprising 15 wt % PPG-20 methyl glucose ether, relative to the total weight of the composition, compared to a modulator comprising 10 wt % PPG-20 methyl glucose ether and 5 wt % isocetyl alcohol.

Example 3: The Effect of an at Least One Modulator on Fragrance Retention

The following fragrance was used in the construction of a composition according to an aspect presented herein

| Fragrance PRM | Impact | parts |
|---|---|---|
| ALDEHYDE C 10 | 106.40 | 0.2 |
| ALDEHYDE MNA | 6864.37 | 0.1 |
| CALONE ® | 2393.11 | 1 |
| CASHMERAN | 193.68 | 1 |
| CITRONELLOL BJ | 790.85 | 20 |
| CYCLOSAL | 304.19 | 5 |
| DIHYDROMYRCENOL | 412.17 | 102 |
| DYNASCONE ® | 7594.65 | 1 |
| FLORALOZONE | 690.88 | 1 |
| FLORHYDRAL | 329.29 | 13 |
| FLOROL ® | 195.49 | 50 |
| GALBANOLENE SUPER | 742.41 | 6 |
| HELIOTROPIN | 1506.75 | 2 |
| LIMINAL ® | 1173.98 | 5 |
| NEROL BJ | 2381.32 | 10 |
| POLYWOOD ® | 775.63 | 20 |
| TRANS DECENAL | 4765.96 | 1 |
| UNDECAVERTOL | 163.06 | 1 |
| VIOLETTYNE 10 MIP | 160.20 | 1 |
| ZESTOVER | 187.33 | 17 |

Samples of the compositions were constructed as follows, where the at least one modulator was added to the ethanol fraction, followed by the addition of the fragrance:

| | (% wt) |
|---|---|
| Fragrance | 5.00% |
| Modulator (either 1PM or Hedione) | 15.00% |
| EtOH 40 B | 75.00% |
| H₂O | 5.00% |
| Total | 100.00% |

Figure 7:
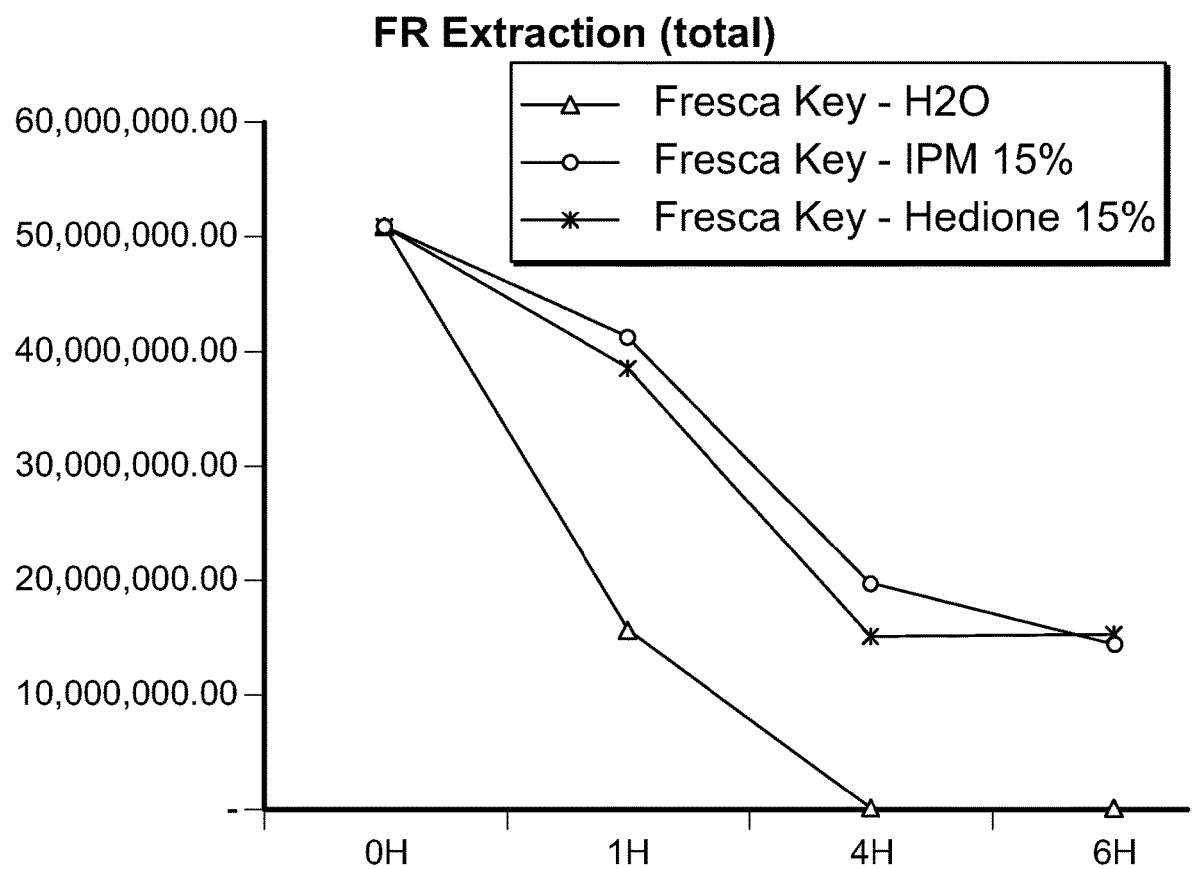
FIG. 7 shows the effect of either HEDIONE or IPM on the retention of the fragrance component of a sample over time.

Extraction of dry down and headspace analysis was done using GC-MS instrument and fragrance applied as described as follows: 10 µl of the composition was added to an aluminum crucible, using a positive displacement pipette. The crucible was then placed on a slide warmer, set at 32° C., wherein the slide warmer was open to the air. The crucible was removed at 0, 2, and 4 hours, and placed into a 2 ml GC vial. When placed into the vial, 600 µl of ethanol was added to the GC vial, and the residual fragrance within the sample was determined via GC/MS. The results are shown in FIG. 7. Referring to FIG. 7, the presence of either IPM or HEDIONE in the composition increased the retention of the fragrance in the sample, compared to a sample lacking an at least one modulator (water control).

Figure 8A:
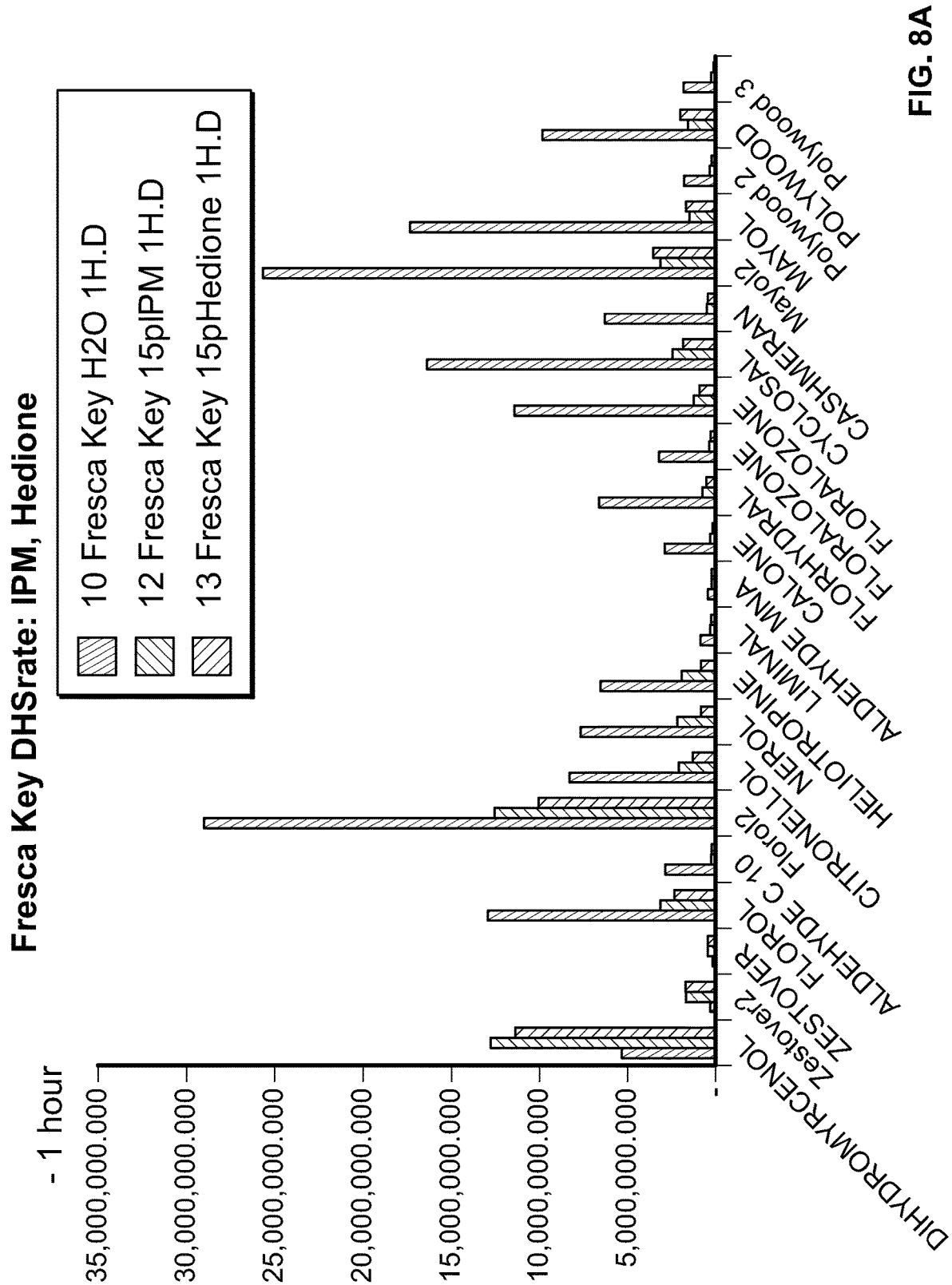
FIG. 8 a-c shows the effect of either HEDIONE or IPM on the amount of various perfume raw materials released into a headspace, following 1, 4, and 6 hours dry down, respectively.
Figure 8B:
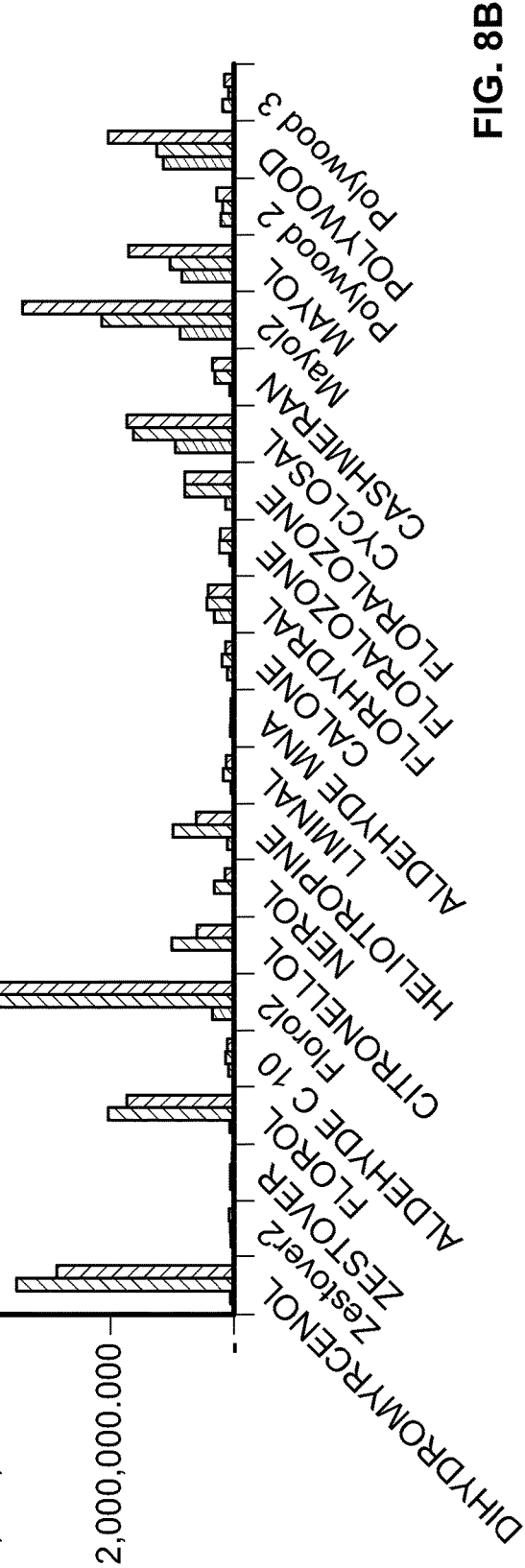
Figure 8C:
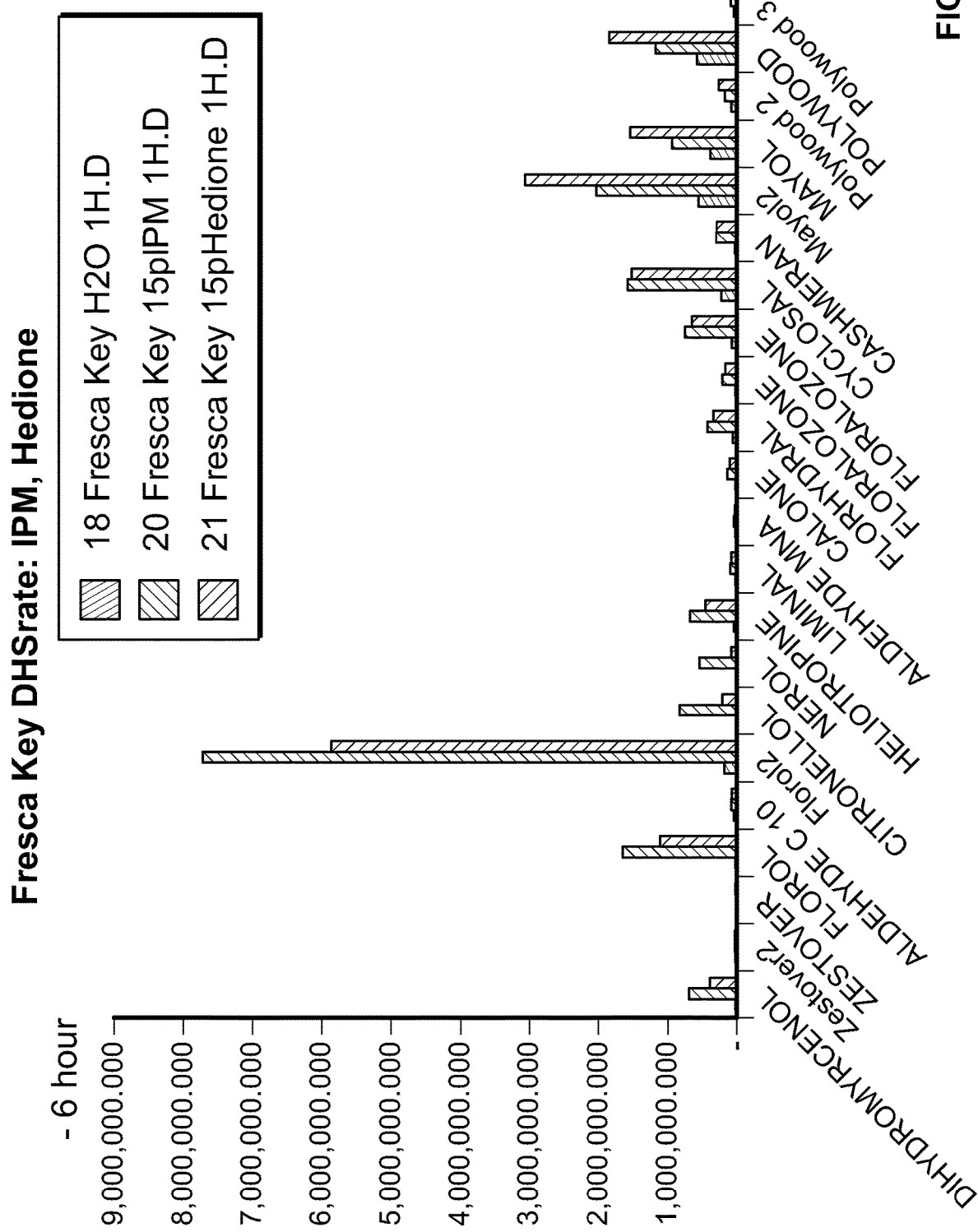

The rate of release of the fragrance from the sample was also determined in parallel samples. The results of the release of various perfume raw materials into the headspace are shown in FIG. 8. The rate of release of perfume raw materials into the headspace observed was initially slower with either the modulator HEDIONE or IPM. However, the release of release increase, and was much greater that that observed with water, after either 4, or 6 hours dry down.

Example 4: The Effect of an at Least One Modulator on Fragrance Retention

The following fragrance was used in the construction of a composition according to an aspect presented herein.

| Status | Fragrance PRM | % |
|---|---|---|
| TOP | ALDEHYDE C 9 | 0.03 |
| TOP | SAFRANAL | 0.13 |
| TOP | LINALOL BJ | 8.68 |
| TOP | DIHYDROMYRCENOL PUR | 9.64 |
| TOP | ACETATE C 9 | 6.43 |
| Top | NEROL BJ | 8.03 |
| Middle | ALDEHYDE C 12 | 0.03 |
| Middle | DAMAROSE ALPHA | 1.29 |
| Middle | METHYL ANTHRANILATE | 0.22 |
| Middle | GERANIOL PUR | 7.39 |
| Middle | FLOROL ® | 25.71 |
| Middle | CIS JASMONE | 0.19 |
| Bottom | IRALIA ® | 4.18 |
| Bottom | MAYOL ® | 3.21 |
| Bottom | INDOL | 0.16 |
| Bottom | GAMMA NONALACTONE | 0.26 |
| Bottom | CYCLOSAL | 4.82 |
| Bottom | EUGENOL F | 0.32 |
| Bottom | ALCOOL CINNAMIQUE ORD | 3.21 |
| Bottom | HYDROXYCITRONELLAL | 16.07 |
|  |  | 100.00 |

Compositions comprising either the modulator HEDIONE at 15% or the modulator benzyl salycilate at 15% were constructed. Fragrance retention and rate of release into a headspace from the compositions was determined according to the methods described in Example 3 above, wherein samples were taken following 1 and 4 hours dry down. The results for fragrance retention are shown in FIGS. 9 a and b, and 10 respectively.

Figure 9A:
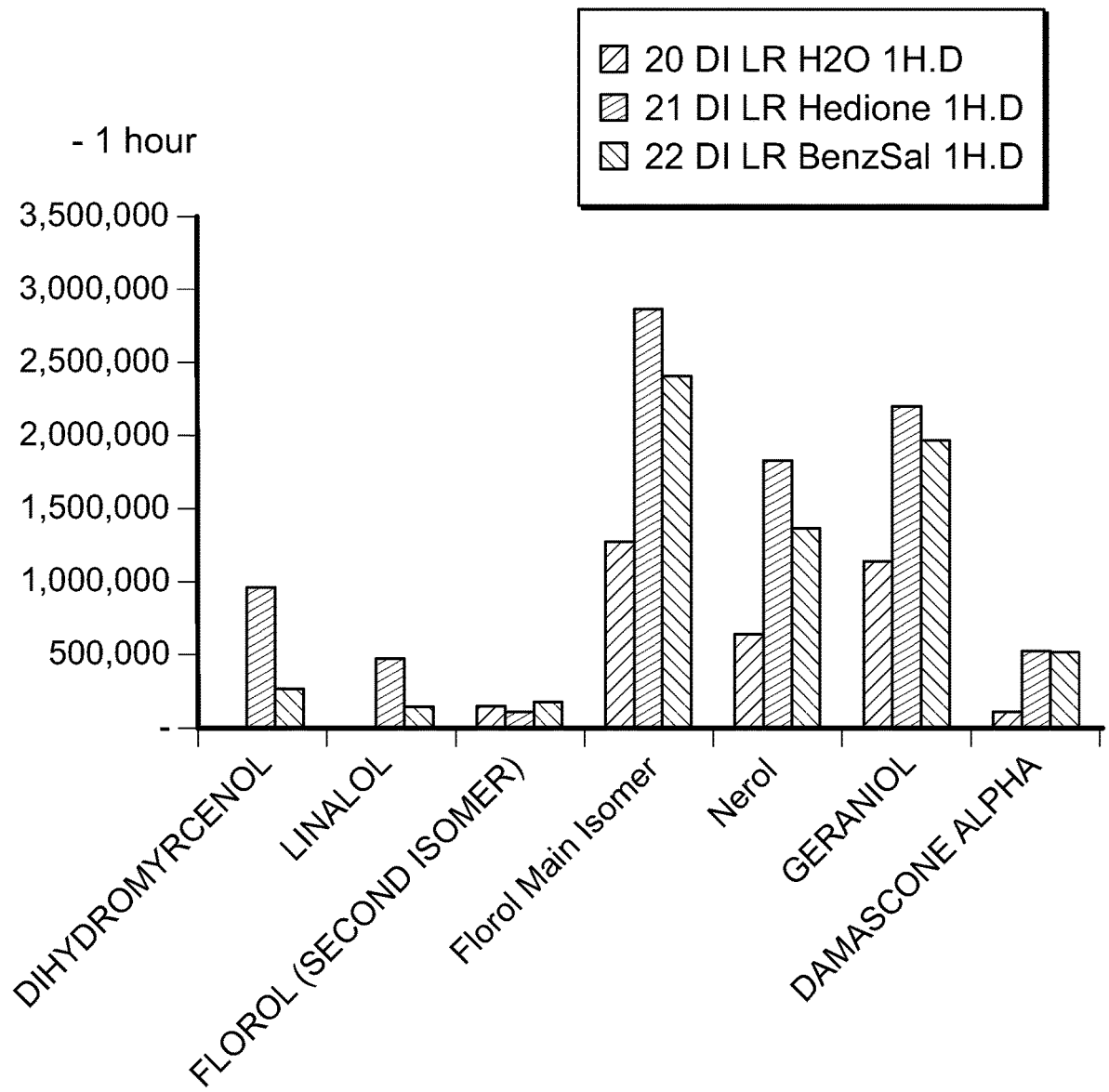
FIGS. 9 a and b shows the effect of either HEDIONE or benzyl salicylate on the retention of the fragrance component of a sample over time, following 1, and 4 hours dry down, respectively.
Figure 9B:
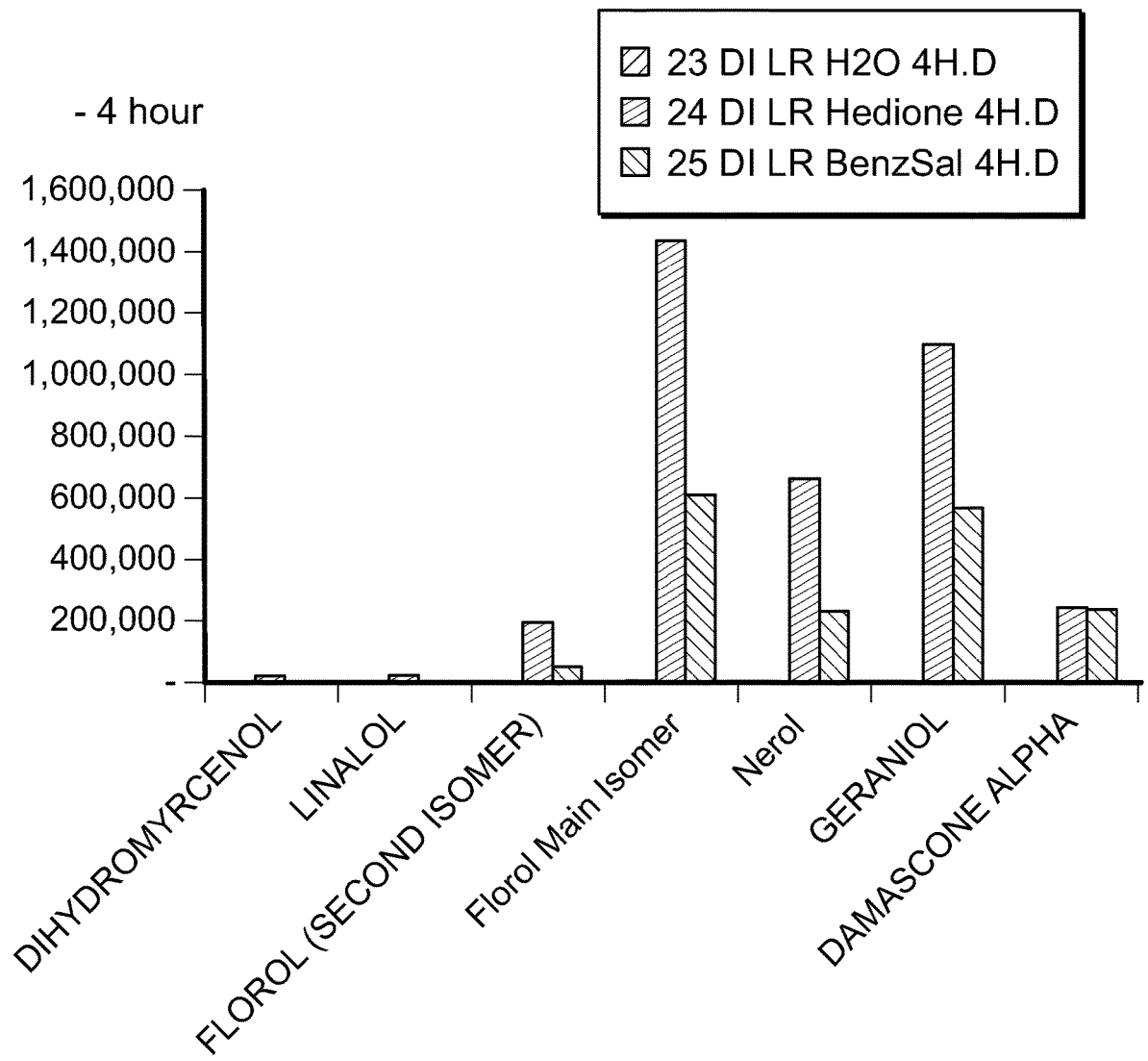
Figure 10:
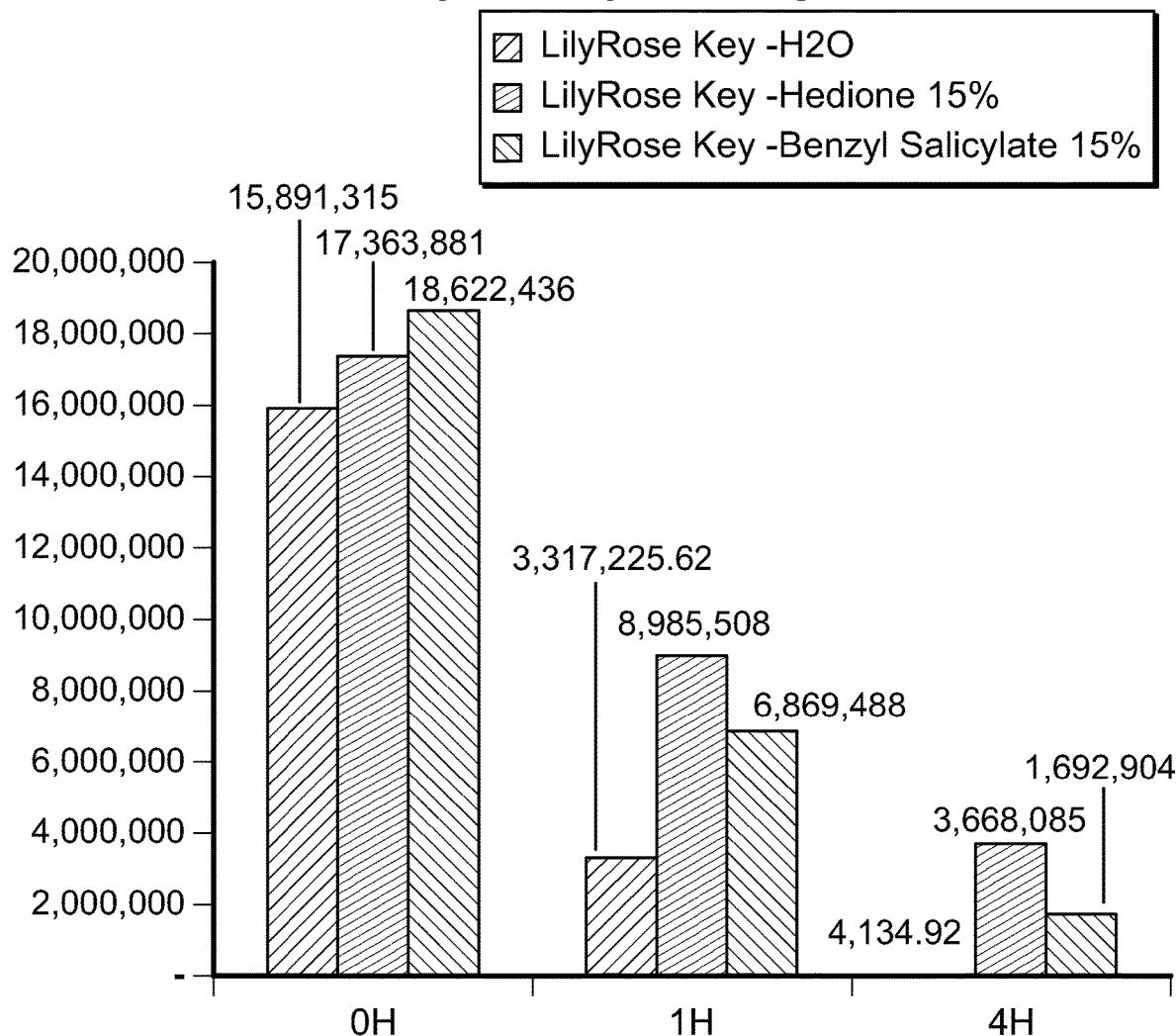
FIG. 10 shows the effect of either HEDIONE or benzyl salicylate on the retention of the fragrance component of a sample over time, following 0, 1, and 4 hours dry down, respectively.

Referring to FIGS. 9 and 10, while both HEDIONE and benzyl salicylate both increased the retention of fragrance within the crucible over time, compared to compositions comprising water instead of an at least one modulator, the amount of fragrance retained benzyl salicylate was used as the at least one modulator was less than that observed when HEDIONE was used as the at least one modulator.

Benzyl Salicylate and Hedione's Hansen solubility factors are shown below relative to the Hansen solubility factors of top and middle notes used in perfumery.

|  | D | P | H |
|---|---|---|---|
| HEDIONE ® | 16.85 | 3.76 | 5.51 |
| BENZYL SALICYLATE | 19.02 | 8.30 | 11.94 |

| TOP NOTES | | | |
|---|---|---|---|
|  | D | P | H |
| Average | 15.83 | 4.16 | 6.72 |
| STDev | 3.59 | 2.67 | 4.14 |

| MIDDLE NOTES | | | |
|---|---|---|---|
|  | D | P | H-bond |
| Average | 16.85 | 4.61 | 7.66 |
| STDev | 2.71 | 3.07 | 3.28 |

Without intending to be limited to any particular theory, given the Hansen solubility factors of both HEDIONE and benzyl salicylate, the interaction of the modulator HEDIONE with top and middle notes is expected to be greater than the interaction of the modulator benzyl salicylate with top and middle notes.

Example 5: The Effect of an at Least One Modulator on Fragrance Retention

The following fragrance was used in the construction of a composition according to an aspect presented herein.

| Fragrance PRM | Impact | parts |
|---|---|---|
| ALDEHYDE C 10 | 106.40 | 0.2 |
| ALDEHYDE MNA | 6864.37 | 0.1 |
| CALONE ® | 2393.11 | 1 |
| CASHMERAN | 193.68 | 1 |
| CITRONELLOL BJ | 790.85 | 20 |
| CYCLOSAL | 304.19 | 5 |
| DIHYDROMYRCENOL | 412.17 | 102 |
| DYNASCONE ® | 7594.65 | 1 |
| FLORALOZONE | 690.88 | 1 |
| FLORHYDRAL | 329.29 | 13 |
| FLOROL ® | 195.49 | 50 |
| GALBANOLENE SUPER | 742.41 | 6 |
| HELIOTROPIN | 1506.75 | 2 |
| LIMINAL ® | 1173.98 | 5 |
| NEROL BJ | 2381.32 | 10 |
| POLYWOOD ® | 775.63 | 20 |
| TRANS DECENAL | 4765.96 | 1 |
| UNDECAVERTOL | 163.06 | 1 |
| VIOLETTYNE 10 MIP | 160.20 | 1 |
| ZESTOVER | 187.33 | 17 |

Compositions comprising either the modulator HEDIONE at 15% or the modulator benzyl salycilate at 15% were constructed. Fragrance retention and rate of release into a headspace from the compositions was determined according to the methods described in Example 3 above, wherein samples were taken following 1 and 4 hours dry down. The results for fragrance retention are shown in FIGS. 11 a and b, and 12 respectively.

Figure 11A:
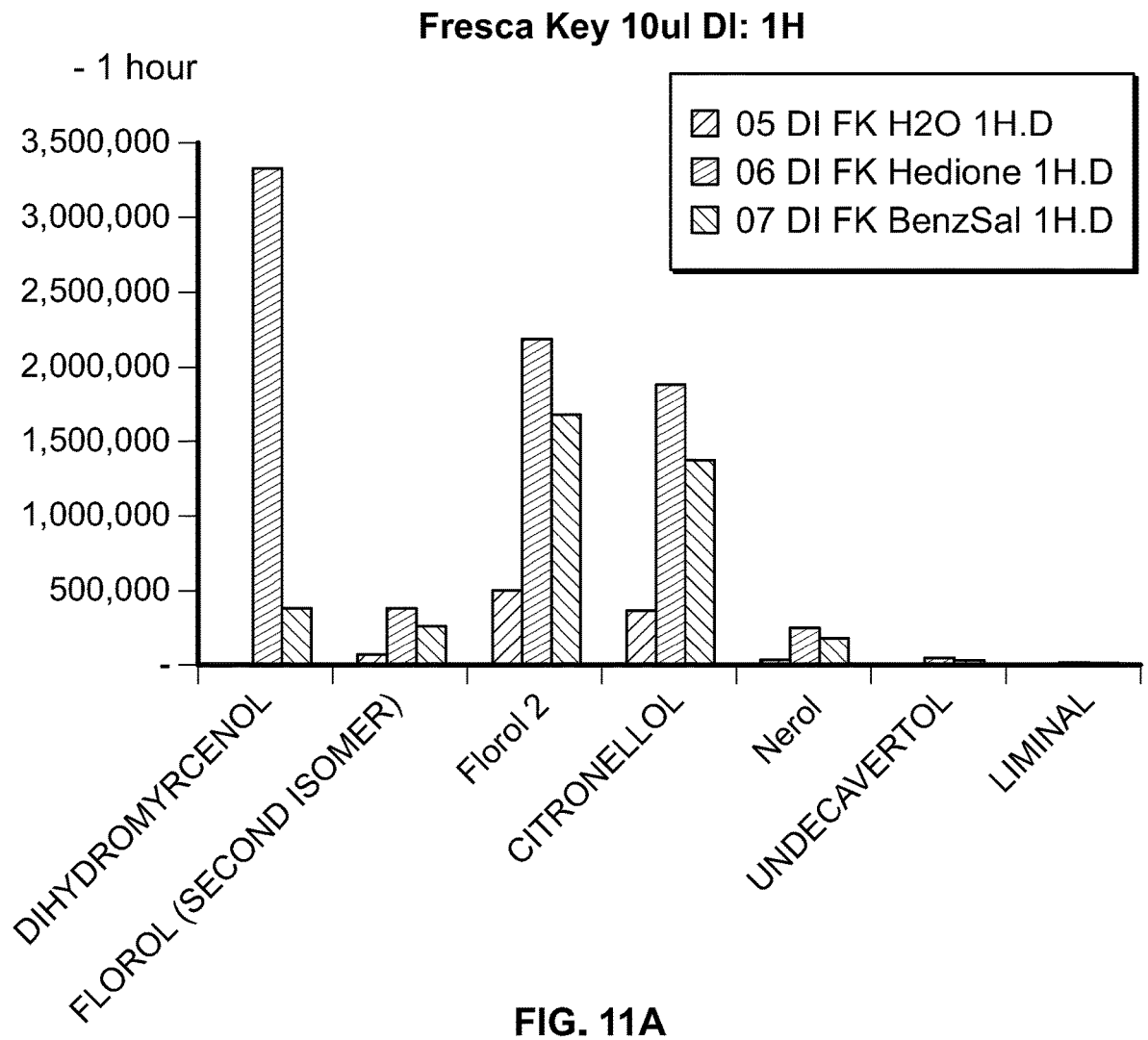
FIGS. 11 a and b shows the effect of either HEDIONE or benzyl salicylate on the retention of the fragrance component of a sample over time, following 1, and 4 hours dry down, respectively.
Figure 11B:
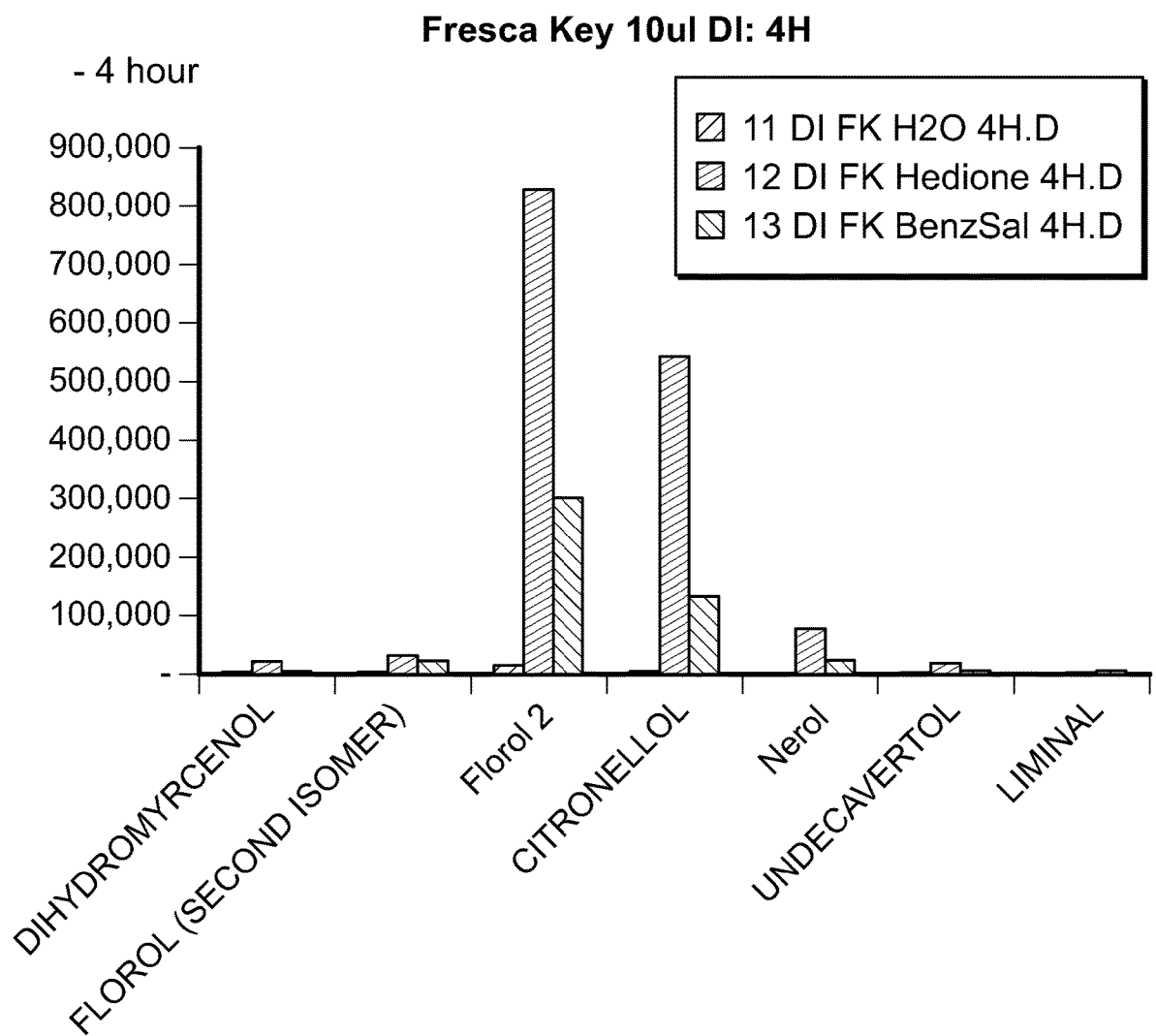
Figure 12:
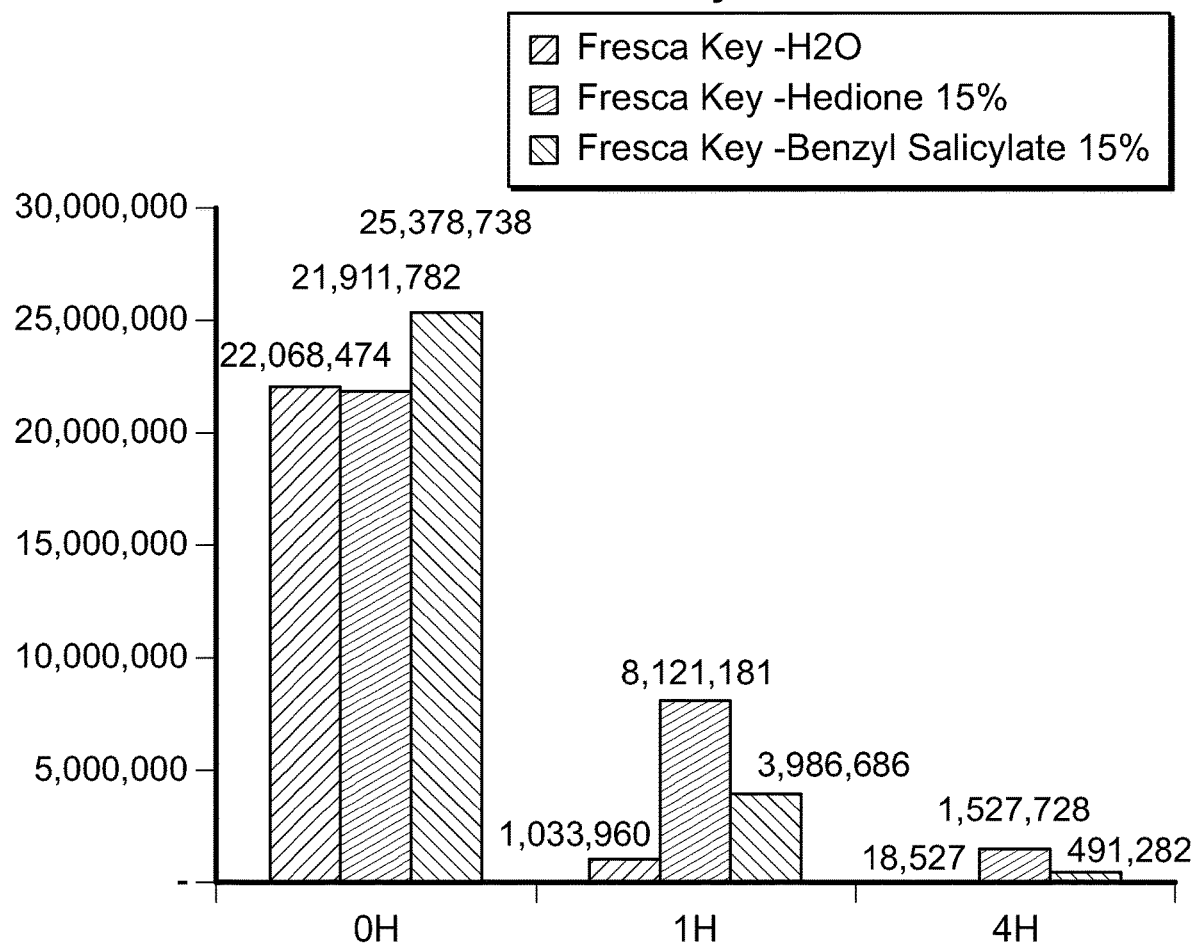
FIG. 12 shows the effect of either HEDIONE or benzyl salicylate on the retention of the fragrance component of a sample over time, following 0, 1, and 4 hours dry down, respectively.

Referring to FIGS. 11 and 12, while both HEDIONE and benzyl salicylate both increased the retention of fragrance within the crucible over time, compared to compositions comprising water instead of an at least one modulator, the amount of fragrance retained benzyl salicylate was used as the at least one modulator was less than that observed when HEDIONE was used as the at least one modulator.

Benzyl Salicylate and Hedione's Hansen solubility factors are shown below relative to the Hansen solubility factors of top and middle notes used in perfumery.

|  | D | P | H |
|---|---|---|---|
| HEDIONE ® | 16.85 | 3.76 | 5.51 |
| BENZYL SALICYLATE | 19.02 | 8.30 | 11.94 |

| TOP NOTES | | | |
|---|---|---|---|
| | D | P | H |
| Average | 15.83 | 4.16 | 6.72 |
| STDev | 3.59 | 2.67 | 4.14 |

| MIDDLE NOTES | | | |
|---|---|---|---|
| | D | P | H-bond |
| Average | 16.85 | 4.61 | 7.66 |
| STDev | 2.71 | 3.07 | 3.28 |

Without intending to be limited to any particular theory, given the Hansen solubility factors of both HEDIONE and benzyl salicylate, the interaction of the modulator HEDIONE with top and middle notes is expected to be greater than the interaction of the modulator benzyl salicylate with top and middle notes.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A composition:
wherein the composition comprises:
a. ethanol, in an amount from 30 to 75 wt % relative to the total weight of the composition;
b. a fragrance component present in an amount from 0.04 to 40 wt %, relative to the total weight of the composition,
wherein the fragrance component comprises:
  i. a high volatility component an amount from 0.08 to 55 wt % of the fragrance component, comprising
    a. a first at least one perfume raw material having a first vapor pressure greater than 0.08 Torr at 22° C.; and optionally
    b. a second at least one perfume raw material having a first vapor pressure greater than 0.08 Torr at 22° C.;
  ii. a medium volatility component in an amount from 0.08 to 85 wt % of the fragrance component, comprising:
    a. a first at least one perfume raw material having a first vapor pressure range of 0.0008 to 0.08 Torr at 22° C.; and optionally
    b. a second at least one perfume raw material having a first vapor pressure range of 0.0008 to 0.08 Torr at 22° C.; and
c. at least one modulator selected from the group consisting of: dodecanol; 3-Methyl-5-(2,2,3-trimethylcyclopent-3-en-1-yl)pentan-2-ol; (E)-1,2-Dimethoxy-4-(prop-1-en-1-yl)benzene; Cyclopentadecanone; 3,7,11-trimethyl-1,6,10-dodecatrien-3-ol; 6,10-Dimethyl-3-oxa-9-undecenal; (4E,8E)-1,5,9-trimethyl-13-oxabicyclo[10.1.0]trideca-4,8-diene; 6-[(E)-pent-2-enyl]oxan-2-one; Aceticacid,(1-oxopropoxy)-, 1-(3,3-dimethylcyclohexyl) ethyl; 4-α,5-Dimethyl-1,2,3,4,4α,5,6,7-octahydro-7-keto-3-isopropenylnaphthalene; (+-)-(1E)-1-(2,6,6-trimethyl-2-cyclohexen-1-yl)-1,6-heptadien-3-one (A); (1E)-1-(2,6,6-trimethyl-1-cyclohexen-1-yl)-1,6-heptadien-3-one (B); Methyl 2-(3-oxo-2-pentylcyclopentyl) ethanoate; hexyl 2-hydroxybenzoate; oxacyclohexadecan-2-one; 3-methylcyclopentadecan-1-one; cyclopentadec-4-en-1-one; (8E)-1-oxacycloheptadec-8-en-2-one; methyl 2-[(1R,2S)-3-oxo-2-pentylcyclopentyl]acetate; methyl 2-[(1R,2R)-3-oxo-2-[(Z)-pent-2-enyl]cyclopentyl]acetate; 4,6,6,7,8,8-hexamethyl-1,3,4,7-tetrahydrocyclopenta[g]isochromene; 6-heptyloxan-2-one; benzyl benzoate; (2E)-2-benzylideneheptanal; (2E)-2-benzylideneoctanal; (9Z)-cycloheptadec-9-en-1-one; propan-2-yl tetradecanoate; and combinations thereof;
in an amount from 5.0 to 20 wt %, relative to the total weight of the composition;
wherein the first vapor pressure of the at least one first perfume raw material of the high volatility component is determined in the absence of the at least one modulator;
wherein the first vapor pressure of the at least one second perfume raw material of the high volatility component is determined in the absence of the at least one modulator;
wherein the at least one modulator changes the first vapor pressure of the at least one second perfume raw material of the high volatility component to a second vapor pressure;
wherein the second vapor pressure of the at least one second perfume raw material of the high volatility component is in the range of 0.0008 to 0.08 Torr at 22° C.;
wherein the first vapor pressure range of the at least one first perfume raw material of the medium volatility component is determined in the absence of the at least one modulator;
wherein the first vapor pressure range of the at least one second perfume raw material of the medium volatility component is determined in the absence of the at least one modulator;
wherein the at least one modulator changes the first vapor pressure range of the at least one second perfume raw material of the medium volatility component to a second vapor pressure; and
wherein the second vapor pressure of the at least one second perfume raw material of the medium volatility component is less than 0.0008 Torr at 22° C.

2. The composition of claim 1, wherein the fragrance component present in an amount from 0.04 to 20 wt %, relative to the total weight of the composition.

3. The composition of claim 1, wherein the composition further comprises water, in an amount of less than or equal to 15 wt % relative to the total weight of the composition.

4. The composition of claim 1, wherein the composition further comprises water, in an amount 5 to 15 wt % relative to the total weight of the composition.

5. The composition of claim 1, wherein the composition further comprises water, in an amount 0 to 5 wt % relative to the total weight of the composition.

6. The composition of claim 1, wherein the at least one modulator is in an amount from 6.0 to 20 wt %, relative to the total weight of the composition.

7. The composition of claim 1, wherein the at least one modulator is in an amount from 7.0 to 20 wt %, relative to the total weight of the composition.

8. The composition of claim 1, wherein the at least one modulator is in an amount from 8.0 to 20 wt %, relative to the total weight of the composition.

9. The composition of claim 1, wherein the at least one modulator is in an amount from 9.0 to 20 wt %, relative to the total weight of the composition.

10. The composition of claim 1, wherein the at least one modulator is in an amount from 10.0 to 20 wt %, relative to the total weight of the composition.

11. The composition of claim 1, wherein the at least one modulator is in an amount from 11.0 to 20 wt %, relative to the total weight of the composition.

12. The composition of claim 1, wherein the composition further comprises at least one hydrophilic solvent.

13. The composition of claim 8, wherein the at least one hydrophilic solvent is selected from the group consisting of: propylene glycol, dipropylene glycol, ethylene glycol, triethyl citrate, disiopropyl glycol monomethyl ether, diethylene glycol monoethyl ether; triacetin, methylmethoxybutanol, benzyl alcohol, propylene glycol n-butyl ether; a glycol ether, an ester of diethylene glycol, and a cellosolve derivative.

14. A perfuming consumer product comprising the composition of claim 1.

15. A method for modifying or enhancing the odor properties of a body surface comprising contacting or treating the body surface with the composition of claim 1.

16. A method for modifying or enhancing the odor properties of a substrate comprising contacting or treating the substrate the composition of claim 1.

* * * * *